United States Patent
Barnes et al.

(10) Patent No.: US 9,458,216 B2
(45) Date of Patent: Oct. 4, 2016

(54) NUCLEIC ACID ENCODING CHIMERIC IL-1 RECEPTOR TYPE I ANTAGONISTS

(71) Applicant: ELEVEN BIOTHERAPEUTICS, INC., Cambridge, MA (US)

(72) Inventors: Thomas M. Barnes, Brookline, MA (US); Jinzhao Hou, Belmont, MA (US); Bracken M. King, Boston, MA (US)

(73) Assignee: ELEVEN BIOTHERAPEUTICS, INC., Cambridge, MA (US)

( * ) Notice: Subject to any disclaimer, the term of this patent is extended or adjusted under 35 U.S.C. 154(b) by 221 days.

(21) Appl. No.: 14/460,563

(22) Filed: Aug. 15, 2014

(65) Prior Publication Data

US 2015/0087818 A1    Mar. 26, 2015

Related U.S. Application Data

(62) Division of application No. 13/812,582, filed as application No. PCT/US2011/045995 on Jul. 29, 2011, now Pat. No. 8,853,150.

(60) Provisional application No. 61/493,966, filed on Jun. 6, 2011, provisional application No. 61/493,967, filed on Jun. 6, 2011, provisional application No. 61/436,178, filed on Jan. 25, 2011, provisional application No. 61/436,184, filed on Jan. 25, 2011, provisional application No. 61/368,799, filed on Jul. 29, 2010.

(51) Int. Cl.
   C12N 15/12    (2006.01)
   C07K 14/545   (2006.01)
   A61K 38/00    (2006.01)

(52) U.S. Cl.
   CPC ............. *C07K 14/545* (2013.01); *A61K 38/00* (2013.01); *C07K 2319/00* (2013.01)

(58) Field of Classification Search
   CPC .......................... C07K 2319/00; C12N 15/11
   See application file for complete search history.

(56) References Cited

U.S. PATENT DOCUMENTS

| | | |
|---|---|---|
| 4,343,787 A | 8/1982 | Katz |
| 4,770,781 A | 9/1988 | Schmidt et al. |
| 4,804,539 A | 2/1989 | Guo et al. |
| 4,883,658 A | 11/1989 | Holly |
| 4,898,818 A | 2/1990 | Nakai et al. |
| 5,075,104 A | 12/1991 | Gressel et al. |
| 5,075,222 A | 12/1991 | Hannum et al. |
| 5,122,459 A | 6/1992 | Conlon, III et al. |
| 5,278,151 A | 1/1994 | Korb et al. |
| 5,286,847 A | 2/1994 | Gehrke et al. |
| 5,340,572 A | 8/1994 | Patel et al. |
| 5,349,051 A | 9/1994 | Veerapandian |
| 5,453,490 A | 9/1995 | Hageman et al. |
| 5,484,887 A | 1/1996 | Kronheim et al. |
| 5,510,462 A | 4/1996 | Auron et al. |
| 5,530,101 A | 6/1996 | Queen et al. |
| 5,578,586 A | 11/1996 | Glonek et al. |
| 5,585,089 A | 12/1996 | Queen et al. |
| 5,693,489 A | 12/1997 | Studier et al. |
| 5,693,761 A | 12/1997 | Queen et al. |
| 5,693,762 A | 12/1997 | Queen et al. |
| 5,739,277 A | 4/1998 | Presta et al. |
| 5,770,401 A | 6/1998 | Mullarkey |
| 5,789,650 A | 8/1998 | Lonberg et al. |
| 5,861,476 A | 1/1999 | Barrett et al. |
| 5,922,573 A | 7/1999 | Boraschi et al. |
| 5,985,657 A | 11/1999 | Auron et al. |
| 5,998,578 A | 12/1999 | Auron et al. |
| 6,090,775 A | 7/2000 | Rothwell et al. |
| 6,096,728 A | 8/2000 | Collins et al. |
| 6,107,465 A | 8/2000 | Nakai et al. |
| 6,159,460 A | 12/2000 | Thompson et al. |
| 6,337,072 B1 | 1/2002 | Ford et al. |
| 6,407,213 B1 | 6/2002 | Carter et al. |
| 6,416,753 B1 | 7/2002 | Yuan et al. |
| 6,419,944 B2 | 7/2002 | Tobinick |
| 6,471,961 B1 | 10/2002 | Tobinick |
| 6,599,873 B1 | 7/2003 | Sommer et al. |
| 6,602,503 B1 | 8/2003 | Lobb et al. |
| 6,623,736 B2 | 9/2003 | Tobinick |
| 6,858,409 B1 | 2/2005 | Thompson et al. |

(Continued)

FOREIGN PATENT DOCUMENTS

| | | |
|---|---|---|
| CA | 2648223 A1 | 10/2007 |
| EP | 36776 A2 | 9/1981 |

(Continued)

OTHER PUBLICATIONS

Aksentijevich et al. "De novo CIAS1 mutations, cytokine activation, and evidence for genetic heterogeneity in patients with neonatal-onset multisystem inflammatory disease (NOMID): a new member of the expanding family of pyrin-associated autoinflammatory diseases" Arthritis Rheum 46:3340-3348, (2002).

Akuzawa et al. "Interleukin-1 Receptor Antagonist Attenuates the Severity of Spinal Cord Ischemic Injury in Rabbits." J. Vascular Surg. 48.3(2008):694-700.

Alt et al., "Liver-directed gene therapy: molecular tools and current preclinical and clinical studies" J. Hepatol. 23:746-58; (1995).

Altschul et al., "Basic local alignment search tool" J. Mol. Biol. 215, 403-410, (1990).

(Continued)

*Primary Examiner* — Prema Mertz

(57) ABSTRACT

Featured herein are non-naturally occurring cytokine domains that can be used, inter alia, to modulate cellular signalling responsive to interleukin-1 receptor I (IL-1RI), to treat disorders, and to detect and/or bind to cellular receptors, as well as other agents. Exemplary cytokine domains can contain amino acid residues from at least two parental cytokines domains, for example, receptor binding features, surface features, β strands, and loops from at least two parental cytokines domains.

29 Claims, 20 Drawing Sheets

(56) References Cited

U.S. PATENT DOCUMENTS

| | | |
|---|---|---|
| 6,927,044 B2 | 8/2005 | Stahl et al. |
| 6,974,682 B1 | 12/2005 | Bednarik et al. |
| 7,087,224 B2 | 8/2006 | Kay et al. |
| 7,482,323 B2 | 1/2009 | Hasty et al. |
| 7,619,066 B2 | 11/2009 | Raibekas et al. |
| 7,674,464 B2 | 3/2010 | Hasty et al. |
| 7,700,318 B2 | 4/2010 | Hui |
| 7,956,160 B2 | 6/2011 | Krishnan et al. |
| 8,303,945 B2 | 11/2012 | Dahlen et al. |
| 8,414,876 B2 | 4/2013 | Mellis et al. |
| 8,853,150 B2 | 10/2014 | Barnes et al. |
| 2001/0041792 A1 | 11/2001 | Donda et al. |
| 2001/0042304 A1 | 11/2001 | Sato |
| 2003/0004106 A1 | 1/2003 | Saris et al. |
| 2003/0007971 A1 | 1/2003 | Hara et al. |
| 2003/0026806 A1 | 2/2003 | Witte et al. |
| 2003/0070185 A1 | 4/2003 | Jakobovits et al. |
| 2003/0083301 A1 | 5/2003 | Perez-Polo et al. |
| 2003/0166069 A1 | 9/2003 | Welcher et al. |
| 2004/0022718 A1 | 2/2004 | Stupp et al. |
| 2004/0028872 A1 | 2/2004 | Edwards et al. |
| 2004/0044001 A1 | 3/2004 | Bendele et al. |
| 2004/0208872 A1 | 10/2004 | Welcher et al. |
| 2004/0208874 A1 | 10/2004 | Khare |
| 2005/0023872 A1 | 2/2005 | Hetzel et al. |
| 2005/0033694 A1 | 2/2005 | Perrin |
| 2005/0059589 A1 | 3/2005 | Mullarkey |
| 2005/0105830 A1 | 5/2005 | Chung et al. |
| 2005/0123512 A1 | 6/2005 | Calzone et al. |
| 2005/0143333 A1 | 6/2005 | Richards et al. |
| 2005/0171337 A1 | 8/2005 | Bednarik et al. |
| 2005/0271618 A1 | 12/2005 | Raibekas et al. |
| 2006/0088600 A1 | 4/2006 | Thornion et al. |
| 2006/0094663 A1 | 5/2006 | Chemtob et al. |
| 2006/0110429 A1 | 5/2006 | Reiff et al. |
| 2007/0027082 A1 | 2/2007 | Hasty et al. |
| 2007/0098684 A9 | 5/2007 | Raibekas et al. |
| 2007/0248597 A1 | 10/2007 | Henley et al. |
| 2008/0019964 A1 | 1/2008 | Olmarker et al. |
| 2008/0026485 A1 | 1/2008 | Hueber et al. |
| 2008/0199460 A1 | 8/2008 | Cua et al. |
| 2008/0242634 A1 | 10/2008 | Perez-Polo |
| 2009/0011745 A1 | 1/2009 | Cha |
| 2009/0022733 A1 | 1/2009 | Sims et al. |
| 2009/0111745 A1 | 4/2009 | Tomlinson |
| 2009/0136453 A1 | 5/2009 | Watkins |
| 2009/0176217 A1 | 7/2009 | Sella-Tavor et al. |
| 2009/0214619 A1 | 8/2009 | Reiff et al. |
| 2010/0028328 A1 | 2/2010 | Reiff et al. |
| 2010/0047204 A1 | 2/2010 | Yoo et al. |
| 2010/0120684 A1 | 5/2010 | Dahlen et al. |
| 2010/0183587 A1 | 7/2010 | Dana et al. |
| 2010/0203103 A1 | 8/2010 | Dana et al. |
| 2010/0226963 A1 | 9/2010 | Cooper et al. |
| 2011/0104236 A1 | 5/2011 | Dana et al. |
| 2012/0014970 A1 | 1/2012 | Dana et al. |
| 2013/0195868 A1 | 8/2013 | Adelman |
| 2014/0073556 A1 | 3/2014 | Berezin et al. |

FOREIGN PATENT DOCUMENTS

| | | |
|---|---|---|
| EP | 239400 A2 | 9/1987 |
| EP | 0343684 A1 | 11/1989 |
| EP | 362179 A2 | 4/1990 |
| EP | 0541920 A1 | 5/1993 |
| EP | 661992 A1 | 7/1995 |
| EP | 1778723 A2 | 5/2007 |
| WO | 9007861 A1 | 7/1990 |
| WO | 9117184 A1 | 11/1991 |
| WO | 9510298 A1 | 4/1995 |
| WO | 96/09323 A1 | 3/1996 |
| WO | 9634096 A1 | 10/1996 |
| WO | 98/22130 A1 | 5/1998 |
| WO | 9847921 A1 | 10/1998 |
| WO | 00/42072 A2 | 7/2000 |
| WO | 02/060919 A2 | 8/2002 |
| WO | 02062375 A1 | 8/2002 |
| WO | 03022213 A2 | 3/2003 |
| WO | 03068920 A2 | 8/2003 |
| WO | 2005086695 A2 | 9/2005 |
| WO | 2005097195 A2 | 10/2005 |
| WO | 2007039903 A2 | 4/2007 |
| WO | 2007/120828 A1 | 10/2007 |
| WO | 2007/145618 A1 | 12/2007 |
| WO | 2008049043 A2 | 4/2008 |
| WO | 2008/132485 A2 | 11/2008 |
| WO | 2008/155134 A1 | 12/2008 |
| WO | 2008145664 A1 | 12/2008 |
| WO | 2009/023270 A2 | 2/2009 |
| WO | 2009025763 A2 | 2/2009 |
| WO | 2009048961 A1 | 4/2009 |
| WO | 2009089036 A2 | 7/2009 |
| WO | 2010052505 A1 | 5/2010 |
| WO | 2010081091 A2 | 7/2010 |
| WO | 2010089522 A1 | 8/2010 |
| WO | 2010/118888 A1 | 10/2010 |
| WO | 2011/011797 A2 | 1/2011 |
| WO | 2011028344 A2 | 3/2011 |
| WO | 2011/044563 A2 | 4/2011 |
| WO | 2011/063195 A2 | 5/2011 |
| WO | 2011106697 A1 | 9/2011 |
| WO | 2011123813 A2 | 10/2011 |
| WO | 2011163452 A2 | 12/2011 |
| WO | 2012016203 A1 | 2/2012 |
| WO | 2012103240 A2 | 8/2012 |
| WO | 2012122985 A1 | 9/2012 |
| WO | 2013019652 A1 | 2/2013 |
| WO | 2014160371 A1 | 10/2014 |

OTHER PUBLICATIONS

Altschul et al., "Local alignment statistics", Methods in Enzymology 266, 460-480, (1996).

Ansel et al., Pharmaceutical Dosage Forms and Drug Delivery Systems, 7th Ed.., Lippincott Williams & Wilkins Publishers (1999).

Antin et al., "Recombinant human interleukin-1 receptor antagonist in the treatment of steroid-resistant graftversus-host disease", Blood, 84:1342-1348 (1994).

Arend, W.P., "Interleukin-1 Receptor Antagonist", Adv. Immunol., 54:167-223 (1993).

Arnold et al., "The impact of glycosylation on the biological function and structure of human immunoglobulins." Ann. Rev. Immunol. 25: 21-50 (2007).

Baker et al., "Protein structure prediction and structural genomics" Science 294(5540):93-6, 2001).

Barbino et al., "The Controlled-Environment Chamber: A New Mouse Model of Dry Eye" Invest. Ophthal. Vis. Sci., 46: 2766-2711 (2005).

Bardwell et al., Rheumatoid Arthritis Severity Scale: a brief, physician-completed scale not confounded by patient self-report of psychological functioning Rheumatology 41(1):38-45, (2002).

Barton et al., "Inflammatory cytokines in the tears of patients with ocular rosacea", Opthalmol., 104:1868-1874 (1997).

Battat et al. "Effects of Laser In Situ Keratomileusis on Tear Production, Clearance, and the Ocular Surface." Ophthalmol. 108(2001):1230-1235.

Benoist et al., "In vivo sequence requirements of the sv40 early promoter region", Nature, 290:304-310 (1981).

Berge, et al. "Pharmaceutical salts." J. Pharm. Sci. 66:1-19, (1977).

Beyer et al., "Crystal structures of the pro-inflammatory cytokine interleukin-23 and its complex with a high-affinity neutralizing antibody." J. Mol. Biol. (2008).

Biswas et al. "Counteracting CornealImmunoinflammatory Lesion with Interleukin-1 Receptor Antagonist Protein." J. Leukocyte Biol. 76(2004):868-875.

Boder et al., "Yeast surface display for directed evolution of protein expression, affinity, and stability." Methods Enzymol.;328:430-44, (2000).

Bolton, "Recent advances in the pharmacological control of experimental allergic encephalomyelitis (EAE) and the implications for multiple sclerosis treatment", Multiple Sclerosis, 143, (1995).

(56) References Cited

OTHER PUBLICATIONS

Boraschi et al. "Structure-function relationship in the IL-1 family" Frontiers in Bioscience: A Journal and Virtual Library 1, d270-308, (1996).
Boraschi, "Mapping of receptor binding sites on IL-1 beta by reconstruction of IL-1ra-like domains" J. Immunol., 155 (10):4719-25 (1995).
Bresnihan et al., "Interleukin-1 receptor antagonist", Rheum. Dis. Clin. North Am,., 24(3):615-628 (1998).
Brignole et al., "Flow cytobetric analysis of inflammatory markers in conjunctival epithelial cells of patients with dry eyes", Invest. Ophtalmol. Vis. Sci., 41(6):1356-1362 (2000).
Brinster et al., "Regulation of metallothionein-thymidine kinase fusion plasmids injected into mouse eggs", Nature, 296:39-42 (1982).
Brody, et al. "Adenovirus-mediated in vivo gene transfer" Ann. N.Y. Acad. Sci. 716:90-101; (1994).
Bron et al., "The Contribution of Meibomian Disease to Dry Eye", Ocul. Surf., 2:149-165 (2004).
Caron et al., "Chondroprotective effect of intraarticular injections of interleukin-1 receptor antagonist in experimental osteoarthritis", Arthritis Rheum., 39:1535-1544 (1996).
Carter et al., "Improved oligonucleotide site-directed mutagenesis using M13 vectors" Nucl. Acids Res.,13:4331, (1986).
Case et al. "The Amber biomolecular simulation programs." J. Computat. Chem. 26, 1668-1688, (2005).
Case et al., Amber 11, University of California, San Francisco, CA USA, (2010).
Cavanagh et al. "The Molecular Basis of Neurotrophic Keratitis." Acta Ophthamol.67.S19i(1989):115-134.
Chang et al., "Phenotypic expression in E. coli of a DNA sequence coding for mouse dihydrofolate reductase" Nature, 275:615 (1978).
Chang et al: Dual Biological Functions of an Interleukin-1 Receptor Antagonist-Interleukin-10 Fusion Protein and Its Suppressive Effects on Joint Inflamation, Immunology, vol. 1. 112, No. 4, Aug. 1, 2004, p. 643-650.
Chao et al. "Isolating and engineering human antibodies using yeast surface display" Nat Protoc.1(2):755-68, (2006).
Chothia et al. "Canonical structures for the hypervariable regions of immunoglobulins." J. Mol. Biol. 196:901-917, (1987).
Chothia et al., "Structural repertoire of the human VH segments.", J. Mol. Biol. 227:799-817, (1992).
Chothia, "The nature of the accessible and buried surfaces in proteins" J. Mol. Biol., 150:1 1-12, (1976).
Cohen, et al. "Treatment of rheumatoid arthritis with anakinra, a recombinant human interleukin-1 receptor antagonist, in combination with methotrexate: results of a twenty-four-week, multicenter, randomized, double-blind, placebo-controlled trial" Arthritis & Rheumatism 46, 614-24 (2002).
Colby et al. "Engineering antibody affinity by yeast surface display" Methods Enzymol., 388:348-58, (2004).
Current Protocols in Immunology, Unit 15.1; John Wiley & Sons, Inc. (2009).
Current Protocols in Immunology, Unit 15.2; John Wiley & Sons, Inc. (2009).
Current Protocols in Immunology, Unit 15.5, John Wiley & Sons, Inc. (2009).
Current Protocols in Immunology, Unit 4.4; John Wiley & Sons, Inc, (1995).
Current Protocols in Molecular Biology, Greene Publishing Associates, Sections 9.10, (1989).
Current Protocols in Molecular Biology, Greene Publishing Associates, Sections 9.11, (1989).
Current Protocols in Molecular Biology, Greene Publishing Associates, Sections 9.12, (1989).
Current Protocols in Molecular Biology, Greene Publishing Associates, Sections 9.13, (1989).
Current Protocols in Molecular Biology, Greene Publishing Associates, Sections 9.14, (1989).
Current Protocols in Molecular Biology, John Wiley & Sons, N. Y., 6.3.1-6.3.6, (1989).
Teoh et al., "Tailoring biological treatment: anakinra treatment of posterior uveitis associated with the CINCA syndrome", Br. J. Opthalmol., 91:263-264 (2007).
Thompson et al., "DbCustal: Rapid and reliable global multiple alignments of protein sequences detected by database searches", Nucl. Acids Res. 28, 2910-2926, (2000).
Thule, P. M. and Liu, J. M. "Regulated hepatic insulin gene therapy of STZ-diabetic rats." Gene Ther. 7:1744-52; (2000).
Tinubu et al., "Humanized antibody directed to the IL-2 receptor beta-chain prolongs primate cardiac allograft survival.", J. Immunol., 4330-4338, (1994).
Tomlinson et al. "Reshaping human antibodies for therapy" J. Mol. Biol. 227:776-798, (1992).
Tomlinson et al. "The structural repertoire of the human V kappa domain." EMBO J. 14(18):4628-38, (1995).
Traunecker et al. "Bispecific single chain molecules (Janusins) target cytotoxic lymphocytes on HIV infected cells." EMBO J 10:3655-3659 (1991).
Trittibach,et al. "Lentiviral-vector-mediated expression of murine IL-1 receptor antagonist or IL-10 reduces the severity of endotoxin-induced uveitis." Gene Ther. 15(22): 1478-88. (2008).
Tsai et al. "Suppression of experimental uveitis by a recombinant adeno-associated virus vector encoding interleukin-1 receptor antagonist." Mol Vis 15:1542-1552, (2009).
Urlaub et al., "Efficient cloning of single-copy genes using specialized cosmid vectors: Isolation of mutant dihydrofolate reductase genes" Proc. Natl. Acad. Sci. USA, 77:4216 (1980).
Urlinger, et al. "Exploring the sequence space for tetracyclinedependent transcriptional activators: Novel mutations yield expanded range and sensitivity" Proc. Natl. Acad. Sci. USA 97 (14):7963-7968, (2000).
Vigers et al. "Crystal structure of the type-I interleukin-1 receptor complexed with interleukin-1 J3" Nature 386: 190-194, (1997).
Viti et al., "Design and use of phage display libraries for the selection of antibodies and enzymes", Methods Enzymol.; 326:480-505; 2000.
Voronov et al. "IL-1 is required for tumor invasiveness and angiogenesis" PNAS 100:2645-2650 (2003).
Wagner et al., "Nucleotide sequence of the thymidine kinase gene of herpes simplex virus type 1", Proc. Natl. Acad. Sci. US.A., 78(3):1441-1445 (1980).
Ware et al., Arthritis Impact Measurement Scales or Arthritis Impact Measurement Scales 2, Med. Care. 37(5 Suppl): MS40-50, AIMS or AIMS2, (1999).
Wells et al., "Cassette mutagenesis: an effkient method for generation of multiple mutations at defined sites" Gene, 34:315, (1985).
Wieczorek, Z., et al., "A Hexapeptide VTKFYF from C-terminal Part of Interleukin-1 Receptor Antagonist, an Inhibitor of IL-1 - IL-1 Receptor Interaction," Polish Journal of Pharmacology, 49:107-117 (1997).
Wieczorek, Z., et al., "The Search for Inhibitors of Interleukin-1 Based on the Sequence of Interleukin-1 Receptor Antagonist," Biomed Pept. Proteins Nucleic Acids, 2(4):123-129 (1996-1997) (Abstract).
Wingren: "Fusion of a Signal Sequence to the Interleukin-1β Gene Directs the Protein From Cytoplasmic Accumulation to Extracellular Release", Cellular Immunology, Vo 1. 169, No. 2, May 1, 1996, p. 226-237.
Written Opinion & International Preliminary Report on Patentability Mailed Dec. 23, 2011 for PCT/US2011/045995.
Xu et al. "Decrease in the Corneal Sensitivity and Change in Tear Function in Dry Eye." Comea.15.3(1996):235-239 (Abstract).
Yamada et al. "Interleukin 1 Receptor Antagonist Suppresses Allosensitization in Corneal Transplantation." Arch. Ophthlmol. 116(1998):1351-1357.
Yamada et al., "Interleukin-1 receptor antagonist therapy and induction of anterior chamber-associated immune deviation-type tolerance after corneal transplantation", Invest. Opthalmol. Vis. Sci., 41 :4203- 4208 (2000).

(56) References Cited

OTHER PUBLICATIONS

Yamada et al., "Local suppression of IL-I by receptor antagonist in the rat model of corneal alkali injury", Exp. Eye Res., 76:161-167 (2003).
Yamasaki et al., "Interleukin-1 as a pathogenetic mediator of ischemic brain damage in rats", Stroke, 26:676-681 (1995).
Yang, "Gene Transfer into Mammalian Somatic Cells in Vivo" Crit. Rev. Biotechnol. 12:335-56, (1992).
Zoller et al., "Oligonucleotide-directed mutagenesis using M13-derived vectors: an efficient and general procedure for the production of point mutations in any fragment of DNA" Nucl. Acids Res., 10:6487, (1987).
Özcura, "Ocular Surface Disease Index for the Diagnosis of Dry Eye Syndrome" Ocul Immunol Inflamm.15(5):389-93 (Sep.-Oct. 2007).
Dana et al. "Corneal Antigen Presentation: Molecular Regulation and Functional Implications" The Ocular Surface, 3 (4):S169-S172, Oct. 2005.
Dana et al., "Topical interleukin 1 receptor antagonist promotes corneal transplant survival", Transplantation, 63 (10):1501-1507 (1997).
Dana et al., "Topical Modulation of interleukin-1 activity in corneal neovascularization", Cornea, 17(4):403-409 (1998) (Abstract).
Dana, "Comparison of topical interleukin-1 vs tumor necrosis factor-alpha blockade with corticosteroid therapy on murine corneal inflammation, neovascularization, and transplant survival (an American Ophthalmological Society thesis)" Trans Am Ophthalmol Soc 105: 330-43, (2007).
Dartt et al. "Dysfunctional Neural Regulation of Lacrimal Gland Secretion and its Role in the Pathogenesis of Dry Eye Syndrome." Ocul. Surf. 22(2004):76-91.
Database UniPort [Online] Jul. 23, 2010, anonymous: "IL1RA_MOUSE", retrieved from www.uniport.org, Database accession No. P25085.
Database Uniprot [Online] Jul. 13, 2010, anonymous: "IL1F5_HUMAN", retrieved from www.uniport.org Database accession No. Q9UBH0.
Database UniProt [Online] Jul. 13, 2010, anonymous: "IL1RA_HUMAN" retrieved from www.uniport.org.
Dayer et al., "Anti-interleukin-1 therapy in rheumatic diseases", Curr. Opin. Rheumatol., 13:170-176 (2001).
de Salamanca et al. "Tear cytokine and chemokine analysis and clinical correlations in evaporative-type dry eye disease" Mol. Vis. 16:862-873, (2010).
deBoer et al., "The tac promoter: A functional hybrid derived from the trp and lac promoters" Proc. Natl. Acad. Sci. USA, 80:21-25 (1983).
Dekaris et al., Effect of topical interleukin-1 receptor antagonist (IL-1ra) on corneal allograft survival in presensitized hosts, Curr Eye Res 19(5): 456-9, (1999).
DeKosky et al. "Interleukin-1 Receptor Antagonist Suppresses Neurotrophin Response in Injured Rat Brain." Ann. Neural. 39(1996):123-127.
Demircan et al. Determination of vitreous interleukin-1(IL-1) and tumour necrosis factor (TNF) levels in proliferative diabetic retinopathy, Eye 20:1366-1369, (2006).
Dennis et al. "Albumin Binding as a General Strategy for Improving the Pharmacokinetics of Proteins" J. Biol. Chem. 277:35035-35043 (2002).
Deutscher, "Maintaining protein stability." Methods in Enzymology, 182, 83-89 (1990).
Dinarello et al., Current Protocols in Immunology, Ch. 6.2.1-6.2.7, John Wiley and Sons Inc., (2000).
Dinarello, C.A., "Biologic basis for interleukin", Blood, 87(6):2095-2147 (1996).
Dinarello, C.A., "The role of the interleukin-1-receptor antagonist in blocking inflammation mediated by interleukin-1", N Engl. J Med., 343(10):732-734 (2000).

Dinarello: Imunological and Inflamatory Functions of the Interleukin-l Family, Annual Review of Immunology, vo 1.27, No. 1, 1 Apr. 1, 2009, pp. 519-550.
Doganay et al. Comparison of serum NO, TNF-beta, IL-1beta, sIL-2R, IL-6 and IL-8 levels with grades of retinopathy in patients with diabetes mellitus Eye, 16:163-170, (2006).
Duncan et al., "Repair of myelin disease: strategies and progress in animal models" Molec. Med. Today, 554-561, (1997).
Economides et al., Cytokine traps: multi-component, high-affinity blockers of cytokine action Nature Med., 9:47-52 (2003).
Evans et al., "Mapping receptor binding sites in interleukin (IL)-1 receptor antagonist and IL-1 beta by site-directed mutagenesis. Identification of a single site in IL-1ra and two sites in IL-1 beta" J. Biol. Chem., 270:11477 (1995).
Fabre et al., "Binding sites for human interleukin 1alpha, gamma interferon and tumor necrosis factor on cultures fibroblasts of normal cornea and keratoconus", Curr. Eye. Res., 10:585-592 (1991).
Faour et al., "T-cell-derived interleukin-17 regulates the level and stability of cyclooxygenase-2 (COX-2) mRNA through restricted activation of the p38 mitogen-activated protein kinase cascade: role of distal sequences in the 3'-untranslated region of COX-2 mRNA." J. Biol. Chem., 278, 26897-26907, (2003).
Feldmann et al. "Chronic infantile neurological cutaneous and articular syndrome is caused by mutations in CIAS1, a gene highly expressed in polymorphonuclear cells and chondrocytes", Am J Hum Genet 71:198-203, (2002).
Ferry, et al, "Liver-Directed Gene Transfer Vectors" Hum. Gene Ther. 9:1975-81; (1998).
Ferry, et al, Hum. Gene Ther. 9:1975-81; (1998).
Fini et al., "Express of Collagenolytic | Gelatinolytic Metalloproteinases by Normal Cornea", Invest. Opthalmol. Vis. Sci., 31:1779-1788 (1990).
Finzel et al. Crystal Structure of Recombinant Human Interleukin-1? at 2.0 A Resolution, J. Mol. Biol. 209: 779-791, (1989).
Fisher et al., "Recombinant human interleukin | receptor antagonist in the treatment of patients with sepsis syndrome: results from a randomized, double-blind, placebo-controlled trial", JAMA., 271(23):1836-1843 (1994).
Fleischmann, et al. "Anakinra, a recombinant human interleukin-1 receptor antagonist (r-metHuIL-1ra), in patients with rheumatoid arthritis: A large, international, multicenter, placebo-controlled trial" Arthritis & Rheumatism 48, 927-34 (2003).
Fossiez et al., "T cell interleukin-17 induces stromal cells to produce proinflammatory and hematopoietic cytokines." J Exp Med. ;183(6):2593-603, Jun. 1, 1996.
Foulks et al., "Meibomian gland dysfunction: A clinical scheme for description, diagnosis, classification, and grading", Ocul. Suif., 1(3):107-126 (2003).
Freund et al. Upregulation of Nerve Growth Factor Expression by Human Airway Smooth Muscle Cells in Inflammatory Conditions. Eur. Resp. J. 20(2002):458-463.
Fu, Y.A., "Ocular manifestation of polychlorinated biphenyls intoxication", Am. J Ind. Med., 5: 127-132 (1984).
Fukushima et al., "Ag-specific recognition, activation, and effector function of T cells in the conjunctiva with experimental immune-mediated blepharoconjunctivitis", Invest. Opthalmol. Vis. Sci., 44:4366-4374 (2003).
Furfine, E.S., et al., "EBI-005: An IL-1 Receptor Inhibitor Designed for the Treatment of Dry Eye Syndrome," Retrieved from the Internet: URL:http://www.elevenbio.com/pdf/Eleven_poster_042312_lowres.pdf, pp. 1-1, (May 7, 2012) [Retrieved on Aug. 27, 2012].
Gabay et al., "Mouse IL-I receptor antagonist isoforms: complementary DNA cloning and protein expression of intracellular isoform and tissue distribution of secreted and intracellular IL-I receptor antagonist in vivo", J. Immunol., 159:5905-5913 (1997).
Galea, J., et al., "Intravenous anakinra can achieve experimentally effective concentrations in the central nervous system within a therapeutic time window: results of a dose-ranging study," Journal of Cerebral Blood Flow & Metabolism, 31(2):439-447 (2020) (Abstract).

(56) References Cited

OTHER PUBLICATIONS

Genovese et al, "LY2439821, a Humanized Anti-Interleukin-17 Monoclonal Antibody, in the Treatment of Patients with Rheumatoid Arthritis" Arthritis & Rheumatism (2010) 62(4):929-939.
Gerhardt et al, "Structure of IL-17A in complex with a potent, fully human neutralizing antibody." J. Mol. Biol. 394:905-921 (2009).
Ghetie et al., "Multiple roles for the major histocompatibility complex class I- related receptor FcRn." Ann. Rev. Immunol. 18:739-766 (2000)).
Gluzman et al., "SV40-transformed simian cells support the replication of early SV40 mutants." Cell 23:175, (1981).
Glynn et al., "Comparison of alternative regression models for paired binary data", Stat. Med., 13(10):1023-1036 (1994).
Goeddel et al., Direct expression in *Escherichia coli* of a DNA sequence coding for human growth hormone. Nature, 281:544 (1979).
Goeddel, "Synthesis of human fibroblast interferon by *E. coli*." Nucleic Acids Res., 8:4057 (1980).
Goto et al., "Impaired functional visual acuity of dry eye patients", Am. J. Opthalmol., 133:181-186 (2002).
Green et al., "Antigen-specific human monoclonal antibodies from mice engineered with human Ig heavy and light chain YACs." Nature Genetics 7:13-21 (1994).
Martin et al. "The affinity-selection of a minibody polypeptide inhibitor of human interleukin-6." EMBO J 13:5303-9 (1994).
Martinsen et al., "Alginate as immobilization material: I. Correlation between chemical and physical properties of alginate gel beads", Biotech. Bioeng., 33:79-89 (1989).
Mattheakis et al. "An in vitro polysome display system for identifying ligands from very large peptide libraries" Proc. Natl. Acad. Sci. USA 91:9022, (1994).
McDevitt et al., "Interleukin -1 genetic association with periodontitis in clinical practice", J. Periodontal. 71: 156-163 (2000).
McIndoe et al., "Localization of non-Mhc collagen-induced arthritis susceptibility loci in DBA/1j mice", Proc. Natl. Acad. Sci. USA, 96:2210-2214; (1999).
McMahan et al. "A novel IL-1 receptor, cloned from B cells by mammalian expression, is expressed in many cell types." EMBO J. 10: 2821, (1991).
Miljanovic et al., "Impact of dry eye syndrome on vision-related quality of life", Am. J. Opthalmol., 143:409-415 (2007).
Muller et al. "Corneal Nerves: Structure, Contents and Function." Exp. Eye Res. 76(2003):521-542.
Muller et al. "Ultrastructural Organization of Human Corneal Nerves." Invest. Opthalmol. Vis. Sci. 37.4(1996):476-488.
Needleman, et al "A general method applicable to the search for similarities in the amino acid sequence of two proteins" J. Mol. Biol. 48, 443-453, (1970).
Nuki, et al. "Long-term safety and maintenance of clinical improvement following treatment with anakinra (recombinant human interleukin-1 receptor antagonist) in patients with rheumatoid arthritis: Extension phase of a randomized, double-blind, placebo-controlled trial" <http://onlinelibrary.wiley.com/doi/10.1002/art.10578/abstract>Arthritis & Rheumatism 46, 2838-46 (2002).
O'Neill et al., "Signal transduction pathways activated by the IL-I receptor family: ancient signaling machinery in mammals, insects, and plants", J. Leukocyte Biol., 63:650-657 (1998).
Oka, et al. "Recent advances in liver-directed gene therapy: implications for the treatment of dyslipidemia <http://journals.lww.com/co-lipidology/Abstract/2000/04000/Recent_advances_in_liver_directed_gene_therapy_.11.aspx>" Curr. Opin. Lipidol. 11:179-86; (2000).
Okusawa et al., "Interleukin 1 induces a shock-like state in rabbits", J. Clin. Invest., 81: 1162-1172 (1988).
Olson et al. "Intravitreal Anakinra Inhibits Choroidal Neovascular Membrane Growth in a Rat Model" Ocul Immunol Inflamm 17(3):195-200, (2009).

Owyang et al. "XOMA 052, an Anti-IL-1? Monoclonal Antibody, Improves Glucose Control and ?-Cell Function in the Diet-Induced Obesity Mouse Model" Endocrinology, 151(6):2515-27, (2010).
Patel et al. "Interleukin-1 in the Brain." Ann. N.Y. Acad. Sci. 992(2003):39-47.
Pawliuk et al. "Systematic Genetic Analysis with Ordered Arrays of Yeast Deletion Mutants" Science 294:2368, (2001).
Pearson, "Comparison of methods for searching protein sequence databases", Protein Science 4, 1145-1160, (1995).
Pflugfelder et al., "Altered cytokine balance in the tear fluid and conjunctiva of patients with sjogren's yndrome keratoconjunctivitis sicca", Curr. Eye Res., 19:201-211 (1999).
Pflugfelder et al., "Conjuctival cytologic features of primary sjogren's syndrome", Ophthalmol., 97(8):985-991 (1990).
Pincus et al. "Assessment of Patient Satisfaction in Activities of Daily Living Using a Modified Stanford Health Assessment Questionnaire" Arthritis Rheum. 26(11):1346-53, (1983).
Pisella et al., "Flow Cytometric Analysis of Conjunctival Epithelium in Ocular Rosacea and Keratoconjunctivitis Sicca", Opthalmol., 107:1841-1849 (2000).
Quartier et al. "Extended report: A multicentre, randomised, double-blind, placebo-controlled trial with the interleukin-1 receptor antagonist anakinra in patients with systemic-onset juvenile idiopathic arthritis" Ann Rheum Dis. 70(5):747-54, (2011).
Reiff, A., "The use of anakinra in juvenile arthritis", Curr. Rheumatol. Rep., 7:434-440 (2005).
Relton, J.K., et al., "Interleukin-1 Receptor Antagonist Inhibits Ischaemic and Excitotoxic Neuronal Damage in the Rat," Brain Research Bulletin, 29(2):243-246 (1992) (Abstract).
Rice, P. et al., "Emboss: The European Molecular Biology Open Software Suite" Trends in Genetics, 16, (6) pp. 276-277, (2000).
Riechmann et al., "Reshaping human antibodies for therapy" Nature 332, 323-327, 1988.
Rosenbaum et al., "Detection of mRNA for the Cytokines, Interleukin-1 alpha and interleukin-8, in corneas from patients with pseudophakic bullous keratopathy", Invest. Opthalmol. Vis. Sci., 36:2151-2155 (1995).
Rosner et al.' "Incorporation of clustering effects for the Wilcoxon rank sum test: A Large-Sample Approach", Biometrics, 59(4):1089-1098 (2003).
Rothwell, et al., "Interleukin 1 in the brain: biology, pathology and therapeutic target" TINS 23(12): 618-625, (2000).
Sall et al., "Two multicenter, randomized studies of Efficacy and safety of cyclosporine ophthalmic emulsion in moderate to severe dry eye disease", Ophthalmol., 107:631-639 (2000).
Schaffitzel et al. "Ribosome display: an in vitro method for selection and evolution of antibodies from libraries." (1999).
Schiff, et al. "The safety of anakinra in high-risk patients with active rheumatoid arthritis: six-month observations of patients with comorbid conditions" Arthritis & Rheumatism 50, 1752-60 (2004).
Schiffinan et al., "Reliability and Validity of the Ocular Surface Disease index", Arch. Ophthalmol., 118:615-621 (2000).
Schreuder et al., A new cytokine-receptor binding mode revealed by the crystal structure of the IL-1 receptor with an antagonist Nature 386: 194-200, (1997).
Shields et al., "High resolution mapping of the binding site on human IgG1 for Fc gamma RI, Fc gamma RII, Fc gamma RIII, and FcRn and design of IgG1 variants with improved binding to the Fc gamma R." J. Biol. Chem. 276:6591-6604 (2001).
Shimazaki et al., "Meibomian gland dysfunction in patients with sjogren syndrome", Opthalmol., 105:1485-1488 (1998).
Shiratory, et al. "Strategy of liver-directed gene therapy: present status and future prospects." Liver 19:265-74; (1999).
Siemion, I.Z., et al., "Anti-IL-1 Activity of Peptide Fragments of IL-1 Family Proteins," Peptides, 19(2):373-382 (1998).
Sims , et al., "The IL-1 family: regulators of immunity, Nature Reviews Immunology" Nat Rev Immunol. <http://www.ncbi.nlm.nih.gov/pubmed/20081871> 10(2):89-102, (Feb. 2010).
Sjolander, et al., "Integrated fluid handling system for biomolecular interaction analysis", Anal. Chem. 63:2338-2345, (1991).
Smith "Filamentous fusion phage: novel expression vectors that display cloned antigens on the virion surface." Science 228:1315-1317, (1985).

(56) References Cited

OTHER PUBLICATIONS

Smith et al., "Doxycycline-a role in ocular surface repair", Br. J. Ophthalmol., 88:619-625 (2004).
Smith-Arica, et al. "Gene therapy: recombinant adeno-associated virus vectors." Curr. Cardiol. Rep. 3:43-49; (2001).
Solomon et al., "Doxycycline inhibition of interleukin-1 in the corneal epithelium", Invest. Opthalmol. Vis. Sci., 41:2544-2557 (2000).
Solomon et al., "Pro- and Anti-imflammatory forms of interleukin-1 in the tear fluid and conjunctiva of patients with dry-eye disease", Invent. Opthalmol. Vis. Sci., 42:2283-2292 (2001).
Stevenson et al., "Efficacy and safety of cyclosporine a ophthalmic emulsion in the treatment of moderate-to-severe dry eye disease", Opthalmol., 107(5):967-974 (2000).
Szabo et al., "Surface plasmon resonance and its use in biomolecular interaction analysis (BIA).", Curr. Opin. Struct. Biol. 5:699-705, (1995).
Temporin et al. "Interleukin-1 Beta Promotes Sensory Nerve Regeneration after Sciatic Nerve Injury." Neurosci. Lett. 440.2(2008):130-133.
Greenfeder et al., "Insertion of a Structural Domain of Interleukin (IL)-1? Confers Agonist Activity to the IL-1 Receptor Antagonist Implications for IL-1 Bioactivity" J. Biol. Chem., 270:22460 (1995).
Guenard et al. "Peripheral Nerve Regeneration is Impended by Interleukin-1 Receptor Antagonist Released from a Polymeric Guidance Channel." J. Neurosci. Res. 29(1991):396-400.
Hanes et al. "Picomolar affinity antibodies from a fully synthetic naive library selected and evolved by ribosome display" Nat Biotechnol. 18:1287-92, (2000).
Hanes et al. "Selecting and evolving functional proteins in vitro by ribosome display" Methods Enzymol. 328:404-30; (2000).
Hassan et al. "Increased Susceptibility to Dextran Sulfate Sodium Induced Colitis in the T Cell Protein Tyrosine Phosphatase Heterozygous Mouse" PLoS One.;5(1):e8868 (Jan. 25, 2010).
He et al. "High throughput thermostability screening of monoclonal antibody formulations" J. Pharm. Sciences, 99 1707-1720, (2010).
Heidary et al: Long-Range Coupling 1-70 Between Separate Docking Sites in Interleukin-1β, Journal of Molecular Biology, Academic Press, United Kingdom, Vol. 353, No. 5, Nov. 11, 2005.
Hess et al., "Cooperation of glycolytic enzymes" J. Adv. Enzyme Reg., 7:149 (1968).
Higgins et al., "Using Clustal for multiple sequence alignments", Methods Enzymol. 266, 383-402, (1996).
Hinton, "Engineered Human IgG Antibodies with Longer Serum Half-lives in Primates" J. Biol. Chem. 279:6213-6216 (2004).
Hirano et al., "Usefulness of CD4+CD45RBhigh CD25? Cell-Transferred SCID Mice for Preclinical Evaluation of Drugs for Inflammatory Bowel Disease" J Pharmacol Sci.;110(2):169-81, (Jun. 2009).
Hitzeman et al., "Isolation and characterization of the yeast 3-phosphoglycerokinase gene (PGK) by an immunological screening technique." J. Biol. Chem., 255:2073 (1980).
Hoffman et al. "Mutation of a new gene encoding a putative pyrin-like protein causes familial cold autoinflammatory syndrome and Muckle-Wells syndrome" Nature 29:301-305 (2001).
Hoffman et al: "Efficacy and safety of rilonacept (interleukin-I trap) in patients with cryopyrin-associated periodic syndromes: Results from two sequential placebo-controlled studies", Arthritis & Rheumatism, vol. 58, No. 8, Jul. 30, 2008, pp. 2443-2452.
Holland et al, "Isolation and identification of yeast messenger ribonucleic acids coding for enolase, glyceraldehyde-3-phosphate dehydrogenase, and phosphoglycerate kinase <http://pubs.acs.org/doi/abs/10.1021/bi00616a007>" Biochemistry, 17:4900 (1978).
Holliger et al. ""Diabodies": small bivalent and bispecific antibody fragments." Proc Natl Acad Sci USA 90:6444-6448 (1993).
Hosse et al., "A new generation of protein display scaffolds for molecular recognition." Protein Science, 15:14-27 (2006).
Hou, et al., "Design of a superior cytokine antagonist for topical ophthalmic use" Eleven Biotheraputics,Inc., PNAS, vol. 110, No. 10, P. 3913-3918, Mar. 5, 2013.
Hynninen et al., "Interleukin 1 receptor antagonist and E-selectin concentrations: A comparison in patients with severe acute pancreatitis and severe sepsis", J. Crit Care., 14(2):63-68 (1999).
Ill et al, "Design and construction of a hybrid immunoglobulin domain with properties of both heavy and light chain variable regions" Protein Engineering (1997)10(8):949-957.
Imren et al. "Permanent and panerythroid correction of murine_ thalassemia by multiple lentiviral integration in hematopoietic stem cells" PNAS 99:14380, (2002).
Inaba et al., "Expression of the antimicrobial peptide alpha-defensin/cryptdins in intestinal crypts decreases at the initial phase of intestinal inflammation in a model of inflammatory bowel disease, IL-10-deficient mice." Inflamm Bowel Dis.,16(9):1488-95 (Sep. 2010).
International Preliminary Report on Patentability and Written Opinion for PCT/US2012/022583 date Jul. 30, 2013.
International Preliminary Report on Patentability and Written Opinion for PCT/US2012/048631 dated Feb. 4, 2014.
International Preliminary Report on Patentability and Written Opinion, International Application No. PCT/US2011/041588, mailed on Dec. 28, 2012.
International Preliminary Report on Patentability and Written Opinion, International Application No. PCT/US2011/045995, mailed on Jan. 29, 2013.
International Preliminary Report on Patentability and Written Opinion, International Application No. PCT/US2012/048631, Date of Issuance of Report Feb. 4, 2014.
International Search Report and Written Opinion for PCTUS2014026416 dated Jul. 17, 2014.
International Search Report for PCT/US08/09776, mailed Feb. 26, 2009.
International Search Report for PCT/US2011/045995 dated Dec. 23, 2011.
International Search Report for PCT/US2012/022583 dated Jun. 9, 2012.
International Search Report for PCT/US2012/048631 dated Jan. 23, 2013.
International Search Report, International Application No. PCT/US2010/020646, mailed on Oct. 8, 2010.
International Search Report, International Application No. PCT/US2012/048631, mailing date Jan. 23, 2013.
Issekutz, et al., "Treatment of established adjuvant arthritis in rats with monoclonal antibody to CD18 and very late activation antigen-4 integrins suppresses neutrophil and T-lymphocyte migration to the joints and improves clinical disease" Immunology 88:569 (1996).
Janssens et al, "Generation of heavy-chain-only antibodies in mice" PNAS (2006) 103(41):15130-15135.
Jie et al. "Interleukin-1 Receptor Antagonist Eye Drops Promoting High-Risk Corneal Allografts Survival in Rats." Ch. Med. J.117. 5(2004):711-716.
Jones et al., "Sjogren's syndrome: Cytokine and Epstein- Barr viral gene expression within the Conjunctival Epithelium", Invest. Ophtalmo/. Vis. Sci., 35(9):3493-3503 (1994).
Karlin et al., "Applications and statistics for multiple high-scoring segments in molecular sequences", PNAS USA 90, 5873-5787, (1993).
Kay, "Adenoviral Vectors for Hepatic Gene Transfer in Animals" Chest 111(6 Supp.):138S-142S, (1997).
Keane-Myers et al. "Prevention of Allergic Eye Disease by Treatment with IL-1 Receptor Antagonist" Invest Ophthalmol Vis Sci, 40(12): 3041-6, (1999).
Kluczyk A., et al., "Immunodulatory Activity of Oligopeptides Related to Interleukin 1 Receptor Antagonist Sequence," Arch. Immunol. Ther. Exp., 45(5-6):427-433 (1997).
Kluczyk, A., et al., "The two-headed peptide inhibitors of interleukin-1 action," Peptides, 21(9):1411-1420 (2000) (Abstract).
Kocak-Altintas et al., "Impression cytology and ocular characteristics in ocular rosacea", Eur. J. Opthalmol., 13:351-359 (2003).

(56) References Cited

OTHER PUBLICATIONS

Krelin et al. "Interleukin-1b-Driven Inflammation Promotes the Development and Invasiveness of Chemical Carcinogen—Induced Tumors" Cancer Res. 67:1062-1071, (2007).

Larsen, et al. "Interleukin-1-Receptor Antagonist in Type 2 Diabetes Mellitus" NEJM 356:1517-26, (2007).

Larsen, et al. "Sustained Effects of Interleukin-1 Receptor Antagonist Treatment in Type 2 Diabetes" Diabetes Care 32:1663-8, (2009).

Lee, et al. "Remission in models of type 1 diabetes by gene therapy using a single-chain insulin analogue." Nature 408:483-8 (2000).

Lust et al. "Induction of a Chronic Disease State in Patients With Smoldering or Indolent Multiple Myeloma by Targeting Interleukin 1?-Induced Interleukin 6 Production and the Myeloma Proliferative Component" Mayo Clin Proc 84(2):114-122, (2009).

Macsai. "The Role of Omega-3 Dietary Supplementation in Blephartitis and Meibomian Gland Dysfunction (an AOS Thesis)." Transactions of the American Ophthalmological Society. 106(2008):336-356.

 
 
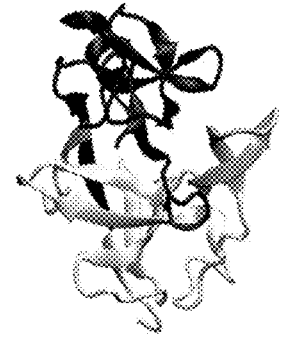 
FIG. 3

FIG. 5A: P01

APVRSLAFRIWDVNQKTFYLRNNQLVAGYLQGPNVN
LEEKIDV*SFVQGEESNDKIPVALG*IHGGKMCLSCVK
SGDETRLQLEAV*DPKNYPKKKM*DKRFAFIRSDSGPT
TSFESAACPGWFLCTAMEADQPVSLTNMPDEGVMVT
KFY*MQFVSS*    (SEQ ID NO:17)

FIG. 5B: P02

APVRSLAFRIWDVNQKTFYLRNNQLVAGYLQGPNVN
LEEKIDV*SFVQGEESNDKIPVALG*IHGGKMCLSCVK
SGDETRLQLEAV***DPKNYPKKKMEKRFVFNKIEINNK
L***SFESAACPGWFLCTAMEADQPVSLTNMPDEGVMVT
KFY*MQFVSS*    (SEQ ID NO:18)

FIG. 5C: P03

APVRSLAFRIWDVNQKTFYLRNNQLVAGYLQGPNVN
LEEK***FSMSFVQGEESNDKIPVALGLKEKNLYLSCVL
KDDKPTLQLESVDPKNYPKKKMEKRFVF***IRSDSGPT
TSFESAACPGWFLCTAMEADQPVSLTNMPDEGVMVT
K*FTMQFVSS*    (SEQ ID NO:19)

FIG. 5D: P04

*APVRSL*AFRIWDVNQKTFYLRNNQLVAGYLQGPNVNLEE
K*FSMSFVQGEESNDKIPVALGLKEKNLYLSCVLKDDKPTL*
*QLESVDPKNYPKKKMEKRFVFNKIEINNKLEFES*AACPG
WFLCTAMEADQPVSLTNMPDEGVMVTK*FTMQFVSS*
(SEQ ID NO:20)

FIG. 5E: P05

*APVRSLN*CRIWDVNQKTFYLRNNQLVAGYLQGPNVNLEE
K*FSMSFVQGEESNDKIPVALGLKEKNLYLSCVLKDDKPTL*
*QLESVDPKNYPKKKMEKRFVFNKIEINNKLEFESAQFPN*
*W*FLCTAMEADQPVSLTNMPDEGVMVTKFY*MQFVSS*
(SEQ ID NO:21)

NUCLEIC ACID ENCODING CHIMERIC IL-1 RECEPTOR TYPE I ANTAGONISTS

CROSS-REFERENCE AND CLAIM OF PRIORITY

This application is a divisional of U.S. application Ser. No. 13/812,582 filed on Jul. 29, 2011 and issued as U.S. Pat. No. 8,853,150, which is a national phase application under 35 U.S.C. §371 of PCT International Application No. PCT/US2011/045995, filed Jul. 29, 2011, which claims priority to U.S. provisional patent application Ser. No. 61/368,799, filed Jul. 29, 2010, Ser. No. 61/436,178, filed Jan. 25, 2011, Ser. No. 61/436,184, filed Jan. 25, 2011, Ser. No. 61/493,966, filed Jun. 6, 2011, and Ser. No. 61/493,967, filed Jun. 6, 2011. The contents of U.S. application Ser. No. 13/812,582 filed on Jul. 29, 2011; International Application No. PCT/US2011/045995, filed Jul. 29, 2011; and U.S. provisional applications Ser. No. 61/368,799, filed Jul. 29, 2010, Ser. No. 61/436,184, filed Jan. 25, 2011, and Ser. No. 61/493,967, filed Jun. 6, 2011, are incorporated herein by reference.

BACKGROUND

Interleukin-1 alpha (IL-1α) and beta (IL-1β) are prototypic members of a family of immunoregulatory cytokines and have several prominent roles in regulating the immune system. IL-1α and IL-1β bind to the interleukin-1 receptor I (IL-1RI), leading to the engagement of the secondary receptor, interleukin-1 receptor accessory protein (IL-1RAcP). Signaling agonized by IL-1α and IL-1β leads to amplified T cell responses, including the proliferation and survival of naïve T cells and the development of $T_H17$ cells.

SUMMARY

Featured herein are non-naturally occurring cytokine domains that can be used, inter alia, to modulate cellular signalling responsive to interleukin-1 receptor I (IL-1RI), to treat disorders, and to detect and/or bind to cellular receptors, as well as other agents.

In one aspect, this disclosure features an isolated protein including an cytokine domain that contains amino acid residues from at least two parental cytokines domains, for example, receptor binding features, surface features, β strands, and loops from at least two parental cytokines domains.

In some embodiments, the cytokine domain binds to IL-1RI and includes receptor binding features from different parental cytokine domains, e.g., from a receptor agonist and a receptor antagonist (such as IL-1β and IL-1Ra, or IL-1α and IL-1Ra), from IL-1β and IL-1α, or from all three of IL-1Ra, IL-1α and IL-1Ra. The receptor binding features can correspond to residues, segments, or regions in Sites A and B. With respect to such residues, segments, and regions corresponding to Sites A and B, in the context of IL-1 (IL-1β, IL-1α, and IL-1Ra), see the definitions further below.

With respect to Site A, the cytokine domain may have: (a)(i) Site A residues that are at least 60, 70, 80, 85, 88, 90, 92, 95, 98, or 100% identical to corresponding residues in a first parental cytokine domain; (a)(ii) Extended Site A residues that are at least 60, 70, 80, 85, 88, 90, 92, 95, 98, or 100% identical to corresponding residues in a first parental cytokine domain; (a)(iii) Site A segments A1 and A2 that are at least 80, 85, 88, 90, 92, 95, or 100% identical to corresponding regions of a first parental cytokine domain; and/or (a)(iv) a Site A region that is at least 80, 85, 88, 90, 92, 95, or 100% identical to corresponding regions of a first parental cytokine domain.

With respect to Site B, the cytokine domain may have: (b)(i) Site B residues that are at least 60, 70, 80, 85, 88, 90, 92, 95, 98, or 100% identical to corresponding residues in a second parental cytokine domain; (b)(ii) extended Site Bs residues that are at least 60, 70, 80, 85, 88, 90, 92, 95, 98, or 100% identical to corresponding residues in a second parental cytokine domain; (b)(iii) Site B segments B1, B2, and B3 that are at least 80, 85, 88, 90, 92, 95, or 100% identical to corresponding regions of a second parental cytokine domain; and/or (b)(iv) a Site B region that is at least 80, 85, 88, 90, 92, 95, or 100% identical to corresponding regions of a second parental cytokine domain.

In some embodiments, the cytokine domain includes features: (a)(i) and b(i), (a)(ii) and b(ii), (a)(iii) and (b)(iii), or (a)(iv) and (b)(iv), e.g., wherein each feature is further defined by 80, 85, 88, 90, 92, 95, or 100% identity. For example, the first parental cytokine domain can be IL-1β, and the second parental cytokine domain can be IL-1Ra. For example, the first parental cytokine domain can be IL-1α, and the second parental cytokine domain can be IL-1Ra.

The cytokine domain can also include amino acids from a second parental cytokine domain at one or more positions in the domain that impair interaction with a cytokine secondary receptor (e.g., IL-1RAcP). For example, the second parental cytokine domain is IL-1Ra. In some embodiments, the cytokine domain includes one or more Site C and/or D segments (e.g., C1, D1, D2, D3, D4, and/or D5) from IL-1Ra, or sequences at least 80, 85, 88, 90, 92, 95, or 100% identical to such segments. For example, the cytokine domain includes (i) a Site C residues that are at least 60, 70, 80, 85, 88, 90, 92, 95, 98, or 100% identical to corresponding residues in IL-1Ra, (ii) Site D residues that are at least 60, 70, 80, 85, 88, 90, 92, 95, 98, or 100% identical to corresponding residues in IL-1Ra, (iii) a C1 segment that is at least 70, 75, 80, 85, 88, 90, 92, 95, 98, or 100% identical to corresponding residues in IL-1Ra; or (iv) a D2 segment that is identical at at least 3, 4, or 5 residues to corresponding residues in IL-1Ra. The cytokine domain can include features (i) and (ii), or (ii) and (iii), e.g., wherein each feature is further defined by 80, 85, 88, 90, 92, 95, or 100% identity, or (iii) and (iv)

The domain can include regions from at least two different human IL-1 family cytokine domains, wherein the regions are selected from the group consisting of the A region (having A1 and A2 segments), the B region (having B1, B2, and B3 segments), the C region, and the D region (having D1, D2, D3, D4, and D5 segments).

The cytokine domain can include a Site A region and a Site B region from different cytokine domains. The Site A region can be from a naturally occurring receptor agonist or antagonist; the Site B region can be from a naturally occurring receptor agonist. It can include a Site C region from a naturally occurring receptor antagonist and/or a Site D region from a naturally occurring receptor antagonist.

For example, the domain can be a chimeric domain having segments that are at least 5, 6, 10, 15, 20, or 25 amino acids in length and that are at least 80, 85, 88, 90, 92, 95, or 100% identical to corresponding segments from at least two different parental cytokine domains, such as a first and second parental cytokine domain. The parental cytokine domains can be IL-1RI binding cytokines, such as IL-1β, IL-1α, and IL-1Ra. In some embodiments, the amino acids that are not in the segments from the first parental cytokine domain are from two or more other parental cytokine domains.

In some embodiments, the cytokine domain includes at least two segments of at least 5, 6, 10, 15, 20, or 25 amino acids in length that are at least 80, 85, 88, 90, 92, 95, or 100% identical to corresponding segments of a first parental cytokine domains, and the amino acids that are not in such segments are predominantly (e.g., at least 50, 60, 70, 80, 85, 88, 90, 92, 95, or 100%) identical to corresponding residues in the second parental cytokine domain.

In some embodiments, the cytokine domain includes (i) at least two segments of at least 5, 6, 10, 15, 20, or 25 amino acids in length that are at least 80, 85, 88, 90, 92, 95, or 100% identical to corresponding segments of a first parental cytokine domains, and (ii) at least one, two or three segments, e.g., of at least 5, 6, 7, 8, 10, or 15 amino acids in length, that are identical to a second parental cytokine domain.

For example, the cytokine domain can include a first segment of 20-50, 25-50, 30-45, or 30-40 amino acids (e.g., 29, 30, 31, 32, 33, 34, 35, 36, 37, 38, 39, or 40), and a second segment of 20-45, 20-40, 25-40, or 25-35 amino acids (e.g., 25, 26, 27, 28, 29, 30, 31, 32, 33, 34, or 35), each identical (or at least 80, 85, 88, 90, 92, 95, or 98% identical) to a first parental cytokine domain (e.g., IL-1Ra), and a third segment that is identical (or at least 80, 85, 88, 90, 92, 95, or 98% identical) to a second parental cytokine domain (e.g., IL-1β or IL-1α). For example, the third segment can be between 55-90, 60-90, 60-85, or 70-85 amino acids in length, e.g., 75, 76, 77, 78, 79, 80, 81, 82, 83, 84, or 85 amino acids in length.

In some embodiments: the first segment can be a segment at least 80, 85, 88, 90, 92, 95, 98, or 100% to WDVNQKTFYLRNNQLVAGYLQGPNV (SEQ ID NO:9, also termed the A1 segment herein, and corresponding to residues 16-40 of SEQ ID NO:3 and residues 11-36 according to IL-1β numbering). The second segment can be a segment at least 80, 85, 88, 90, 92, 95, 98, or 100% to residues 120-140 or 120-141 of SEQ ID NO:3 (IL-1Ra), corresponding to residues 121-139 or 121-140 (according to IL-1β numbering). The third segment can be at least 80, 85, 88, 90, 92, 95, 98, or 100% to residues 45-100 or 42-120 from IL-1β (SEQ ID NO:1).

In some cases, the first segment can be a segment at least 80, 85, 88, 90, 92, 95, 98, or 100% to residues 14-45 of SEQ ID NO:3 (corresponding to residues 9-41 according to IL-1β numbering). The second segment can be a segment at least 80, 85, 88, 90, 92, 95, 98, or 100% to residues 120-145 of SEQ ID NO:3 (corresponding to residues 121-145 according to IL-1β numbering) or residues 120-147 of SEQ ID NO:3 (corresponding to residues 121-147 according to IL-1β numbering). In some embodiments, at least residues 11-41 and 120-147 (according to IL-1β numbering) are collectively at least 80, 85, 88, 90, 92, 95, 98, or 100% identical to corresponding residues in IL-1Ra.

In some embodiments, a terminus of one of the segments of the first IL-1 family cytokine domain is located within five, four, three, two, or one amino acids of amino acid 41 of SEQ ID NO:1 and a terminus of one of the segments of the first IL-1 family cytokine domain is located within five, four, three, two, or one amino acids of amino acid 121 of SEQ ID NO:1.

In some embodiments, the domain includes a segment having an N-terminus at a position within five, four, three, two, or one amino acids of amino acid 42 of SEQ ID NO:1 and a C-terminus within five, four, three, two, or one amino acids of amino acid 120 of SEQ ID NO:1, and/or a segment having an N-terminus at a position within five, four, three, two, or one amino acids of amino acid 121 of SEQ ID NO:1 and a C-terminus within five, four, three, two, or one amino acids of amino acid 145 of SEQ ID NO:1. In some embodiments, residues in the domain at positions corresponding to 11-41 and 120-147 (according to IL-16 numbering) are collectively at least 80, 85, 88, 90, 92, 95, 98, or 100% identical to corresponding residues in IL-1Ra. The domain can also be based on sequences from IL-1 cytokine family members, e.g., at analogous positions to the foregoing.

In some embodiments, the cytokine domain includes one, two, three or more of the following sequences: WDVNQKTFYLRNNQLVAGYLQGPNV (SEQ ID NO:9); NLEEK (SEQ ID NO:10); RIWDVNQKTFYLRNNQLVAGYLQGPNVNLEEK(SEQ ID NO:11); AMEADQP(SEQ ID NO:12); FLCTAMEADQPVSLTNMPDEGVMVTKFY (SEQ ID NO:13); and/or sequences at least 80, 85, 88, 90, 92, 95, 98, or 100% identical to the foregoing. In some embodiments, the cytokine domain includes one, two, three or more of the following sequences: VQGEESNDKI (SEQ ID NO:14); KKKMEKRF (SEQ ID NO:15); and FSMSFVQGEESNDKIPVALGLKEKNLYLSCVLKDDKPTLQLESVDPKN YPKKKMEKRFVFNKIEINNKLEFES (SEQ ID NO:16); and/or sequences at least 80, 85, 88, 90, 92, 95, 98, or 100% identical to the foregoing.

In some embodiments, one or more or all of the β1β2, β2β3, β8β9 and β10β11 loops are at least 80, 85, 88, 90, 92, 95, or 100% identical to corresponding loops from an IL-1 antagonist, e.g., IL-1Ra. In some embodiments, one or more or all of the β4β5, β5β6, β6β7 and β7β8 loops are at least 80, 85, 88, 90, 92, 95, or 100% identical to corresponding loops from a different IL-1 family cytokine domain than the human parental cytokine that is most similar to the β1β2, β2β3, β8β9 and β10β11 loops. For example, one or more or all of the β4β5, β5β6, β6β7 and β7β8 loops are at least 80, 85, 88, 90, 92, 95, or 100% identical to such loops from an IL-1 agonist such as IL-1β. In some embodiments, the β11β12 loop is at least 80, 85, 88, 90, 92, 95, or 100% identical to corresponding loop from an IL-1 antagonist, e.g., IL-1Ra.

In some embodiments, the cytokine domain includes sequences that are at least 80, 85, 88, 90, 92, 95, or 100% identical to one, two, three, or all of beta strands β2, β3, β10 and β11 of IL-1Ra. In some embodiments, the cytokine domain includes sequences that are at least 80, 85, 88, 90, 92, 95, or 100% identical to one, two, three, or all of β4, β6, β7, and β8 of IL-1β, or to β4, β5, β6, β7, and β8 of IL-1β.

In some embodiments, the cytokine domain does not contain a segment that is greater than 80, 85, 90, 95, or 100% identical to amino acids I46-G59, A55-G59, A55-V83, I60-V83, N84-D95, I46-S110, V49-S110, or I46-G118 of SEQ ID NO:3. In some embodiments, the cytokine domain does not contain a segment that is greater than 80, 85, 90, 95, or 100% identical to amino acids N7-V41, R11-M36, N102-D145, or Y121-D145 of SEQ ID NO:1.

Generally, the cytokine domain is not naturally occurring. It differs from human IL-1 family cytokine domains. For example, it is less than 98, 95, 90, 85, 80, 75, 70, 65, 60, or 55% identical to IL-1Ra (SEQ ID NO:3), IL-1β (SEQ ID NO:1), and/or IL-1α (SEQ ID NO:2). The cytokine domain can also be at least 30, 40, 45, 50, 55, 60, 65, 70% identical to such cytokine. For example, the chimeric domain can be between 30-95%, 40-90%, or 45-85% identical to IL-1Ra, IL-1β, and IL-1α. For example, the chimeric domain can be between 40-90% identical to IL-1β and 35-85% identical to IL-1Ra; between 40-80% identical to IL-1β and 45-80% identical to IL-1Ra; between 45-72% identical to IL-1β and 45-80% identical to IL-1Ra; between 45-72% identical to IL-1β and 53-80% identical to IL-1Ra; between 50-72% identical to IL-1β and 53-70% identical to IL-1Ra; between 60-72% identical to IL-1β and 53-68% identical to IL-1Ra; between 65-72% identical to IL-1β and 54-60% identical to IL-1Ra; or between 68-72% identical to IL-1β and 54-57% identical to IL-1Ra. For example, the chimeric domain can be between 40-90% identical to IL-1α and 35-85% identical to IL-1Ra; between 40-80% identical to IL-1α and 45-80% identical to IL-1Ra; between 45-72% identical to IL-1α and 45-80% identical to IL-1Ra; between 45-72% identical to IL-1α and 53-80% identical to IL-1Ra; between 50-72% identical to IL-1a and 53-70% identical to IL-1Ra; between 60-72% identical to IL-1α and 53-68% identical to IL-1Ra; between 65-72% identical to IL-1α and 54-60% identical to IL-1Ra; or between 68-72% identical to IL-1α and 54-57% identical to IL-1Ra.

In some embodiments, the cytokine domain differs from IL-1Ra, and binds to the receptor while including a Site C and/or Site D characteristic of a naturally occurring receptor antagonist (such as IL-1Ra). For example, the domain is less than 98, 95, 92, 90, 85, and 80% identical from human IL-1β and/IL-1Ra. For example, the domain is between 40-95%, 40-90% or 45-85% identical to IL-1Ra. The domain can also be between 40-95%, 40-90% or 45-85% to an IL-1 family cytokine agonist, such as IL-1α or IL-1β. In some embodiments, the cytokine domain includes: at least 40, 45, 50, 55, 60, 65, 70, 75, 80 or 85% amino acids from a first parental cytokine domain that is an agonist of cytokine signaling.

In some embodiments, the cytokine domain has greater amino acid identity (e.g., at least 5, 10, 15, or 20% greater) to a receptor agonist (such as IL-1β or IL-1α) than to a receptor antagonist (IL-1Ra), but functions as an antagonist of IL-1RI.

In some embodiments, the cytokine domain is completely chimeric, e.g., each amino acid in the domain is from one of the parental cytokine domains, e.g., one of two parental cytokine domains or one of three or more parental cytokine domains. For example, the parental cytokine domains are human cytokine domains or non-human primate cytokine domains. In some embodiments, the cytokine domain is partially chimeric, e.g., not all amino acids in the domain are from one of the parental cytokine domains.

For example, the isolated protein binds to IL-1RI and modulates signaling by the receptor, e.g., agonizes or antagonizes IL-1RI receptor signaling activity. In some embodiments, the protein does not substantially induce IL-6 production when contacted to IL-1β responsive human cells and/or does not substantially induce production of an IL-1β responsive reporter gene, e.g., at concentrations of 10 μg/ml, 100 μg/ml, or 1 mg/ml. Generally, the protein inhibits signaling by IL-1β (e.g., at a concentration of 0.1 ng/ml such as in a cellular assay described herein) with an IC50 of less than 100, 50, 20, 10, or 5 nM. The protein can inhibit signaling by IL-1β with an IC50 that is less than that of IL-1Ra, e.g., at least 10, 20, or 50% lower.

In certain embodiments, the cytokine domain binds to e.g., with the same or better affinity than one of the parental cytokine domains. In some embodiments, the cytokine domain binds to IL-1RI with $K_D$ of less than 100, 50, 20, 10, 5, or 1 nM, or less than 500, 400, 100, or 50 μM. For example, the association constant can be greater than $1\times10^4$, $3\times10^4$, $1\times10^5$, or $1\times10^6$ $M^{-1}$ $s^{-1}$, and the dissociation can be less than $1\times10^{-3}$, $1\times10^{-4}$, $6\times10^{-4}$, or $6\times10^{-6}$ $s^{-1}$.

In some embodiments, the cytokine domain binds to IL-1RI with a better affinity (e.g., lower $K_D$) and/or a slower dissociation rate than IL-1β or IL-1Ra. For example, the cytokine domain can bind to IL-1RI with a dissociation constant less than or equal to that of IL-1Ra and/or with an association constant greater or equal to that of IL-1β.

The cytokine domain can be between approximately 120-180, 140-170, or 148-160, or 150-156 amino acids in length. In some embodiments, the domain is 152 or 153 amino acids in length. Typically the domain includes at least 10, 11, or 12β-strands, and is stably folded. In some embodiments, the cytokine domain has a Tm of at least 38, 40, 42, 44, 46, 48, 50, 52, 54, 56, 58, 60, 62, or 64° C., as described herein. It can have a Tm of between 51-61, 51-66, 56-61, or 56-66° C. In some embodiments, the cytokine domain does not begin unfolding until at least 48, 50, 51, 55, 57, 58, or 59° C. For example, it has a Tm that is at least within 10° C. or 5° C. of the Tm of IL-1Ra and/or IL-1β in a physiological buffer. In some embodiments, it is more thermostable than IL-1Ra and/or IL-1β in a physiological buffer. For example the domain can have a Tm that is at least 2, 4, 6, 7, or 8° C. greater than the Tm of IL-1Ra and/or IL-1β in a physiological buffer, e.g., between about 5-12, 5-10, or 7-10° C. greater than the Tm of IL-1Ra and/or IL-1β at a concentration of about 0.5 mg/ml.

The protein can include other features described herein.

In another aspect, the disclosure features an isolated protein that includes a chimeric IL-1 family cytokine domain. Examples of IL-1 cytokine family members include IL-1α, IL-1β, IL-1Ra, IL-18, IL-1F5, IL-1F6, IL-1F7, IL-1F8, IL-1F9, IL-1F10, and IL-33. The cytokine domain can include a receptor binding region of one of the foregoing cytokines or a protein sequence that includes elements of one or more such cytokines. For example, the cytokine domain can include a chimera of two or more IL-1 cytokine family members.

In one embodiment, the chimeric domain includes at least one segment of length at least five, six, seven, eight, nine, ten, 15, 20, 25, 30, 35, 40, 45, 50, 55, 60, 65, or 70 amino acids and having amino acid identity to (or at least 80, 82, 85, 87, 90, 92, 94, 95, 96, 97, 98, or 99% identity to) to a first IL-1 family cytokine, and another segment of length of length at least five, six, seven, eight, nine, ten, 15, 20, 25, 30, 35, or 40 amino acids and having amino acid identity to (or at least 80, 82, 85, 87, 90, 92, 94, 95, 96, 97, 98, or 99% identity to) to a second IL-1 family cytokine. The chimeric domain can be less than 90, 85, 80, or 75% identical to one or both of the first and second IL-1 family cytokine.

In one embodiment, the first and second IL-1 family cytokines are selected from the group consisting of IL-1β, IL-1α, and IL-1Ra. In another embodiment, the first and second IL-1 family cytokines are selected from the group consisting of IL-1F5, IL-1F6, IL-1F7, and IL-1F8. In another embodiment, the first IL-1 family cytokine is selected from the group of agonists and the second is selected from the group of antagonists. In some embodiments, the chimeric domain includes fewer than 120, 110, 100, 90, or 80 contiguous amino acids from the same parental cytokine domain.

In one embodiment, the chimeric domain is identical to the first IL-1 family cytokine at at least 50, 60, 70, 80, 90, 100, 110, or 120 positions and is identical to the second IL-1 family cytokine at at least 50, 60, 70, 80, 90, 100, 110, or 120 positions (including positions that may individually be identical to both such cytokines).

In one embodiment, the chimeric domain includes at least two, three, or four discontinuous segments, each of length at least five, six, seven, eight, nine, ten, 15, or 20 amino acids and having amino acid identity to (or at least 80, 82, 85, 87, 90, 92, 94, 95, 96, 97, 98, or 99% identity to) corresponding segments of a first IL-1 family cytokine and including amino acids predominantly from a second IL-1 family cytokine at remaining positions. In one embodiment, the chimeric domain includes 4, 5, 6, or 7 segments, wherein adjacent segments are from different parental IL-1 family cytokine domains. For example, each amino acid in the domain is located in a peptide of at least 5 or 6 amino acids in length from a naturally occurring human IL-1 family cytokine domain. In one embodiment, the chimeric domain includes at least one, two, or three of: (i) a segment of at least 50, 60, 65, 70, or 75 amino acids in length from IL-1β, (ii) a segment of at least 15, 20, 25 amino acids in length from IL-1Ra; and (iii) another segment of at least 15, 20, 25 amino acids in length from IL-1Ra.

In one embodiment, the discontinuous segments includes residues (i) 1-6 and 45-61, (ii) 1-6 and 86-95, (iii) 45-61 and 86-95, (iv) 1-6 and 148-153, (v) 45-61 and 148-153, or (vi) 86-95 and 148-153, according to the numbering of such positions in IL-1β. The three discontinuous segments from the first IL-1 family cytokine can include, e.g., residues 1-8, 42-120, and 141-153, residues 1-10, 37-125, and 131-153, or residues 1-6, 45-61, 86-95, and 148-153, according to the numbering of such positions in IL-1β. The chimeric domain can be at least 80, 82, 85, 87, 90, 92, 94, 95, 96, 97, 98, 99, or 100% identical to the second IL-1 family cytokine at the remaining positions. In one embodiment, one or more of the borders of the discontinuous segments are located at positions wherein the first and second IL-1 family cytokines are identical or are conserved. The protein can have other features described herein.

In another aspect, this disclosure features an isolated IL-1 inhibitor including a IL-1 family cytokine domain that binds to IL-1RI. For example, the IL-1 inhibitor includes one or more features above or elsewhere herein. In some embodiments, the cytokine domain includes: (a) amino acids identical to IL-1 Ra at the following positions ARG11, SER13, GLN14, GLN15, GLU25, LYS27, LEU29, HIS30, LEU31, GLN32, GLY33, GLN34, ASP35, MET36, GLN38, GLN39, ALA127, GLU128, ASN129, MET130, and GLN141 (according to the numbering of IL-1β) and (b) amino acids identical to IL-1β at the following positions: ALA1, PRO2, VAL3, ARG4, LEU6, PHE46, GLN48, GLU51, SER52, ASN53, LYS55, ILE56, PRO57, LYS92, LYS93, LYS94, LYS103, GLU105, ASN108, GLN149, PHE150, and SER152. In some embodiments, Site A segments A1 and A2 are at least 80% identical (collectively) to corresponding segments of IL-1Ra. In some embodiments, Site B segments B1, B2, and B3 are at least 80% identical (collectively) to corresponding segments of IL-1β. For example, Site A segments A1 and A2 are at least 90% identical (collectively) to corresponding segments of IL-1Ra; and Site B segments B1, B2, and B3 are at least 90% identical (collectively) to corresponding segments of IL-1β. For example, Site A segments A1 and A2 are identical to corresponding segments of IL-1Ra; and Site B segments B1, B2, and B3 are identical to corresponding segments of IL-1β.

In some embodiments, the cytokine domain includes sequences that are at least 80% identical (collectively) to beta strands β2, β3, β10 and β11 of IL-1Ra and sequences that are at least 80% identical (collectively) to beta strands β4, β6, β7, and β8 of IL-1β. In some embodiments, the cytokine domain includes sequences that are identical to beta strands β2, β3, β10 and β11 of IL-1Ra and sequences that are identical to beta strands β4, β6, β7, and β8 of IL-1β.

In some embodiments, the segments and features identified above from IL-1β are derived from IL-1α, or a combination of IL-1β or IL-1α.

In some embodiments, the IL-1 inhibitor includes one or more (e.g., at least two, three, four, five, six, or seven) of the following properties: (i) Site A or Site B residues (and/or extended Site A and extended Site B residues) that are at least 60, 70, 80, 85, 88, 90, 92, 95, 98, or 100% identical to corresponding residues in IL-1β, IL-1α, or IL-1Ra; (ii) A1 and A2 segments that are collectively at least 80, 85, 88, 90, 92, 95, 98, or 100% identical to corresponding residues in IL-1Ra; (iii) B1, B2, and B3 segments that are collectively at least 80% identical to corresponding residues in IL-1β or IL-1α; (iv) a Site A region that is at least 80, 85, 88, 90, 92, 95, 98, or 100% identical to corresponding residues in IL-1Ra; (v) a Site B region is at least 80, 85, 88, 90, 92, 95, 98, or 100% to corresponding residues in IL-1β or IL-1α; (vi) a Site C and/or Site D residues that are at least 50, 60, 70, 80, 85, 88, 90, 92, 95, 98, or 100% identical to corresponding residues in IL-1Ra or IL 36Ra, (vii) a C1 segment that is at least 70, 75, 80, 85, 88, 90, 92, 95, 98, or 100% identical to corresponding residues in IL-1Ra; (viii) a D2 segment that is identical at at least 3, 4, or 5 residues to corresponding residues in IL-1Ra. The cytokine domain differs from IL-1Ra, for example, the cytokine domain is less than 99, 98, 95, 90, 85, 80, 75, 70, 65, 60% identical to IL-1Ra, and/or at least 30, 40, 45, 50, 55, 60, 65, 70% identical to IL-1Ra, e.g., between 40-95%, 40-90%, or 45-85% identical to IL-1Ra. In some embodiments, the cytokine domain does not contain a segment that is greater than 80, 85, 90, 95, or 100% identical to amino acids I46-G59, A55-G59, A55-V83, I60-V83, N84-D95, I46-S110, V49-S110, or I46-G118 of SEQ ID NO:3. In some embodiments, the cytokine domain does not contain a segment that is greater than 80, 85, 90, 95, or 100% identical to amino acids N7-V41, R11-M37, N102-D144, or Y121-D144 of SEQ ID NO:1.

In some embodiments, the inhibitor binds to IL-1RI with $K_D$ of less than 100, 50, 20, 10, 5, or 1 nM. In some embodiments, the inhibitor binds to IL-1RI with a better affinity (e.g., lower $K_D$) and/or a slower dissociation rate than IL-1β or IL-1Ra.

In some embodiments, the inhibitor does not substantially induce IL-6 expression when contacted to IL-1β responsive human cells. Generally, the inhibitor inhibits signaling by IL-1β, e.g., with an IC50 of less than 100, 50, 20, 10, or 5 nM.

In some embodiments, the cytokine domain includes one, two, three or more of the following sequences: WDVNQKTFYLRNNQLVAGYLQGPNV (SEQ ID NO:9); NLEEK (SEQ ID NO:10); RIWDVNQKTFYLRNNQLVAGYLQGPNVNLEEK(SEQ ID NO:11); AMEADQP(SEQ ID NO:12); FLCTAMEADQPVSLTNMPDEGVMVTKFY (SEQ ID NO:13); and/or sequences at least 80, 85, 88, 90, 92, 95, 98, or 100% identical to the foregoing. In some embodiments, the cytokine domain includes one, two, three or more of the following sequences: VQGEESNDKI (SEQ ID NO:14); KKKMEKRF (SEQ ID NO:15); and FSMSFVQGEESNDKIPVALGLKEKNLYLSCVLKDDKPTLQLESVDPKN YPKKKMEKRFVFNKIEINNKLEFES (SEQ ID NO:16); and/or sequences at least 80, 85, 88, 90, 92, 95, 98, or 100% identical to the foregoing. The inhibitor can include other features described herein.

In another aspect, the disclosure provides an isolated protein that includes an amino acid sequence at least 80, 82, 85, 87, 88, 89, 90, 91, 92, 93, 94, 95, 96, 97, 98, 99% or 100% identical to a sequence disclosed herein, e.g., a sequence listed in Table 4 or Example 1, e.g., the amino acid sequence of P01, P02, P03, P04, P05, P06, or P07, or a sequence in Example 1, 5, 6, or elsewhere herein. In some embodiments, the amino acid sequence includes at least one substitution, insertion, or deletion. The amino acid sequence can include fewer than 15, 12, 11, 10, 9, 8, 7, 6, 5, 4, 3, or 2 non-conservative substitutions or fewer than 15, 12, 11, 10, 9, 8, 7, 6, 5, 4, 3, or 2 total substitutions. The amino acid sequence can include at least 1, 2, 3, 4, or 5 substitutions, e.g., conservative substitutions.

Also provided are isolated proteins that include a methionine N-terminal to the amino acid sequence of P01, P02, P03, P04, P05, P06, or P07, or a sequence in Example 1, 5, 6, or elsewhere herein, and isolated proteins that include the amino acid sequence of P01, P02, P03, P04, P05, P06, or P07, or a sequence in Example 1, 5, 6 or elsewhere herein in which the alanine at N-terminus is absent. The foregoing sequences can include other features disclosed herein. For example, the sequence can further include a tag, such as a hexa-histidine sequence (SEQ ID NO:42), e.g., N- or C-terminal relative to the IL-1RI binding sequence. The sequence can further include a moiety that modifies the stability or pharmacokinetics of the IL-1RI binding sequence. For the sequence can further include a serum albumin and/or an Fc domain, or one or more domains thereof, e.g., one or more immunoglobulin constant domains or one or more albumin domains. The protein can have other features described herein. In some embodiments, the isolated protein consists of or consists essentially of a sequence or chimeric domain disclosed herein.

In still another aspect, the disclosure provides an isolated protein that includes a domain having a circularly permuted form of a cytokine domain described herein, e.g., a cytokine domain listed in Table 4 and/or a domain that includes SEQ ID NO:3. The protein can further include a heterologous sequence (such as an Fc domain or albumin) at the N- or C-terminus of the permuted form, optionally spaced by a linker. The protein can have other features described herein.

The disclosure also features pharmaceutical compositions that include one or more receptor binding agents described herein (such as a protein that includes a chimeric cytokine domain). The compositions can be ophthalmic pharmaceutical compositions, topical compositions, or compositions for parenteral administration.

In another aspect, the disclosure features a method of modulating an immune or inflammatory response in a subject. The method can include administering a composition that includes a receptor binding agent described herein to a subject in an amount effective to modulate the immune or inflammatory response in the subject.

In another aspect, the disclosure features a method of treating an IL-1 mediated disorder in a subject. The method includes administering a composition that includes a protein that can bind to IL-1RI, e.g., a receptor binding agent described herein, to the subject. For example, the disorder can be an autoimmune disorder, e.g., rheumatoid arthritis or juvenile chronic arthritis, scleroderma, Sjögren's syndrome, ankylosing spondylitis, Behcet's syndrome, an inflammatory bowel disease, asthma, vasculitis, or psoriasis. The disorder can be a disorder associated with aggregate formation, e.g., hyperuricemia, gout, diabetes (including non-insulin dependent diabetes), Alzheimer's disease, secondary reactive amyloidosis, amyotrophic lateral sclerosis (ALS), Huntington's disease, or Parkinson's disease. The disorder can also be a CAPS (CIAS1 Associated Periodic Syndromes) disorder or other disorder described herein.

In another aspect, the disclosure features a method of treating an IL-1 mediated ocular disorder in a subject. The method can include administering a composition that includes a protein that can bind to IL-1RI, e.g., a receptor binding agent described herein, to the subject. For example, the composition is an ophthalmic composition that is administered topically to an eye of the subject or surrounding region. In one embodiment, the disorder is a dry eye disorder. In some embodiments, the subject does not exhibit manifestations of systemic autoimmune disease. In some embodiments, the subject has Sjögren's syndrome. In some embodiments, the subject has graft-versus-host disease (GVHD). In still other embodiments, the disorder is uveitis.

In still another aspect, the disclosure features a method of inhibiting IL-1 activity. The method includes contacting a receptor binding agent that can bind to IL-1RI to cells responsive to IL-1 or to a subject. Generally, the protein is provided in an amount effective to inhibit IL-1 activity associated with the cells or in the subject. The protein can be contacted to cells from a subject ex vivo.

In another aspect, this disclosure features an isolated nucleic acid that includes one or more sequences encoding the proteins described herein or a nucleic acid disclosed herein (e.g., in Table 5), a sequence that hybridizes to such nucleic acid, or that is at 80, 82, 85, 87, 88, 89, 90, 91, 92, 93, 94, 95, 96, 97, 98, 99% or 100% identical to such nucleic acid. Exemplary hybridizing sequences can be at least 200, 300, 400, 420, or 450 nucleotides in length, e.g., between 420-480 nucleotides in length. The nucleic acid can also include other features disclosed herein.

Also featured is a recombinant host cell that includes a nucleic acid that includes one or more sequences encoding the proteins described herein and a polypeptide chain thereof. A receptor binding agent can be produced by a method that includes maintaining the host cell under conditions that permit expression of the receptor binding agent, and optionally recovering the receptor binding agent, e.g., from cells or media associated with the host cell. For example, the receptor binding agent can be purified from lysate from the cells. The purified receptor binding agent can be formulated, e.g., with one or more of an excipient, a stabilizer, and a buffer.

Also featured is a method of providing a chimeric protein domain. The method includes identifying at least two parental proteins having a common fold (e.g., a first parental protein and a second parental protein), locating at least two segments within the first parental protein and constructing a nucleic acid that has a sequence encoding a chimeric amino acid sequence that includes the two segments from the first parental protein and residues that are predominantly from the second parental protein at remaining positions. The domain can be a domain that is largely composed of β-sheets, or a domain that is largely composed of α-helices, or a domain that has a combination of such elements. For example, the domain can have the fold of a cytokine. The first and second parental proteins can be related by homology, e.g., between 10-40% amino acid identity. In some embodiments the segments from the first protein are located within a single folded protein domain, and the chimeric amino acid sequence includes a form of the folded protein domain that is non-identical to the corresponding domain in the first and second parental protein. In some embodiments, the two parental protein have different functional properties, and the chimeric domain can have properties of one or both of the parental proteins. In some embodiments, the chimeric domain has one binding interface from the first parental protein, and another binding interface from the second parental protein.

Reference is made herein to various regions, segments, and residues in IL-1 family cytokines in relation to Sites A, B, C, and D. The location of such residues, segments, and regions in the sequence of human IL-1β (SEQ ID NO:1) and corresponding positions are provided below and in FIG. 1:

Site A. Site A residues in IL-1β include: ARG11, SER13, GLN14, GLN15, SER21, GLU25, LYS27, LEU29, HIS30, LEU31, GLN32, GLY33, GLN34, ASP35, MET36, GLU128, ASN129, and MET130, and corresponding residues of other IL1 cytokine family members (referred to herein as "Site A residues"). In certain contexts, particularly in connection with IL-1β, reference is made to "extended Site A residues" which include Site A residues as well as GLN149, and PHE150, and corresponding residues of other IL1 cytokine family members. In addition, it is possible to define a "Site A region" as shown in FIG. 4, including for example an A1 segment (corresponding in IL-1β to 11-36 of SEQ ID NO:1) and an A2 segment (corresponding in IL-1β to 125-131 of SEQ ID NO:1), and corresponding segments in other IL1 cytokine family members.

Site B. Site B residues in IL-1β include: ALA1, PRO2, ARG4, GLN48, GLU51, ASN53, ILE56, LYS92, LYS93, LYS94, LYS103, GLU105, and ASN108, and corresponding residues of other IL1 cytokine family members (referred to herein as "Site B residues"). In certain contexts, particularly in connection with IL-1β, reference is made to "extended Site B residues" which include Site B residues as well as PHE46 and SER152 which are outside the Site B region in FIG. 4. In addition, it is possible to define a "Site B region" as shown in FIG. 4, including for example a B1 segment (corresponding in IL-1β to 1-5 of SEQ ID NO:1), a B2 segment (corresponding in IL-1β to 48-56 of SEQ ID NO:1), and a B3 segment (corresponding in IL-1β to 92-98 of SEQ ID NO:1), and corresponding segments in other IL1 cytokine family members.

Site C. Site C residues in IL-1β include: ILE104, ILE106, ASN107, LYS109, GLU111, THR137, LYS138, GLY139, GLY140, GLN141, THR144, and ASP145 and corresponding residues of other IL1 cytokine family members (referred to herein as "Site C residues"). In addition, it is possible to define a "Site C region" as shown in FIG. 4, including for example a C1 segment (corresponding in IL-1β to 136-145 of SEQ ID NO:1), and corresponding segments in other IL1 cytokine family members.

Site D. Site D residues in IL-1β include: LEU6, THR9, LYS63, GLU64, LYS65, and ASN66 and corresponding residues of other IL1 cytokine family members (referred to herein as "Site D residues"). In addition, it is possible to define a "Site D region" as shown in FIG. 4, including, for example, a D1 segment (corresponding in IL-1β to 6-9 of SEQ ID NO:1), a D2 segment (corresponding in IL-1β to 37-41 of SEQ ID NO:1), and a D3 segment (corresponding in IL-1β to 63-66 of SEQ ID NO:1), a D4 segment (corresponding in IL-1β to 86-91 of SEQ ID NO:1), and a D5 segment (corresponding in IL-1β to 150-153 of SEQ ID NO:1) and corresponding segments in other IL1 cytokine family members.

Further identification of the location of residues and regions for Sites A, B, C, and D can be found by alignment of the cytokine in question to the sequences shown in FIG. 4.

The amino acid sequence of IL-1β (human) as referenced herein is:

(SEQ ID NO: 1)
APVRSLNCTLRDSQQKSLVMSGPYELKALHLQGQDMEQQVVFSMSFVQGE

ESNDKIPVALGLKEKNLYLSCVLKDDKPTLQLESVDPKNYPKKKMEKRFV

FNKIEINNKLEFESAQFPNWYISTSQAENMPVFLGGTKGGQDITDFTMQF

VSS.

The amino acid sequence of IL-1α (human) as referenced herein is:

(SEQ ID NO: 2)
SAPFSFLSNVKYNFMRIIKYEFILNDALNQSIIRANDQYLTAAALHNLDE

AVKFDMGAYKSSKDDAKITVILRISKTQLYVTAQDEDQPVLLKEMPEIPK

TITGSETNLLFFWETHGTKNYFTSVAHPNLFIATKQDYWVCLAGGPPSIT

DFQILENQA.

The amino acid sequence of IL-1Ra (human) as referenced herein is: RPSGRKSSKMQAFRIWDVNQKTFYL-RNNQLVAGYLQGPNVNLEEKIDVVPIEPHALFL GIHGGKMCLSCVKSGDETRLQLEAVNITDLSEN-RKQDKRFAFIRSDSGPTTSFESAACP GWFLCTAMEADQPVSLTNMPDEGVMVTKFYFQED (SEQ ID NO:3). The terms IL-1β, IL-1α, and IL-1Ra as used herein refer to the respective mature proteins.

The β sheets referenced herein and shown in FIG. 4 refer to the following sequences:

TABLE 1

| Sheet | IL-1β (SEQ ID NO: 1) | IL-1Ra (SEQ ID NO: 3) | Loop | IL-1β (SEQ ID NO: 1) | IL-1Rα (SEQ ID NO: 3) |
| --- | --- | --- | --- | --- | --- |
| β1 | 6-12 | 11-17 | β1β2 | 13-17 | 18-22 |
| β2 | 18-21 | 23-26 | β2β3 | 22-24 | 27-28 |
| β3 | 25-28 | 29-32 | β3β4 | 29-41 | 33-45 |
| β4 | 42-46 | 46-50 | β4β5 | 47-56 | 51-54 |
| β5 | 57-62 | 55-60 | β5β6 | 63-66 | 61-64 |
| β6 | 67-70 | 65-68 | β6β7 | 71-80 | 69-78 |
| β7 | 81-83 | 79-81 | β7β8 | 84-99 | 82-98 |
| β8 | 100-105 | 99-104 | β8β9 | 106-109 | 105-108 |
| β9 | 110-114 | 109-113 | β9β10 | 115-120 | 114-119 |
| β10 | 121-123 | 120-122 | β10β11 | 124-130 | 123-129 |
| β11 | 131-135 | 130-134 | β11β12 | 136-145 | 135-145 |
| β12 | 146-150 | 146-150 | | | |

Calculations of "homology" or "sequence identity" between two sequences (the terms are used interchangeably herein) are performed as follows. The sequences are aligned according to the alignments provided herein, or, in the absence of an appropriate alignment, the optimal alignment determined as the best score using the Needleman and Wunsch algorithm as implemented in the Needle algorithm of the EMBOSS package using a Blosum 62 scoring matrix with a gap penalty of 10, and a gap extend penalty of 1. See Needleman, S. B. and Wunsch, C. D. (1970) J. Mol. Biol. 48, 443-453; Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley, and tools available from the European Bioinformatics Institute (Cambridge UK) EMBOSS: The European Molecular Biology Open Software Suite (2000), Rice, P. et al., A., Trends in Genetics 16, (6) pp. 276-277 and available online at http://www.ebi.ac.uk/Tools/emboss/align/index.html and http://emboss.open-bio.org/wiki/Appdoc:Needle. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences. To determine collective identity of one sequence of interest to a group of reference sequences, a position is considered to be identical if it is identical to at least one amino acid at a corresponding position in any one or more of the group of reference sequences. With respect to lists of segments, features, or regions, identity can be calculated collectively for all members of such list to arrive an overall percentage identity.

Provided herein are sequences that are at least 80, 82, 85, 87, 88, 89, 90, 91, 92, 93, 94, 95, 96, 97, 98, or 99% identical to sequences disclosed herein.

As used herein, the term "corresponding to" is used to designate the position of an amino acid residue in a polypeptide of interest with respect to a reference polypeptide. In general the position is the one indicated by an alignment provided herein (e.g., FIG. 4).

As used herein, the term "hybridizes under high stringency conditions" describes conditions for hybridization and washing. Guidance for performing hybridization reactions can be found in Current Protocols in Molecular Biology, John Wiley & Sons, N. Y. (1989), 6.3.1-6.3.6, which is incorporated by reference. Aqueous and nonaqueous methods are described in that reference and either can be used. High stringency hybridization conditions include hybridization in 6×SSC at about 45° C., followed by one or more washes in 0.2×SSC, 0.1% SDS at 65° C., or substantially similar conditions. Provided herein are isolated nucleic acids that contain sequences that hybridize under high stringency conditions to nucleic acids encoding amino acid sequences disclosed herein and to the nucleic acids disclosed herein, e.g., in Example 1.

Naturally occurring proteins referenced herein specifically include the human form of such protein, and also forms from other mammalian species.

All patents, published patent applications, and published references cited herein are incorporated by reference for all purposes.

BRIEF DESCRIPTION OF THE DRAWINGS

FIG. 5A is a listing of the amino acid sequence of P01 (SEQ ID NO:17). FIG. 5B is a listing of the amino acid sequence of P02 (SEQ ID NO:18). FIG. 5C is a listing of the amino acid sequence of P03 (SEQ ID NO:19). FIG. 5D is a listing of the amino acid sequence of P04 (SEQ ID NO:20). FIG. 5E is a listing of the amino acid sequence of P05 (SEQ ID NO:21). Segments from IL-1β are shown in bold italics. See also Example 1 below.

DETAILED DESCRIPTION

Figure 1:
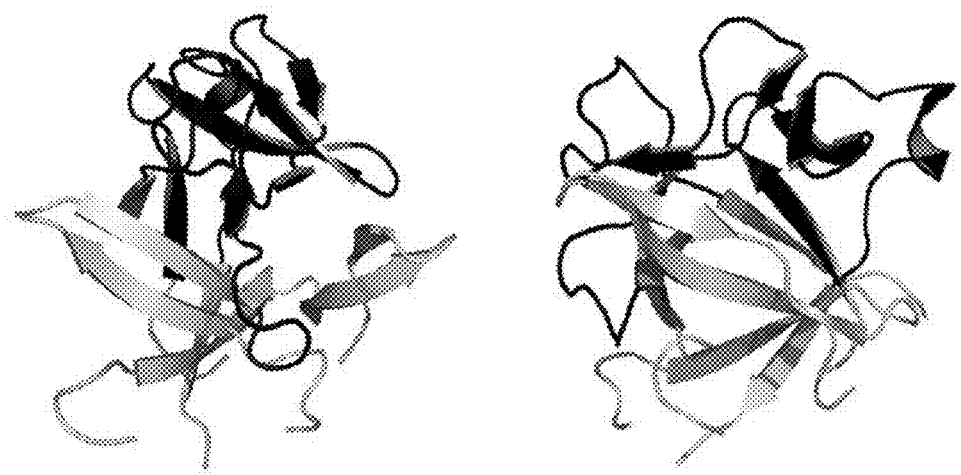
FIG. 1 is a graphic of the structure of P04 as determined from X-ray crystallographic data. The backbone of residues from IL-1Ra are is shown in black, and the backbone of residues from IL-1β is shown in gray.
Figure 2:
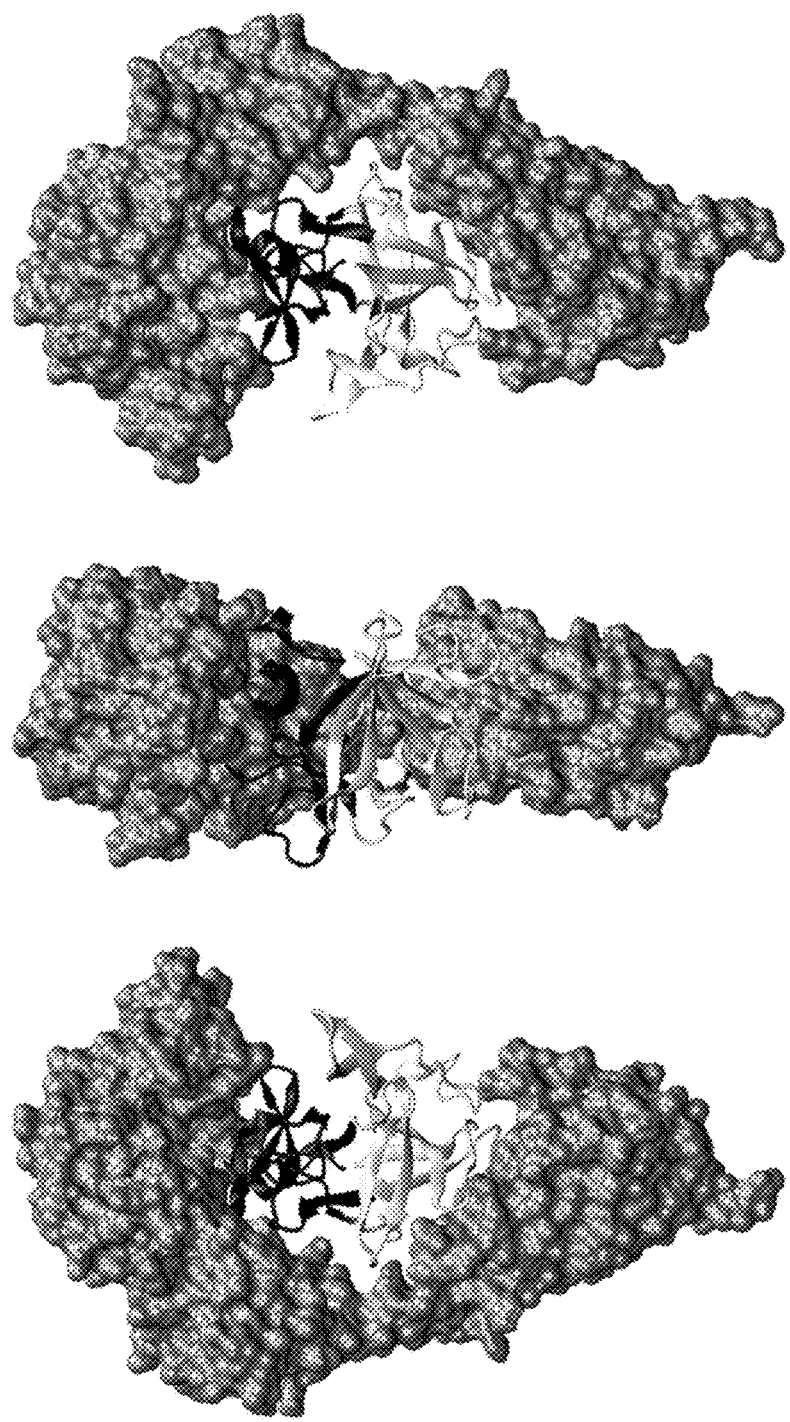
FIG. 2 depicts three views of a model of the P05 protein bound to the extracellular domain of human IL-1RI. In P05, IL-1Ra residues are depicted in black and IL-1β residues are depicted in white
Figure 3:
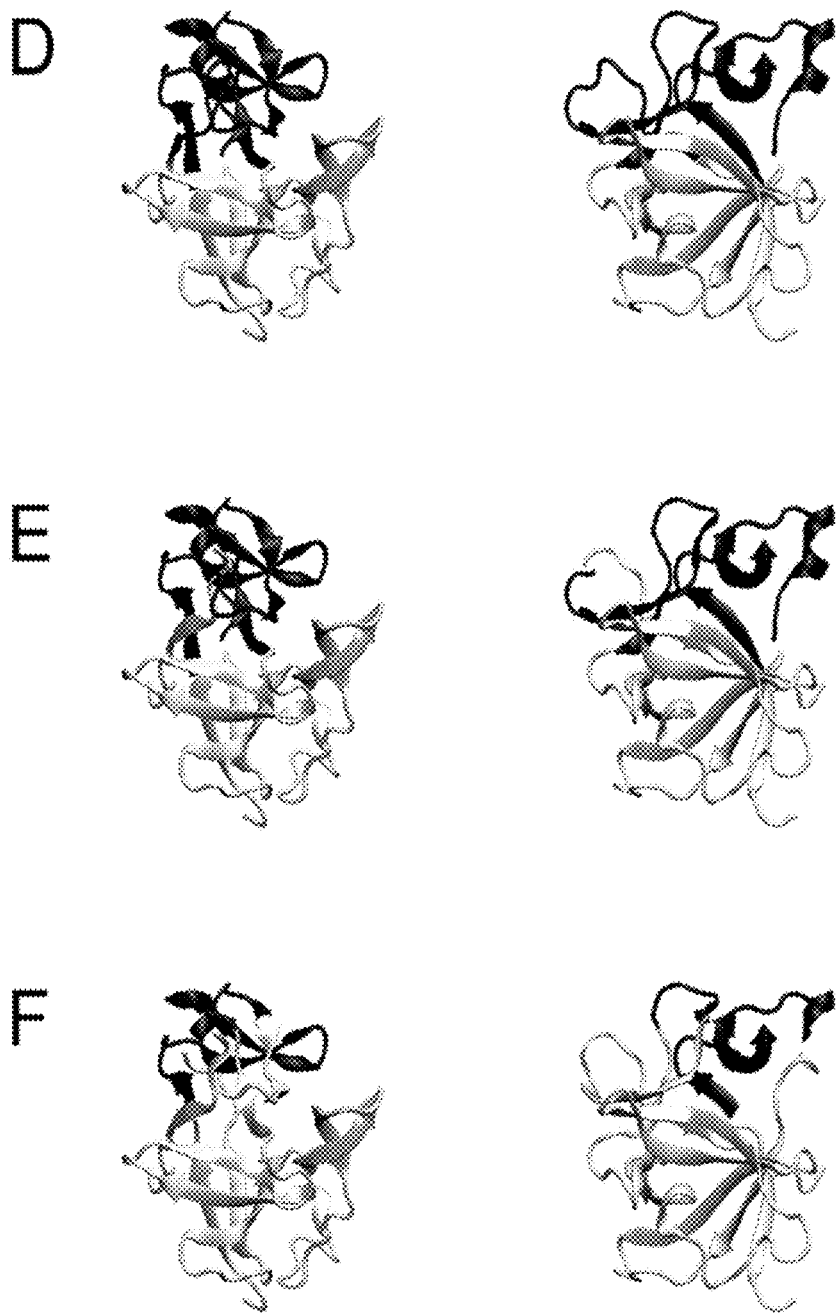
FIG. 3 depicts models of chimeric proteins in which IL-1Ra residues are depicted in black and IL-1β residues are depicted in white. The model depicts the proteins: P01 (FIG. 3A), P03 (FIG. 3B), P04 (FIG. 3C), P05 (FIG. 3D), P07 (FIG. 3E), and P06 (FIG. 3F).
Figure 4:
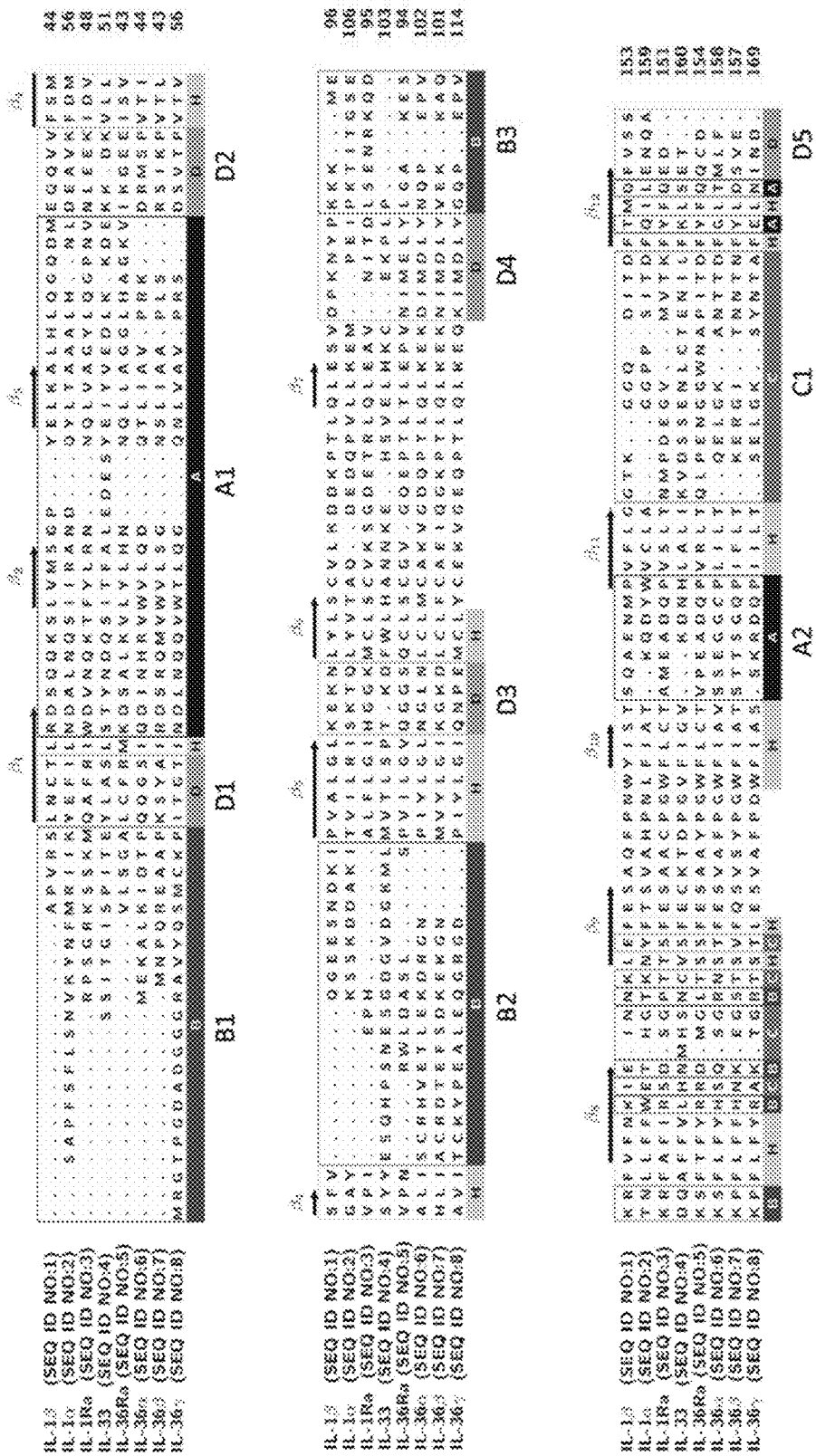
FIG. 4 provides an alignment of several human IL-1 family cytokines: IL-1β (SEQ ID NO:1), IL-1α (SEQ ID NO:2), IL-1Ra (SEQ ID NO:3), IL-33 (SEQ ID NO:4), IL-36Ra (SEQ ID NO:5), IL-36α (SEQ ID NO:6), IL-36β (SEQ ID NO:7), and IL-36γ (SEQ ID NO:8). Segments referenced in the text herein are identified under the alignment. In addition, β-sheets and loops between such sheets are identified.

The IL-1 family of cytokines includes several members, all having a common β-trefoil fold comprised of six β-strands that form a β-barrel capped by another six β-strands. The primary structures of the human and other mammalian forms of these cytokines are known. An exemplary structural alignment of several human IL-1 family members is shown in FIG. 1.

We have discovered, inter alia, that the IL-1 fold is highly plastic. In particular, elements from different members can be combined to provide proteins that agonize or antagonize cytokine signaling. Examples of these proteins include chimeric cytokine domains that include, for example, two or more segments or surface residues from one cytokine in the context of another cytokine or a cytokine consensus sequence, thus creating non-naturally occurring combinations of receptor interaction sites from different IL-1 family cytokines.

IL-1 family cytokines can include at least two primary receptor interaction sites, referred to as Site A and Site B. Sites A and B are involved in contacts to the primary cytokine receptor (e.g., IL-1RI). In the case of IL-1Ra and IL-1β, for example, the two proteins differ substantially with respect to sites A and B such that IL-1Ra makes fewer receptor contacts in Site B than Site A.

We have found that it is possible to construct functional chimeric cytokine domains that include a Site A derived from one cytokine and a Site B derived from another cytokine. The plasticity of the IL-1 fold permits construction of a variety of chimeric cytokine domains to antagonize IL-1 signaling.

In addition, IL-1 family cytokines can include two secondary receptor interaction sites, referred to as Site C and Site D, which are involved in agonism and/or antagonism, and can be determinative of a cytokine's ability to interact with its secondary cytokine receptor (e.g., IL-1RAcP). Inclusion of Site C and/or Site D residues from natural receptor antagonists (such as IL-1Ra) can impart antagonistic properties. Chimeric cytokine domains can be constructed that include one or both of Sites A and B from one or more IL-1 agonists (such as IL-1β and IL-1α) and/or an IL-1 receptor antagonist (such as IL-1Ra) and one or both of Sites C and D from an IL-1 receptor antagonist (such as IL-1Ra). Accordingly, it is possible to produce a chimeric cytokine domain that antagonizes signaling and that includes Site B residues from an IL-1 agonist.

Exemplary combinations are also provided in Table 2 below:

TABLE 2

| | A | B | C | D |
|---|---|---|---|---|
| 1. | IL-1β or 1α | IL-1β or 1α | IL-1Ra | IL-1β or 1α |
| 2. | IL-1β or 1α | IL-1β or 1α | IL-1β or 1α | IL-1Ra |
| 3. | IL-1β or 1α | IL-1β or 1α | IL-1Ra | IL-1Ra |
| 4. | IL-1Ra | IL-1β or 1α | IL-1Ra | IL-1β or 1α |
| 5. | IL-1Ra | IL-1β or 1α | IL-1β or 1α | IL-1Ra |
| 6. | IL-1Ra | IL-1β or 1α | IL-1Ra | IL-1Ra |

The source sequences can be identical to the human sequences for the identified cytokine domains or can contain mutations relative to the human sequences, e.g., such that they are at least 70%, 75%, 80%, 85%, 90%, 95% or more identical to the human sequences in each respective region, e.g., they can include one or more segments from each region.

Sources for Site A residues and Site B residues can be chosen to maximize affinity for the primary receptor. For example, to bind IL-1RI, Site A residues can be derived from IL-1Ra, and Site B residues can be derived from IL-1β.

A chimeric cytokine domain can have the ability to bind an IL-1 family receptor, e.g., human IL-1RI with a $K_D$ of less than $10^{-8}$, $10^{-9}$, or $10^{-10}$, e.g., a $K_D$ within 10 or 100 fold that of a natural receptor ligand (e.g., IL-1β, IL-1α, or IL-1Ra) under the same conditions or less than that of a natural ligand (e.g., IL-1β, IL-1α, or IL-1Ra) under the same conditions. Moreover, in certain embodiments, the chimeric cytokine domain binds with a $K_D$ less than, a $K_{on}$ faster than, or a $K_{off}$ slower than at least one of its parental cytokine domains.

Chimeric cytokine domains that bind to IL-1 family receptor and which antagonize receptor signaling can be used as receptor binding agents, e.g., to treat disorders mediated by IL-1 family cytokine signaling as described below. For example, in some embodiments, the chimeric cytokine domain binds to IL-1RI and antagonizes IL-1 signaling. For example, it has an $IC_{50}$ of less than 100, 10, 1, 0.6, or 0.3 nM.

In certain embodiments, the cytokine domain can be at least 40, 45, or 50% identical, but less than completely identical, e.g., less than 95, 90, 85, or 80% identical to a first IL-1 family cytokine domain. At the same time, the cytokine domain can also be at least 40, 45, or 50% identical, but less than completely identical, e.g., less than 95, 90, 85, or 80% identical to a second IL-1 family cytokine domain. The first and second IL-1 family cytokine domain can be less than 50% identical to each other. For example, the first IL-1 family cytokine domain can be an agonist (e.g., IL-1β or IL-1α), whereas the second IL-1 family cytokine domain can be a receptor antagonist (e.g., IL-1Ra).

In some embodiments, at least 80, 85, 90, 92, 94, 95, 97, 98, 99, or 100% of the positions within the cytokine domain have the property that, at each such position, the amino acid present is either identical to the first IL-1 family cytokine domain or to the second IL-1 family cytokine domain (or both if the first and second IL-1 family cytokine are identical at the particular position). Where 100% of the amino acid positions in the cytokine domain have this property, the domain is a complete chimera of two cytokines. Chimeric cytokine domains can also be made from more than two cytokines and can also have mutations relative to its parental cytokines (e.g., one or more particular positions where the amino acid present differs from the corresponding amino acid in each of its parental cytokines).

Cytokine domains can have Site A, B, C, and D residues from different IL-1 cytokine domains, and likewise can have Site A, B, C, and D regions from different IL-1 cytokine domains.

SITE A. For example, in certain embodiments, a cytokine domain includes residues from a receptor antagonist (e.g., IL-1Ra) or an agonist at at least 5, 10, 12, 15, 16, 17, or 18 of the Site A residues identified above, or at at least 5, 10, 12, 15, 16, 17, 18, 19, or 20 of the extended Site A residues identified above, or conservative substitutions of such residues, or at least 50, 65, 75, 80, 90, 95, or 100% of such residues. In some embodiments, the cytokine domain includes residues that are at least 70, 75, 80, 85, 88, 90, 92, 95, or 100% identical to segments A1, A2, or A1+A2 in a receptor antagonist (e.g., IL-1Ra) or an agonist (e.g., IL-1β or IL-1α).

In certain embodiments, a cytokine domain includes residues identical to an IL-1 agonist (e.g., IL-1β residues) at at least 5, 10, 12, 15, 16, 17, or 18 of the Site A residues identified herein, or at least 5, 10, 12, 15, 16, 17, or 18 of the extended Site A residues identified above, or conservative substitutions of such residues, or at least 50, 65, 75, 80, 90, 95, or 100% of such residues.

SITE B. In certain embodiments, a cytokine domain includes residues identical to an IL-1 agonist (e.g., IL-1β or IL-1α residues) at at least 2, 3, 5, 8, 9, 10, 11, 12, 13, 14, or 15 of the Site B residues identified herein, or conservative substitutions of such residues, or at least 50, 65, 75, 80, 90, 95, or 100% of such residues. In some embodiments, the cytokine domain includes residues that are at least 70, 75, 80, 85, 88, 90, 92, 95, or 100% identical to segments B1, B2, B3, B1+B2, B1+B3, B2+B3, or B1+B2+B3 in an IL-1 cytokine agonist (e.g., IL-1β or IL-1α).

SITE C. In certain embodiments, a cytokine domain includes residues identical to a receptor antagonist (e.g., IL-1Ra residues) at at least 2, 3, 4, 5, 6, 7, 8, 9, 10, 11 or 12 of the Site C residues identified herein, or conservative substitutions of such residues, or at least 50, 65, 75, 80, 90, or 100% of such residues. In some embodiments, the cytokine domain includes residues that are at least 50, 65, 75, 80, 90, or 100% identical to the segment C1 in a receptor antagonist (e.g., IL-1Ra).

In certain embodiments, the cytokine domain can include, for example, one or more of: a hydrophobic amino acid (e.g., Met or Ile) at the position corresponding to THR137 of SEQ ID NO:1, or a hydrophobic, e.g., an aliphatic amino acid (e.g., Val or Ile), at the position corresponding to GLN141 of SEQ ID NO:1, and a non-acidic amino acid, such as a basic amino acid (e.g., Lys or Arg) at the position corresponding to ASP145 of SEQ ID NO:1, and such residues at positions corresponding thereto in other IL-1 cytokines. Evidence indicates that Asp145 is important to recruitment of IL-1RAcP, and accordingly mutation to a non-acidic residue disrupts agonist activity and can be used to confer antagonistic properties. Accordingly, in certain embodiments, a non-acidic amino acid, such as a basic amino acid (e.g., Lys or Arg) or a hydrophobic amino acid, is located at the position corresponding to ASP145 of SEQ ID NO:1.

SITE D. In certain embodiments, a cytokine domain includes residues identical to a receptor antagonist (e.g., IL-1Ra residues) at at least one, two, three, four, five, or six of the Site D residues identified herein, or a conservative substitution of such residue, or at least 50, 65, 75, 80, 90, 95, or 100% of such residues. In some embodiments, the cytokine domain includes residues that are at least 50, 65, 75, 80, 90, 95, or 100% identical to segments D1, D2, D3, D4, D5, D1+D2, D1+D2+D3, and combinations thereof in a receptor antagonist (e.g., IL-1Ra).

Several residues in IL-1β contact or are in proximity with IL-1RI, for example: ALA1, PRO2, VAL3, ARG4, LEU6, ARG11, SER13, GLN14, GLN15, GLU25, LYS27, LEU29, HIS30, LEU31, GLN32, GLY33, GLN34, ASP35, MET36, GLN38, GLN39, PHE46, GLN48, GLU51, SER52, ASN53, LYS55, ILE56, PRO57, LYS92, LYS93, LYS94, LYS103, GLU105, ASN108, ALA127, GLU128, ASN129, MET130, GLN141, GLN149, PHE150, and SER152. In addition to the designation into sites as described above, these residues can be classified into two sets: Set 1 and Set 2.

Exemplary Set 1 residues in IL-1β include: ARG11, SER13, GLN14, GLN15, GLU25, LYS27, LEU29, HIS30, LEU31, GLN32, GLY33, GLN34, ASP35, MET36, GLN38, GLN39, ALA127, GLU128, ASN129, MET130, and GLN141 and corresponding residues in other IL-1 cytokine family members. Extended Set 1 residues include interaction Set 1 residues and residues within 4 Angstroms of the foregoing in the 1ITB structure. Exemplary Set 2 residues in IL-1β include: ALA1, PRO2, VAL3, ARG4, LEU6, PHE46, GLN48, GLU51, SER52, ASN53, LYS55, ILE56, PRO57, LYS92, LYS93, LYS94, LYS103, GLU105, ASN108, GLN149, PHE150, and SER152 and corresponding residues in other IL-1 cytokine family members. Extended Set 2 residues include interaction Set 2 residues and residues within 4 Angstroms of the foregoing in the 1ITB structure. In certain embodiments, a cytokine domain includes IL-1β residues at at least 15, 16, 17, 18, 19, 20, or 21 of the Set 1 residues identified above. In certain embodiments, a cytokine domain includes IL-1β residues at at least 15, 16, 17, 18, 19, 20, 21, or 22 of the Set 2 residues identified above. In some embodiments, a cytokine domain includes IL-1β residues at at least 15, 16, 17, 18, 19, 20, or 21 of the extended Set 1 residues. In some embodiments, a cytokine domain includes IL-1β residues at at least 15, 16, 17, 18, 19, 20, or 21 of the extended Set 2 residues.

Other variants that can be used as a receptor binding agent include proteins having sequences derived from two or more IL-1 cytokine family members. Examples of such variants include chimeric domains based on IL-1β and IL-1Ra. For example, the variants can include one or more amino acid residues from Set 1 of IL-1Ra (e.g., all Set 1 residues from IL-1Ra) and one or more amino acid residues from Set 2 of IL-1β (e.g., all Set 2 residues from IL-1β).

Exemplary chimeric proteins are predominantly (e.g., at least 50, 60, 70, 75, 78, 80, 82, 84, 86, 88, 90, 92, 94, 96, 97, 98, 99, or 100%) identical to IL-1β at the following amino acids positions (i.e., based on correspondence to these positions in IL-1β): residues 1-8, 42-120, and 141-153 of SEQ ID NO:1; residues 1-6, 45-61, 86-95, and 148-153 of SEQ ID NO:1; and residues 1-10, 37-125, and 131-153 of SEQ ID NO:1.

The remaining residues can be predominantly (e.g., at least 50, 60, 70, 75, 78, 80, 82, 84, 86, 88, 90, 92, 94, 96, 97, 98, 99, or 100%) identical to IL-1Ra. For example, the following amino acid positions can be predominantly identical to IL-1Ra: residues 9-41 and 121-140 of SEQ ID NO:1; residues 7-44, 62-85, and 96-147 of SEQ ID NO1; and residues 11-36 and 126-130 of SEQ ID NO:1.

In certain embodiments, the cytokine domain is identical to IL-1β at at least 2, 4, 5, 10, or 20 positions in addition to amino acid positions Gln48-Asn53 of IL-1β, and, e.g., the cytokine domain is predominantly, e.g., at least 50, 60, 70, 75, 78, 80, 82, 84, 86, 88, 90, 92, 94, 96, 97, 98, 99, or 100% identical to a cytokine other than IL-1β.

In certain embodiments, the cytokine domain includes at least 3, 4, 5, 6, 7, or 8 residues identical to IL-1β at positions corresponding to 1-8 of SEQ ID NO:1. For example, it includes residues identical to IL-1β at positions corresponding to 3, 4, or all 5 of: ALA1, PRO2, VAL3, ARG4, and LEU6.

In certain embodiments, the cytokine domain includes at least 8, 9, 10, 11, 12, 13, 14, 15, 16, or 17 residues identical to IL-1β at positions corresponding to 45-61 of SEQ ID NO:1. For example, it includes residues identical to IL-1β at positions corresponding to 3, 4, 5, 6, 7 or 8 of: PHE46, GLN48, GLU51, SER52, ASN53, LYS55, ILE56, and PRO57.

In certain embodiments, the cytokine domain includes at least 5, 6, 7, 8, 9, or 10 residues identical to IL-1β at positions corresponding to 86-95 of SEQ ID NO:1. For example, it includes residues identical to IL-1β at positions corresponding to one, two, or all three of LYS92, LYS93, and LYS94.

In certain embodiments, the cytokine domain includes at least 3, 4, 5, or 6 residues identical to IL-1β at positions corresponding to 148-153 of SEQ ID NO:1. For example, it includes residues identical to IL-1β at positions corresponding to one, two, or all three of GLN149, PHE150, and SER152.

In certain embodiments, the cytokine domain does not include a threonine at the position corresponding to THR147 in IL-1β. For example, this position can be an aromatic, such as a tyrosine. The aromatic at the position corresponding to THR147 in IL-1β can pack against another aromatic (e.g., tryptophan) present in several embodiments at position 11 (according to IL-1β numbering).

In certain embodiments, the cytokine domain does not include an aromatic at the position corresponding to CYS8 in IL-1β. For example, this position can be an amino acid other than phenylalanine, or other than an aromatic. For example, it can be cysteine, valine, serine, threonine or alanine. This position is located near other bulky residues, particularly MET44 and MET148 (according to IL-1β numbering). Preferably, not all three of positions 8, 43, and 148 are bulky residues.

In certain embodiments, the cytokine domain includes at least five, six, or seven residues identical to IL-1Ra at positions corresponding to 30-36 of SEQ ID NO:1, e.g., at least five, six, or seven residues identical to YLQGPNV (SEQ ID NO:43). For example, the cytokine domain includes at least 10, 12, 14, 16, 18, 19, 20, 21, 22, 23, 24, 25, or 26 residues identical to IL-1Ra at positions corresponding to 11-36 of SEQ ID NO:1. The cytokine domain can also include a basic residue at the position corresponding to 145 of SEQ ID NO:1.

In certain embodiments, the cytokine domain includes: (a) glutamic acid at the position corresponding to Val40 of IL-1β and lysine at the position corresponding to Lys65 of IL-1β; (b) arginine at the position corresponding to Thr9 of IL-1β and glutamine at the position corresponding to Gln149 of IL-1β; and/or (c) lysine at the position corresponding to V41 of IL-1β and serine at the position corresponding to Ser152 of IL-1β.

The cytokine domain can also include at least four, five, six, or seven residues identical to IL-1Ra at positions corresponding to 126-132, e.g., at least four, five, six, or seven residues identical to MEADQPVS (SEQ ID NO:44).

In certain embodiments, the cytokine domain includes at least 10, 12, 14, 16, 18, 19, 20, 21, 22, 23, or 24 residues identical to IL-1β at positions corresponding to 62-85 of SEQ ID NO:1.

In some embodiments, the cytokine domain includes one or more of the following amino acid sequences (e.g., all four of): RSLAFR (SEQ ID NO:45), IDVSFV (SEQ ID NO:46), KKMDKR (SEQ ID NO:47), and KFYMQF (SEQ ID NO:48); one or more of the following (e.g., all four of) RSLAFR (SEQ ID NO:45), IDVSFV (SEQ ID NO:46), NKLSFE (SEQ ID NO:49), and KFYMQF (SEQ ID NO:48); one or more of the following (e.g., all four of) RSLAFR (SEQ ID NO:45), EEKFSM (SEQ ID NO:50), RFVFIR (SEQ ID NO:51), and VTKFTM (SEQ ID NO:52); one or more of the following (e.g., all four of) RSLAFR (SEQ ID NO:45), EEKFSM (SEQ ID NO:50), FESAAC (SEQ ID NO:53), and VTKFTM (SEQ ID NO:54); or one or more of the following (e.g., all four of) LNCRIW (SEQ ID NO:55), EEKFSM (SEQ ID NO:50), PNWFLC (SEQ ID NO:56), and KFYMQF (SEQ ID NO:48).

Chimeric proteins can be used for a variety of purposes. For example, they can be used to increase or decrease receptor signaling activity, to detect cells expressing receptors, or to purify cells or proteins to which they bind.

Specific examples of chimeric cytokine domains that are based on IL-1β and IL-Ra are provided in Example 1 below and include the following exemplary cytokine domains that antagonize IL-1 signaling:

P01. The P01 domain includes three segments from IL-1Ra corresponding to amino acids Ala12-Val48, Ile60-Val83, and Asp95-Tyr147 of SEQ ID NO:3, and the remaining four segments from IL-1β. Overall, the P01 domain has 74 of 153 amino acids from IL-1β (about 48% identity) and 119 amino acids from IL-1Ra (about 77% identity). These percentages add up to greater than 100% because a number of amino acids in P01 and other exemplary proteins disclosed herein are amino acids that are conserved between IL-1β and IL-1Ra and accordingly contribute to the percentage identity for both IL-1β and IL-1Ra.

P02. The P02 domain includes three segments from IL-1Ra corresponding to amino acids Ala12-Val48, Ile60-Val83, and Ser110-Tyr147 of SEQ ID NO:3, and the remaining four segments from IL-1β. Overall, the P02 domain has 85 of 153 amino acids from IL-1β (about 55% identity) and 108 amino acids from IL-1Ra (about 70% identity).

P03. The P03 domain includes two segments from IL-1Ra corresponding to amino acids Ala12-Lys45 and Phe100-Lys145 of SEQ ID NO:3, and the remaining three segments from IL-1β. Overall, the P03 domain has 94 of 153 amino acids from IL-1β (about 61% identity) and 91 amino acids from IL-1Ra (about 64% identity).

P04. The P04 domain includes two segments from IL-1Ra corresponding to amino acids Ala12-Lys45 and Ala114-Lys145 of SEQ ID NO:3, and the remaining three segments from IL-1β. Overall, the P04 domain has 104 of 153 amino acids from IL-1β (about 68% identity) and 89 amino acids from IL-1Ra (about 58% identity).

P05. The P05 domain includes two segments from IL-1Ra corresponding to amino acids Arg14-Lys45 and Phe120-Tyr147 of SEQ ID NO:3, and the remaining three segments from IL-1β. Overall, the P05 domain has 108 of 153 amino acids from IL-1β (about 70% identity) and 85 amino acids from IL-1Ra (about 55% identity).

Other chimeric proteins can be similarly constructed. For example, chimeric proteins can be made between IL-1α and IL-1Ra, e.g., specifically domains including the identified segments of IL-1Ra in combination with corresponding residues from IL-1α rather than IL-1β for each of the above examples.

Protein Modifications and Substitutions

Protein sequences, such as those described herein, can be varied, e.g., by making one or more conservative substitutions. Conservative substitutions can be made to retain function or to make modest changes in function. Exemplary conservative substitutions are described in the following table:

TABLE 3

| Original | Exemplary Substitutions | Further Specific Substitutions |
|---|---|---|
| Ala (A) | val; leu; ile | val |
| Arg (R) | lys; gln; asn | lys |

TABLE 3-continued

| Original | Exemplary Substitutions | Further Specific Substitutions |
|---|---|---|
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; leu | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; leu; norleucine | ala |

Substitutions can be chosen based on their potential effect on (a) backbone structure in the vicinity of the substitution, for example, a sheet or helical conformation, (b) the charge or hydrophobicity of the molecule at the target site, or (c) the volume and branching of the side chain. Amino acid residues can be classified based on side-chain properties: (1) hydrophobic: norleucine, met, ala, val, leu, ile; (2) neutral hydrophilic: cys, ser, thr; asn; gln; (3) acidic: asp, glu; (4) basic: his, lys, arg; (5) residues that affect backbone conformation: gly, pro; and (6) aromatic: trp, tyr, phe.

Non-conservative substitutions can include substituting a member of one of these classes for a member of a different class. Conservative substitutions can include substituting a member of one of these classes for another member of the same class.

The significance of a particular residue can also be evaluated in the context of the hydropathic index for the amino acid. Each amino acid has been assigned a hydropathic index on the basis of its hydrophobicity and charge characteristics: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). For a discussion of the hydropathic amino acid index and its significance see, for example, Kyte et al., 1982, J. Mol. Biol. 157:105-131.

The sequence of a protein can be varied by any method, including oligonucleotide-mediated (site-directed) mutagenesis, (Carter et al., Nucl. Acids Res., 13:4331, 1986; Zoller et al., Nucl. Acids Res., 10:6487, 1987), cassette mutagenesis (Wells et al., Gene, 34:315, 1985), restriction selection mutagenesis (Wells et al., Philos. Trans. R. Soc. London, 317:415, 1986), and PCR mutagenesis. See also In Vitro Mutagenesis Protocols: Third Edition, Braman (ed.), Humana Press, (2010) ISBN: 1607616513 and PCR Cloning Protocols: From Molecular Cloning to Genetic Engineering, Chen and Janes (ed.), Humana Press, (2002) ISBN: 0896039730.

Scanning amino acid analysis can be employed to evaluate one or more amino acids along a contiguous sequence. The method can involve mutating each or nearly each amino acid in a region to a particular amino acid, e.g., to a relatively small, neutral amino acid such as alanine, serine, or valine. Alanine is typically chosen because it eliminates the side-chain beyond the beta-carbon and is less likely to alter the main-chain conformation of the variant (Cunningham and Wells, Science, 244: 1081-1085, 1989). It is also the most common amino acid and is frequently found in both buried and exposed positions (Creighton, The Proteins, (W. H. Freeman & Co., N.Y.); Chothia, J. Mol. Biol., 150:1, 1976). The scanning process can also be adapted to make more marked changes, e.g., charged residues can be changed to residues of the opposite charge, residues with short side chains can be replaced with ones with bulk side chains. For example, arginine scanning is an approach that can be used instead of or in addition to alanine scanning. The scanning can be applied to each residue in a region or to residues of a particular property, e.g., residues at or near the surface of a protein or likely to be at or near the surface of the protein.

The structure of a protein, one of its domains, or a complex involving the protein can be modeled, e.g., by performing homology based modeling, energy minimization and/or other modeling using known solved structures. Such methods include: Accelrys Software Inc., Discovery Studio®, Release 3.0, San Diego: Accelrys Software Inc., 2010, AMBER™ modeling software (Case et al. (2005) J. Computat. Chem. 26, 1668-1688 and Case et al. (2010), AMBER 11, University of California, San Francisco, Calif. USA) and CHARMM™ modeling software (Molecular Simulations Inc.). See also generally Baker and Sali, Science 294(5540): 93-6, 2001). The structure can also be determined directly, e.g., using X-ray crystallography and/or NMR spectroscopy.

Exemplary PDB structures describing the structure of IL-1 family cytokines include: 1I1B, 1ILR, 1IRA, 1ITB, 2I1B, 2ILA, 2KLL, 4I1B, 5I1B, 6I1B, 7I1B, 8I1B, 9ILB, and 1MD6 (available by http from www.pdb.org from RCSB-Rutgers, Piscataway N.J., USA, and from the National Library of Medicine (Bethesda, Md., USA)). For example, the structures of IL-1β alone and in complex with the receptor IL-1RI have been solved. See e.g., Finzel et al. (1989) J. Mol. Biol. 209: 779-791, PDB 1ITB, and Vigers et al. (1997) Nature 386: 190-194. The structure of IL-1Ra with IL-1RI has also been solved. See, e.g., PDB 1IRA and Schreuder et al., (1997) Nature 386: 194-200.

Homology modeling can be assisted by alignment of sequences, e.g., using computer software such as Basic Local Alignment Search Tool (BLAST), PSI-BLAST, PHI-BLAST, WU-BLAST-2, and/or MEGABLAST. See Altschul et al., 1990, J. Mol. Biol. 215, 403-410; Altschul et al., 1996, Methods in Enzymology 266, 460-480; and Karlin et al., 1993, PNAS USA 90, 5873-5787. Additional algorithms for aligning macromolecules (amino acid sequences and nucleic acid sequences) include FASTA (Pearson, 1995, Protein Science 4, 1145-1160), ClustalW (Higgin et al., 1996, Methods Enzymol. 266, 383-402), DbClustal (Thompson et al., 2000, Nucl. Acids Res. 28, 2910-2926), and the Molecular Operating Environment (Chemical Computing Group, Montreal, Quebec Canada H3A 2R7). In addition, the algorithm of Myers and Miller (Myers & Miller, CABIOS 4, 11-17, 1988) which is incorporated into the ALIGN program (version 2.0) of the GCG sequence alignment software package can be used.

A consensus sequence for IL-1β and IL-1Ra can be obtained by comparing the two sequences and identifying residues that are identical or that are highly conserved. A chimeric cytokine domain described herein can have at least 60, 70, 80, 90, 95, or 100% of such identical residues or highly conserved residues. An exemplary consensus sequences is: $DXXQKX_{\{8-9\}}L-AXXL$ QGX$_{\{18\text{-}28\}}$LGX$_{\{7\}}$LSCVXXXDXXXLMEXV X$_{\{8\text{-}9\}}$ KXXKRFXFX$_{\{10\}}$FESAXXPXWXXXTXXXXXXPV XLX$_{\{5\text{-}6\}}$GXXXTXFXXQ (SEQ ID NO:57), where X is independently any amino acid and the subscripted number or range is the number of occurrences. A chimeric cytokine domain described herein can have at least 60, 70, 80, 90, 95, or 100% identity to the consensus sequence (wherein X residues are not counted towards identity). Other consensus sequences can be identified in like manner.

Further variants of an IL-1 cytokine family member can be made and evaluated using a display-based system or other library based screening. For example, the protein variants can be displayed or expressed and evaluated for ability to bind to a receptor for the IL-1 cytokine family member. For example, variants of IL-1β, IL-1Ra, or a cytokine domain described herein can be evaluated for ability to bind to the soluble extracellular domain of IL-1RI. A general description of display-based systems include the following: for cell display, Chao et al. Nat Protoc. 2006; 1(2):755-68; Colby et al. Methods Enzymol. 2004; 388:348-58; Boder et al., Methods Enzymol. 2000; 328:430-44), for phage display (e.g., Viti et al., Methods Enzymol. 2000; 326:480-505 and Smith (1985) Science 228:1315-1317), and for ribosome display (e.g., Mattheakis et al. (1994) Proc. Natl. Acad. Sci. USA 91:9022 and Hanes et al. (2000) Nat Biotechnol. 18:1287-92; Hanes et al. (2000) Methods Enzymol. 328: 404-30; and Schaffitzel et al. (1999) J Immunol Methods. 231(1-2):119-3.

Although many embodiments herein are exemplified using human IL-1 cytokine sequences as parental domains, other sequences can be used. Numerous other IL-1 cytokines, e.g., from other species, are known and available and can be found in public databases such as Entrez (the National Library of Medicine, Bethesda Md.) and EBI-EMBL (Hinxton, Cambridge UK). Examples of such sequences from the UNIPROT database (available at UniProt.org and see The UniProt Consortium, Nucleic Acids Res. D142-D148 (2010)), include the following:

| Protein | Accession Numbers |
|---|---|
| IL-1α | P01583, P01582, P16598, P08831, Q28385, Q28579, O46612, P48089, P18430, P04822, P46647, O46613, Q3HWU1, P79161, Q60480, P79340 |
| IL-1β | P01584, P10749, Q28386, P09428, P14628, P21621, Q63264, P41687, P48090, Q9YGD3, P26889, Q2MH07, Q28292, Q9WVG1, P46648, P79182, P51493, Q865X8 |
| IL-1Ra | P18510, P25085, O18999, P26890, P25086, Q9GMZ4, Q9BEH0, O77482, Q866R8, Q29056 |
| IL-1RI | Q02955, P14778, P13504 |
| IL-1RAcP | Q9NPH3, Q61730, P59822, Q63621 |

Cytokine domains described herein can also include substitutions present in variant cytokine domains that are able to bind to IL-1RI. For example, position 15 of SEQ ID NO:1 (corresponding to position 20 of SEQ ID NO:3) can be Met or Asn. Position 30 of SEQ ID NO:1 (corresponding to position 34 of SEQ ID NO:3) can be Gly, His, Trp, or Met.

Additional exemplary variants of IL-1β and IL-1Ra include those described in Boraschi et al. (1996) Frontiers in Bioscience: A Journal and Virtual Library 1, d270-308, Evans et al., J. Biol. Chem., 270:11477 (1995) and Greenfeder et al., J. Biol. Chem., 270:22460 (1995). For example, variants of IL-1β include R11G, R11A, Q15H, E105G, and T147G. See, e.g., Evans et al. Variants of IL-1Ra include W16Y, Q20M, Q20N, Y34G, Y34H, Y34W, Y34M, Y147G, Y147H, Y147M, K145D, H54P, V18S, T108K, C116F, C122S, C122A, Y147G, H54P, H54I, and others in Evans et al. and Greenfeder et al., J. Biol. Chem., 270:22460 (1995). A cytokine domain can include a residue identical to IL-1Ra at one of the foregoing positions. A cytokine domain can also include a residue differing from one of the foregoing mutations at a corresponding position.

In addition, IL-1 family cytokines can include one or more unpaired cysteine residues. One or more, e.g., two, three or all such unpaired cysteine residues can be mutated to another amino acid, e.g., an uncharged amino acid such as alanine or serine. For example, P01 includes cysteines at positions 67, 70, 116, and 122 of SEQ ID NO:17. One, two, three or all four such cysteines can be substituted with another amino acid, e.g., an uncharged amino acid such as alanine or serine. P02 includes cysteines at positions 67, 70, 116, and 122 of SEQ ID NO:18. One, two, three, or all four such cysteines can be substituted with another amino acid, e.g., an uncharged amino acid such as alanine or serine. P03 includes cysteines at positions 70, 116, and 122 of SEQ ID NO:19. One, two, or all three such cysteines can be substituted with another amino acid, e.g., an uncharged amino acid such as alanine or serine. P04 includes cysteines at positions 70, 116, and 122 of SEQ ID NO:20. One, two, or all three such cysteines can be substituted with another amino acid, e.g., an uncharged amino acid such as alanine or serine. P05 includes cysteines at positions 8, 70, and 122 of SEQ ID NO:21. One, two, or all three such cysteines can be substituted with another amino acid, e.g., an uncharged amino acid such as alanine or serine.

An IL-1 family cytokine domain, including the chimeric cytokine domains described herein, can also be cyclically permutated. For example, a C-terminal segment from the domain can be repositioned so that it is N-terminal to the original N-terminus and an N-terminal segment (generally comprising the remainder of the original protein after excision of the C-terminal segment). The two repositioned segments can be separated by a linker (e.g., of between about three to ten amino acids). Generally, all the amino acids in the domain prior to permutation are retained except for the change in order. In some embodiments, the cut point for the permutation can be in a flexible region, e.g., a flexible loop such as such as the β6-β7 (e.g., amino acids corresponding to 71-80 of SEQ ID NO:3) or the β7-β8 loop (e.g., amino acids corresponding to 84-99 of SEQ ID NO:3).

In some embodiments, a receptor binding agent described herein, e.g., a receptor binding agent which includes an IL-1 family cytokine domain has a molecular weight less than 30, 25, 22, 20, 19, 18, or about 17 kDa. In some embodiments, the receptor binding agent has a molecular weight greater than 18, 19, 20, 22, 25, 30, 40, 45, or 50 kDa. For example, the receptor binding agent can include other polypeptide, polymeric or non-polymeric components, for example, components which modify the agents pharmacokinetics, stability, immunogenicity, and/or molecular weight. The protein may include other modifications, e.g., post-translational or synthetic modifications. In certain embodiments, the receptor binding agent is not glycosylated. In other embodiments, the receptor binding agent includes at least one glycosylation.

For example, receptor binding agents described herein can include additional domains and features. For example, a receptor binding agent can be fused, directly or indirectly, to a domain of an antibody protein, e.g., to an Fc domain or to one or more constant domains (e.g., CH1, CH2, or CH3). For example, the domains can be human domains or variants of human domains. The Fc domain or the one or more constant domains can be located N-terminal or C-terminal to the receptor binding agent.

Fc domains can be obtained from any suitable immunoglobulin, e.g., from a human antibody, e.g., such as an antibody of the IgG1, IgG2, IgG3, or IgG4 subtypes, IgA, IgE, IgD or IgM. In one example, the Fc domain includes a sequence from an amino acid residue at about position Cys226, or from about position Pro230, to the carboxyl terminus of the Fc domain. An Fc domain generally includes two constant domains, a CH2 domain and a CH3 domain, and optionally includes a CH4 domain. Antibodies with substitutions in an Fc region thereof and increased serum half-lives are also described in WO00/42072, WO 02/060919; Shields et al., J. Biol. Chem. 276:6591-6604 (2001); Hinton, J. Biol. Chem. 279:6213-6216 (2004)). Numbering of the residues in an IgG heavy chain is that of the EU index as in Kabat et al., Sequences of Proteins of Immunological Interest, 5th Ed. Public Health Service, NH1, MD (1991) with reference to the numbering of the human IgG1 EU antibody therein.

In one embodiment, a receptor binding agent includes a salvage receptor-binding epitope which increases in vivo serum half-life, as described, e.g., in U.S. Pat. No. 5,739,277 and Ghetie et al., Ann. Rev. Immunol. 18:739-766 (2000)). In some embodiments, the epitope is include in an Fc region that is fused to the receptor binding agent.

In one embodiment, a receptor binding agent includes a serum albumin sequence, or a portion of such sequence that binds to the FcRn receptor, or a sequence which binds to serum albumin, e.g., human serum albumin. For example, certain peptides bind to serum albumin can be associated with the receptor binding agent, e.g., the sequence DICLPRWGCLW (SEQ ID NO:22). See also, Dennis et al. J. Biol. Chem. 277:35035-35043 (2002).

Receptor binding agents can be modified to include a sequence that increases the size and stability of the agent, e.g., a sequence described in WO2008/155134 or WO2009/023270. Such sequences can be generally biologically inactive, e.g., it does not modulate signaling mediated by IL-1 cytokine family members. A variety of stabilizing polypeptide sequences can be used, e.g., sequences rich in glycine and/or serine, as well as other amino acids such as glutamate, aspartate, alanine or proline. For example, sequences can be designed to have at least 30, 40, 50, 60, 70, 80, 90 or 100% glycine and/or serine residues. In some embodiments, the combined length of stabilizing polypeptide sequences that are attached to a protein can be at least 20, 25, 35, 50, 60, 70, 80, 90, 100, 120, 140, 160, 180, 200, 250, 300, 350, 400, 500, 600, 700, 800, 900 or more than 1000 or 2000 amino acids. Stabilizing sequences can be, for example, fused to a biologically active polypeptide, for example to the N- or C-terminus of the receptor binding agent. Fusion of stabilizing sequences can result in a significant increase in the hydrodynamic radius of the fusion protein relative to the unmodified protein, which can be detected by ultracentrifugation, size exclusion chromatography, or light scattering, for example. In some embodiments, stabilizing sequences to contain few or none of the following amino acids: cysteine (to avoid disulfide formation and oxidation), methionine (to avoid oxidation), asparagine and glutamine (to avoid desamidation) and aspartate. Stabilizing sequences can be designed to contain proline residues that tend to reduce sensitivity to proteolytic degradation.

Binding Assays

The interaction of a receptor binding agent and its targets can be analyzed using any suitable approach, including for example radio-immunoassays, cell binding assays, and surface plasmon resonance (SPR). An exemplary cell binding assay using radio-iodinated protein competition is described in Boraschi, J. Immunol., 155(10):4719-25 (1995).

SPR or Biomolecular Interaction Analysis (BIA) can detect biospecific interactions in real time and without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in Raether, 1988, Surface Plasmons Springer Verlag; Sjolander and Urbaniczky, 1991, Anal. Chem. 63:2338-2345; Szabo et al., 1995, Curr. Opin. Struct. Biol. 5:699-705 and on-line resources provide by BIAcore International AB (Uppsala, Sweden). A BIACORE® system or a Reichert SR7000DC Dual Channel SPR can be used to compare and rank interactions in real time, in terms of kinetics, affinity or specificity without the use of labels. Binding affinities of a receptor binding agent for a cytokine receptor extracellular domain (e.g., the extracellular domain of IL-1RI) can be measured using SPR under approximately physiological conditions, e.g., 10 mM HEPES pH 7.4, 150 mM NaCl, 3 mM EDTA, 0.005% Tween-20. Other methods that do not rely on SPR can also be used, e.g., to measure binding and affinity.

Information from binding assays can be used to provide an accurate and quantitative measure of the equilibrium dissociation constant ($K_D$), and kinetic parameters (e.g., $K_{on}$ and $K_{off}$) for the binding of a receptor binding agent to a target. Such data can be used to compare different proteins, targets, and conditions. This information can also be used to develop structure-activity relationships (SAR). For example, the kinetic and equilibrium binding parameters of variant proteins can be compared to the parameters of a reference or parent protein. Variant amino acids at given positions can be identified that correlate with particular binding parameters, e.g., high affinity and slow $K_{off}$. This information can be combined with structural modeling (e.g., using homology modeling, energy minimization, or structure determination by x-ray crystallography or NMR).

Proteins used for evaluating affinities can be produced in recombinant form and can include tags suitable for purification or immobilization, e.g., a FLAG tag, myc tag, hemagglutinin tag, His tag, or Fc domain fusion. Extracellular domains of receptor proteins (such as IL-1RI, and IL-1RAcP) can be produced in recombinant form by expression, e.g., in bacterial or insect cells, for example, using baculovirus expression in Sf9 cells. Soluble receptor proteins can be immobilized in the BIAcore system, e.g., using chips that include reagents that bind to their tags, for example, a chip coated with IgG specific for the Fc domain or other tag.

Cellular Activity Assays

The ability of receptor binding agents to function as receptor antagonists can be evaluated, e.g., in a cell based assay. For example, it is possible to evaluate IL-1RI inhibition by a receptor binding agent. Several exemplary assays for IL-1 activity are described in Boraschi et al. and include T cell proliferation assays, IL-6 and IL-8 production assays, and inhibition of calcium influx.

In one exemplary assay, the ability of a receptor binding agent is evaluated for its ability to inhibit IL-1β stimulated release of IL-6 from human fibroblasts. Inhibition of IL-1β-stimulated cytokine release in MRC5 cells is correlated with the agent's ability to inhibit IL-1 mediated activity in vivo. Details of the assay are described in Dinarello et al., Current Protocols in Immunology, Ch. 6.2.1-6.2.7, John Wiley and Sons Inc., 2000. Briefly, human MRC5 human fibroblasts (ATCC #CCL-171, Manassas Va., USA) are grown to confluency in multi-well plates. Cells are treated with titrated doses of the receptor binding agent and controls. Cells are subsequently contacted with 100 pg/ml of IL-1β in the presence of the titrated agent and/or controls. Negative control cells are not stimulated with IL-1β. The amounts of IL-6 released in each group of treated cells is measured using an IL-6 ELISA kit (e.g., BD Pharmingen, Franklin Lakes, N.J., USA). Controls that can be used include buffer alone, IL-1Ra, and antibodies to IL-1β.

Efficacy of a receptor binding agent can also be evaluated in vivo. An exemplary assay is described in Economides et al., Nature Med., 9:47-52 (2003). Briefly, mice are injected intraperitoneally with titrated doses of the receptor binding agent and controls. Twenty-four hours after injection, mice are injected subcutaneously with recombinant human IL-1β at a dose of 1 μg/kg. Two hours after injection of the IL-1β (peak IL-6 response time), mice are sacrificed, and blood is collected and processed for serum. Serum IL-6 levels are assayed by ELISA. Percent inhibition can be calculated based on the ratio of IL-6 detected in experimental animal serum to IL-6 detected in controls.

Other exemplary assays for IL-1 activity in vivo are described in Boraschi et al. and include an anorexia, hypoglycemia, and neutrophilia assay.

Production

Receptor binding agents can be produced by expression in recombinant host cells, but also by other methods such as in vitro transcription and translation and chemical synthesis.

For cellular expression, one or more nucleic acids (e.g., cDNA or genomic DNA) encoding a receptor binding agent may be inserted into a replicable vector for cloning or for expression. Various vectors are publicly available. The vector may, for example, be a plasmid, cosmid, viral genome, phagemid, phage genome, or other autonomously replicating sequence. The appropriate coding nucleic acid sequence may be inserted into the vector by a variety of procedures. For example, appropriate restriction endonuclease sites can be engineered (e.g., using PCR). Then restriction digestion and ligation can be used to insert the coding nucleic acid sequence at an appropriate location. Vector components generally include one or more of an origin of replication, one or more marker genes, an enhancer element, a promoter, and a transcription termination sequence.

The receptor binding agent may be produced recombinantly either in isolation but also by fusion to one or more other components, such as a signal sequence, an epitope or purification moiety, and a label. The receptor binding agent can include the pro domain of an interleukin-1 family member, e.g., which subsequently can be removed by proteolytic processing.

For bacterial expression, the receptor binding agent can be produced with or without a signal sequence. For example, it can be produced within cells so that it accumulates in inclusion bodies, or in the soluble fraction. It can also be secreted, e.g., by addition of a prokaryotic signal sequence, e.g., an appropriate leader sequence such as from alkaline phosphatase, penicillinase, or heat-stable enterotoxin II. Exemplary bacterial host cells for expression include any transformable *E. coli* K-12 strain (such as *E. coli* BL21, C600, ATCC 23724; *E. coli* HB101 NRRLB-11371, ATCC-33694; *E. coli* MM294 ATCC-33625; *E. coli* W3110 ATCC-27325), strains of *B. subtilis, Pseudomonas*, and other bacilli. Proteins produced in bacterial systems will typically lack glycosylation. Accordingly, in some embodiments, the receptor binding agents described herein are substantially free of glycosylation, e.g., free of glycosylation modifications of a mammalian or other eukaryotic cell.

The receptor binding agent can be expressed in a yeast host cell, e.g., *Saccharomyces cerevisiae, Schizosaccharomyces pombe, Hanseula*, or *Pichia pastoris*. For yeast expression, the receptor binding agent can also be produced intracellularly or by secretion, e.g., using the yeast invertase leader or alpha factor leader (including *Saccharomyces* and *Kluyveromyces* forms), or the acid phosphatase leader, or the *C. albicans* glucoamylase leader (EP 362,179 published 4 Apr. 1990). In mammalian cell expression, mammalian signal sequences may be used to direct secretion of the protein, such as signal sequences from secreted polypeptides of the same or related species, as well as viral secretory leaders. Alternatively, the receptor binding agent can be produced with a pro domain of an interleukin-1 family member, e.g., an IL-1α or IL-1β pro domain.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria; the 2μ plasmid origin is suitable for yeast; and various viral origins (SV40, polyoma, adenovirus, VSV or BPV) are useful for cloning vectors in mammalian cells.

Expression and cloning vectors typically contain a selection gene or marker. Typical selection genes encode proteins that (a) confer resistance to antibiotics or other toxins, e.g., ampicillin, neomycin, methotrexate, or tetracycline, (b) complement auxotrophic deficiencies (such as the URA3 marker in *Saccharomyces*), or (c) supply critical nutrients not available from complex media, e.g., the gene encoding D-alanine racemase for Bacilli. Various markers are also available for mammalian cells, e.g., DHFR or thymidine kinase. DHFR can be used in conjunction with a cell line (such as a CHO cell line) deficient in DHFR activity, prepared and propagated as described by Urlaub et al., Proc. Natl. Acad. Sci. USA, 77:4216 (1980).

Expression and cloning vectors usually contain a promoter operably linked to the nucleic acid sequence encoding the receptor binding agent to direct mRNA synthesis. Exemplary promoters suitable for use with prokaryotic hosts include the β-lactamase and lactose promoter systems (Chang et al., Nature, 275:615 (1978); Goeddel et al., Nature, 281:544 (1979)), alkaline phosphatase, a tryptophan (trp) promoter system (Goeddel, Nucleic Acids Res., 8:4057 (1980); EP 36,776), and hybrid promoters such as the tac promoter (deBoer et al., Proc. Natl. Acad. Sci. USA, 80:21-25 (1983)). Promoters for use in bacterial systems can also contain an appropriately located Shine-Dalgarno sequence. The T7 polymerase system can also be used to drive expression of a nucleic acid coding sequence placed under control of the T7 promoter. See, e.g., the pET vectors (EMD Chemicals, Gibbstown N.J., USA) and host cells, e.g., as described in Novagen User Protocol TB053 available from EMD Chemicals and U.S. Pat. No. 5,693,489. For example, such vectors can be used in combination with BL21(DE3) cells and BL21(DE3) pLysS cells to produce protein, e.g., at least 0.05, 0.1, or 0.3 mg per ml of cell culture. Other cells lines that can be used include DE3 lysogens of B834, BLR, HMS174, NovaBlue, including cells bearing a pLysS plasmid.

Exemplary promoters for use with yeast cells include the promoters for 3-phosphoglycerate kinase (Hitzeman et al., J. Biol. Chem., 255:2073 (1980)) or other glycolytic enzymes (Hess et al., J. Adv. Enzyme Reg., 7:149 (1968); Holland, Biochemistry, 17:4900 (1978)), such as enolase, glyceraldehyde-3-phosphate dehydrogenase, hexokinase, pyruvate decarboxylase, phosphofructokinase, glucose-6-phosphate isomerase, and pyruvate kinase. Other exemplary yeast promoters are inducible and have the additional advantage of transcription controlled by growth conditions. Examples of inducible promoters include the promoter regions for alcohol dehydrogenase 2, isocytochrome C, acid phosphatase, metallothionein, and enzymes responsible for maltose and galactose utilization.

Expression of mRNA encoding a receptor binding agent from vectors in mammalian host cells can controlled, for example, by promoters obtained from the genomes of viruses such as polyoma virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters. Heterologous promoter systems can also be used, e.g., promoters responsive to tetracycline. See Urlinger, S., et al. (2000) Proc. Natl. Acad. Sci. USA 97(14):7963-7968. Transcription can also be driven by an enhancer sequence, located in cis or trans. Exemplary mammalian enhancer sequences include those for globin, elastase, albumin, α-fetoprotein, and insulin. Additional examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the coding sequence for the receptor binding agent, but is preferably located at a site 5' from the promoter.

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the receptor binding agent. The expression vector may also include one or more intronic sequences.

The receptor binding agent can also be expressed in insect cells, e.g., Sf9 or SF21 cells, e.g., using the pFAST-BAC™ system. Additional exemplary baculovirus expression vectors are available from Invitrogen, Life Technologies, Carlsbad Calif., USA. The receptor binding agent can also be expressed in mammalian cells. For example, cell lines of mammalian origin also may be employed. Examples of mammalian host cell lines include the COS-7 line of monkey kidney cells (ATCC CRL 1651) (Gluzman et al., Cell 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (EMBO J. 10: 2821, 1991). Established methods for introducing DNA into mammalian cells have been described (Kaufman, R. J., Large Scale Mammalian Cell Culture, 1990, pp. 1569).

Still other methods, vectors, and host cells suitable for adaptation to the synthesis of receptor binding agent in recombinant cells are described in Molecular Cloning: A Laboratory Manual, Third Ed., Sambrook et al. (eds.), Cold Spring Harbor Press, (2001) (ISBN: 0879695773).

Once expressed in cells, receptor binding agents can be recovered from culture medium, inclusion bodies, or cell lysates. Cells can be disrupted by various physical or chemical means, such as freeze-thaw cycling, sonication, mechanical disruption, or cell lysing agents (e.g., detergents).

Receptor binding agents can be purified from other cell proteins or polypeptides that can be found in cell lysates or in the cell medium. Various methods of protein purification may be employed and such methods are known in the art and described for example in Deutscher, Methods in Enzymology, 182 (1990); and Scopes, Protein Purification: Principles and Practice, Springer-Verlag, New York (2010) (ISBN: 1441928332). Exemplary of purification procedures include: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and affinity columns (e.g., metal chelating columns to bind epitope-tagged forms of the protein and columns with various ligands to bind any purification moiety that is associated with the receptor binding agent). A purification method can include a combination of two different ion-exchange chromatography steps, e.g., cation exchange chromatograph followed by anion exchange chromatography, or vice versa. Receptor binding agents can be eluted from ion exchange resin by a variety of methods include salt and/or pH gradients or steps. In some embodiments, the receptor binding agent includes a purification moiety (such as epitope tags and affinity handles). Such moieties can be used for affinity chromatography and can be optionally removed by proteolytic cleavage.

Ion exchange chromatography may also be used as an ion exchange separation technique. Ion exchange chromatography separates molecules based on differences between the overall charge of the molecules and can be used to separate intact form of receptor binding agents from other forms of such proteins.

Anionic or cationic substituents may be attached to matrices in order to form anionic or cationic supports for chromatography. Anionic exchange substituents include diethylaminoethyl (DEAE), quaternary aminoethyl (QAE) and quaternary amine (Q) groups. Cationic substitutents include carboxymethyl (CM), sulfoethyl (SE), sulfopropyl (SP), phosphate (P) and sulfonate (S). Cellulose ion exchange resins such as DE23, DE32, DE52, CM-23, CM-32 and CM-52 are available from Whatman Ltd. (Maidstone, Kent, U.K). SEPHADEX™ and other cross-linked ion exchangers are also known. For example, DEAE-, QAE-, CM-, and SP-SEPHADEX™ and DEAE-, Q-, CM- and S-SEPHAROSE™ and SEPHAROSE™ Fast Flow are available from Pharmacia AB. DEAE and CM derivatized ethylene glycolmethacrylate copolymer such as TOYOPEARL DEAE-6505 or M and TOYOPEARL CM-650S or M are available from Toso Haas Co. (Philadelphia, Pa., USA).

A cation exchange surface is an ion exchange surface with covalently bound negatively charged ligands, and which thus has free cations for exchange with cations in a solution in contact with the surface. Exemplary surfaces include cation exchange resins, such as those wherein the covalently bound groups are carboxylate or sulfonate. Commercially available cation exchange resins include CMC-cellulose, SP-Sephadex™ and Fast S-Sepharose™ (Pharmacia).

An anion exchange surface is an ion exchange surface with covalently bound positively charged groups, such as quaternary amino groups. An exemplary anion exchange surface is an anion exchange resin, such as DEAE cellulose, TMAE, QAE Sephadex™ and Fast Q Sepharose™ (Pharmacia).

An exemplary purification scheme for a receptor binding agent includes lysing E. coli cells in lysis buffer following by depth filtration. The material is then subject to cation exchange chromatography (CEX). The CEX eluate is then flowed over anion exchange media in an anion exchange chromatography (AEX) step. The AEX FT can be subject to a polishing step. Material can then be processed by ultrafiltration/diafiltration, e.g., to concentrate or desalt the material. Ultrafiltration/diafiltration membranes may be selected based on nominal molecular weight cut-off ("NMWCO") so as to retain the protein in the retentate, while allowing low molecular weight materials such as salts to pass into the filtrate. Any buffering solution or sterile water may be used during the final buffer exchange step, e.g., depending on the desired final pH and conductivity of the product.

A receptor binding agent can be stored in a variety of solutions, including water, PBS, and buffered solutions. Exemplary buffered solutions include sodium acetate pH 4.5, sodium acetate pH 4.7, sodium acetate pH 4.9, sodium acetate pH 5.1, sodium acetate pH 5.3, sodium acetate pH 5.5, succinate pH 5.2, succinate pH 5.4, succinate pH 5.6, succinate pH 5.8, histidine pH 5.7, histidine pH 6.0, histidine pH 6.3, histidine 6.6, sodium phosphate pH 6.5, sodium phosphate pH 6.7, sodium phosphate 7.0, sodium phosphate pH 7.3, sodium phosphate pH 7.7, imidazole pH 6.5, imidazole pH 6.8, imidazole pH 7.2, Tris pH 7.0, Tris pH 7.5, Tris pH 7.7. Buffering agents can be present, e.g., at a concentration of about 1-100 mM, 5-50 mM, 10-50 mM, or 5-25 mM. The solution can further include a salt such as NaCl (e.g., 50 mM, 150 mM, or 250 mM, and ranges therebetween), arginine (e.g., at about 1%, 2%, 3%, 4%, 5%, 7.5%, and ranges therebetween), sucrose (e.g., at about 1%, 2%, 3%, 4%, 5%, 7.5%, 8.5%, 10%, 15%, and ranges therebetween), and/or glycerol (e.g., at about 0.5%, 1%, 2%, 3%, 4%, 5%, 7.5%, 8.5%, 10%, 15%, and ranges therebetween).

The receptor binding agent can be present in the composition in an amount of at least 50 mg, 100 mg, 500 mg, 1 g, 5 g, 10 g, or more.

Analytical Methods

Host cell proteins (HCP) refer to proteins in a preparation that differ from a receptor binding agent, and for example are endogenous proteins of the host cell from which the receptor binding agent was prepared, typically E. coli proteins. Preferably, host cell proteins are present at fewer than 10000, 1000, 900, 800, or 700 ppm (parts per million). HCP can be detected, for example, by ELISA or other detection methods. For example, the ELISA can use polyclonal antibodies to HCPs. An exemplary kit is available from Cygnus Technologies (CN# F410; Southport N.C. USA). Another exemplary kit uses AlphaScreen technology (AlphaLisa® E. coli HCP Kit, Product Number AL261 C/F, Perkin Elmer, Waltham Mass. USA).

Material containing or potentially containing a receptor binding agent can be evaluated, e.g., using high pressure liquid chromatography. Exemplary analytical techniques include weak cation exchange high performance liquid chromatography (wCEX-HPLC), size exclusion high performance liquid chromatography (SE-HPLC), reverse phase liquid chromatography, ESI-MS, turbospray ionization mass spectrometry, nanospray ionization mass spectrometry, thermospray ionization mass spectrometry, sonic spray ionization mass spectrometry, SELDI-MS and MALDI-MS.

In several embodiments, the N-terminal region of a receptor binding agent includes sequences identical to peptides from the N-terminal region of IL-1β, for example, the peptide APVRS (SEQ ID NO:58). Recombinant cells (particularly E. coli cells) expressing such proteins can produce intact protein as well as other isoforms, including the des-Ala isoform and an isoform with an additional methionine (e.g., N-terminal to Ala1). Receptor binding agents that include a proline at amino acid position 2 (where the N terminal residue is at position 1) can be susceptible to cleavage by E. coli proteases, such as aminopeptidase P which has cleavage specificity for X-PRO. This cleavage can remove the N-terminal amino acid. For example, P03, P04, and P05 have a proline at position 2. The intact forms of P03, P04, and P05 are 153 amino acids in length and begin with alanine whereas the des-Ala species are 152 amino acids in length and begin with proline.

Analytical techniques such as those above can be used to distinguish between intact forms and other forms, e.g., a des-Ala species. An analytical exemplary technique is wCEX-HPLC. For example, P05 can be evaluated using a Dionex ProPac® WCX-10 4×250 mm column (Product Number 054993) as described in Example 9 below. WCX-HPLC peaks can be evaluated by C4 reversed-phase (RP)-HPLC on-line with mass spectrometry. Intact P05 has theoretical mass: 17700.4 Da and is detectable as 17700.4 Da. The des-Ala species is detectable as 17629.4 Da, which is 71 Da less than the mass of the intact P05. The 71 Da reduction in mass corresponds to removal of a single alanine residue.

Pharmaceutical Compositions

A receptor binding agent can be formulated as a pharmaceutical composition. Typically, the composition is sterile and includes one or more of a buffer, a pharmaceutically acceptable salt, and an excipient or stabilizer. For example, the composition can be an aqueous composition. A receptor binding agent described herein can be formulated according to standard methods for a biologic. See e.g., Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); Kibbe (ed.), Handbook of Pharmaceutical Excipients, 3rd ed. (2000) (ISBN: 091733096X); Protein formulation and delivery, McNally and Hastedt (eds.), Informa Health Care (ISBN: 0849379490) (2007).

A receptor binding agent for a pharmaceutical composition is typically at least 10, 20, 50, 70, 80, 90, 95, 98, 99, or 99.99% pure and typically free of human proteins. It can be the only protein in the composition or the only active protein in the composition. It can also be combined with one or more other active proteins, e.g., one or more other purified active proteins, e.g., a related or unrelated protein. In some embodiments, the composition can contain the receptor binding agent at a concentration of between about 0.001-10%, e.g., 0.001-0.1%, 0.01-1%, or 0.1%-10%.

Accordingly, also featured herein are purified and isolated forms of the agents described herein. The term "isolated" refers to material that is removed from its original environment (e.g., the cells or materials from which the receptor binding agent is produced). Pharmaceutical compositions can be substantially free of pyrogenic materials, substantially free of nucleic acids, and/or substantially free of cellular enzymes and components, such as polymerases, ribosomal proteins, and chaperone proteins.

A pharmaceutical composition can include a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19), e.g., acid addition salts and base addition salts.

In one embodiment, the receptor binding agent is formulated with one or more excipients, such as sodium chloride, and a phosphate buffer (e.g., sodium dibasic phosphate heptahydrate, sodium monobasic phosphate), and polysorbate. It can be provided, for example, in a buffered solution, e.g., at a concentration of about 5-100, 5-30, 30-50, or 50-100 mg/ml and can be stored at 2-8° C. Pharmaceutical compositions may also be in a variety of other forms. These include, for example, liquid, semi-solid and solid dosage forms, such as liquid solutions (e.g., injectable and infusible solutions), dispersions or suspensions, and liposomes. The preferred form can depend on the intended mode of administration and therapeutic application. Compositions for the agents described herein are typically in the form of injectable or infusible solutions, or are for topical or ocular delivery (see below).

Pharmaceutical compositions typically are sterile and stable under the conditions of manufacture and storage. A pharmaceutical composition can also be tested to ensure it meets regulatory and industry standards for administration. The composition can be formulated as a solution, microemulsion, dispersion, liposome, or other ordered structure suitable to high drug concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be engineered by inclusion of an agent that delays absorption, for example, monostearate salts and gelatin.

For example, a receptor binding agent can be associated with a polymer, e.g., a substantially non-antigenic polymer, such as a polyalkylene oxide or a polyethylene oxide. In some embodiments, the polymer covalently attached to the receptor binding agent, e.g., directly or indirectly. Suitable polymers will vary substantially by weight. Polymers having molecular number average weights ranging from about 200 to about 35,000 Daltons (or about 1,000 to about 15,000, and 2,000 to about 12,500) can be used. For example, a receptor binding agent can be conjugated to a water soluble polymer, e.g., a hydrophilic polyvinyl polymer, e.g. polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides that include the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparan.

In certain embodiments, the receptor binding agent may be prepared with a carrier that will protect the compound against rapid release. It may be delivered as a controlled release formulation, delivered by an implant or a microencapsulated delivery system. Biodegradable, biocompatible polymers can be used, such as ethylene vinyl acetate, polyanhydrides, polyglycolic acid, collagen, polyorthoesters, and polylactic acid. See generally e.g., Sustained and Controlled Release Drug Delivery Systems, J. R. Robinson, ed., Marcel Dekker, Inc., New York, 1978.

Administration

A receptor binding agent can be administered to a subject, e.g., a human subject, by a variety of methods, such as intravenous administration as a bolus or by continuous infusion over a period of time, by intramuscular, intramuscular, intraarterial, intrathecal, intracapsular, intraorbital, intracardiac, intradermal, intraperitoneal, intrasynovial, transtracheal, subcutaneous, subcuticular, intraarticular, subcapsular, subarachnoid, intraspinal, epidural injection, intrasternal injection and infusion. Still other modes of administration include topical (e.g., dermal or mucosal) or inhalation (e.g., intranasal or intrapulmonary) routes. For many applications, the route of administration is one of: intravenous injection or infusion, subcutaneous injection, or intramuscular injection.

A receptor binding agent can be administered as a fixed dose or in a mg/kg dose. It can be administered intravenously (IV) or subcutaneously (SC). The receptor binding agent can administered, for example, every day, every other day, every third, fourth or fifth day, every week, every three to five weeks, e.g., every fourth week, or monthly.

A pharmaceutical composition may include a "therapeutically effective amount" of an agent described herein. A therapeutically effective amount of an agent may vary according to factors such as the disease state, age, sex, and weight of the individual, and the ability of the compound to elicit a desired response in the individual, e.g., amelioration of at least one disorder parameter, or amelioration of at least one symptom of the disorder (and optionally the effect of any additional agents being administered). A therapeutically effective amount is also one in which any toxic or detrimental effects of the composition are outweighed by the therapeutically beneficial effects. A receptor binding agent is typically administered in a therapeutically effective amount.

Pharmaceutical compositions can be administered using medical devices, e.g., implants, infusion pumps, hypodermic needles, and needleless hypodermic injection devices. The device can include, e.g., one or more housings for storing pharmaceutical compositions, and can be configured to deliver unit doses of the receptor binding agent, and optionally a second agent. The doses can be fixed doses, i.e., physically discrete units suited as unitary dosages for the subjects to be treated; each unit can contain a predetermined quantity of receptor binding agent calculated to produce the desired therapeutic effect in association with a pharmaceutical carrier and optionally in association with another agent.

In some embodiments, to treat a disorder described herein, a receptor binding agent can be administered to the subject having the disorder in an amount and for a time sufficient to induce a sustained improvement in at least one indicator that reflects the severity of the disorder. An improvement is considered "sustained" if the subject exhibits the improvement on at least two occasions separated by one to four weeks. The degree of improvement can be determined based on signs or symptoms, and can also employ questionnaires that are administered to the subject, such as quality-of-life questionnaires.

Various indicators that reflect the extent of the illness may be assessed for determining whether the amount and time of the treatment is sufficient. The baseline value for the chosen indicator or indicators is established by examination of the subject prior to administration of the first dose of the receptor binding agent. Preferably, the baseline examination is done within about 60 days of administering the first dose.

Improvement can be induced by repeatedly administering a dose of the receptor binding agent until the subject manifests an improvement over baseline for the chosen indicator or indicators. In treating chronic conditions, the degree of improvement may be obtained by repeated administration over a period of at least a month or more, e.g., for one, two, or three months or longer, or indefinitely. In treating an acute condition, the agent can be administered for a period of one to six weeks or even a single dose.

Although the extent of illness after treatment may appear improved according to one or more indicators, treatment may be continued indefinitely at the same level or at a reduced dose or frequency. Treatment may also be discontinued, e.g., upon improvement or disappearance of symptoms. Once treatment has been reduced or discontinued, it may be resumed if symptoms should reappear.

Treatments

A receptor binding agent such as one that binds to IL-1RI and that antagonizes IL-1 signaling, can be used to treat an "IL-1 mediated disorder," which includes any disease or medical condition that is (i) caused at least in part by IL-1 agonism, (ii) is associated with elevated levels or activity of an IL-1 signaling component (such as IL-1α, IL-1β, or IL-1RI) or elevated IL-1 signaling, and/or (iii) is ameliorated by decreasing IL-1 activity. IL-1 mediated disorders include acute and chronic disorders, including autoimmune disorders and inflammatory disorders. IL-1 mediated disorders include systemic and non-systemic disorders. It is well established that IL-1α and IL-1β are potent pro-inflammatory cytokines implicated in infectious responses as well as in inflammatory disease, including rheumatoid arthritis. Increased IL-1 production has been observed in patients with several autoimmune disorders, ischemia, and various cancers, therefore implicating IL-1 in these and related diseases.

See also generally Sims and Smith, The IL-1 family: regulators of immunity, Nature Reviews Immunology, doi: 10.1038/nri2691 (2010).

The term "treat" refers to the administration of an agent described herein to a subject, e.g., a patient, in an amount, manner, and/or mode effective to improve a condition, symptom, or parameter associated with a disorder, e.g., a disorder described herein, or to prevent progression of a disorder, to either a statistically significant degree or to a degree detectable to one skilled in the art. The treatment can be to intended to cure, heal, alleviate, relieve, alter, remedy, ameliorate, palliate, improve or affect the disorder, the symptoms of the disorder or the predisposition toward the disorder. An effective amount, manner, or mode can vary depending on the subject and may be tailored to the subject. Exemplary subjects include humans, primates, and other non-human mammals. A receptor binding agent can also be given prophylactically to reduce the risk of the occurrence of a disorder or symptom thereof.

The IL-1 mediated disorder can be an autoimmune disorder. Examples of IL-1 mediated autoimmune disorders include: rheumatoid arthritis, ankylosing spondylitis, Behcet's syndrome, inflammatory bowel diseases (including Crohn's disease and ulcerative colitis), asthma, psoriasis, Type I diabetes, and other disorders identified herein. A receptor binding agent described herein can be administered to a subject having or at risk for such IL-1 mediated autoimmune disorders. The IL-1 mediated disorder can be an inflammatory disorder such as described below. A receptor binding agent described herein can be administered to a subject having or at risk for such IL-1 mediated inflammatory disorders.

Exemplary IL-1 mediated disorders include:

Rheumatoid Arthritis and Related Arthritides.

A receptor binding agent can be used to treat a subject having or at risk for rheumatoid arthritis. Rheumatoid arthritis (RA) is a chronic systemic autoimmune inflammatory disease that affects the synovial membrane in joints and which damages articular cartilage. The pathogenesis of RA is T lymphocyte dependent and can include the production of autoantibodies known as rheumatoid factors. Complexes of rheumatoid factor and antigen can form and accumulate in joint fluid and blood, inducing the infiltration of lymphocytes, neutrophils, and monocytes into the synovium. Joints are typically affected in a symmetrical pattern, but extra-articular disease may also occur, e.g., causing pulmonary fibrosis, vasculitis, and cutaneous ulcers, or Felty's syndrome which manifests as neutropenia, thrombocytopenia and splenomegaly. Patients can also exhibit rheumatoid nodules in the area of affected joints, pericarditis, pleuritis, coronary arteritis, and interstitial pneumonitis with pulmonary fibrosis. A form of IL-1Ra is indicated for moderately to severely active RA. See, e.g., Cohen, S. et al. Arthritis & Rheumatism 46, 614-24 (2002); Fleischmann, R. M. et al. Arthritis & Rheumatism 48, 927-34 (2003); Nuki, G., et al. Arthritis & Rheumatism 46, 2838-46 (2002); Schiff, M. H. et al. Arthritis & Rheumatism 50, 1752-60 (2004).

Symptoms of active RA include fatigue, lack of appetite, low grade fever, muscle and joint aches, and stiffness. Muscle and joint stiffness are usually most notable in the morning and after periods of inactivity. During flares, joints frequently become red, swollen, painful, and tender, generally as a consequence of synovitis. Scales useful for assessing RA and symptoms of RA include the Rheumatoid Arthritis Severity Scale (RASS; Bardwell et al., (2002) Rheumatology 41(1):38-45), SF-36 Arthritis Specific Health Index (ASHI; Ware et al., (1999) Med. Care. 37(5 Suppl): MS40-50), Arthritis Impact Measurement Scales or Arthritis Impact Measurement Scales 2 (AIMS or AIMS2; Meenan et al. (1992) Arthritis Rheum. 35(1):1-10); the Stanford Health Assessment Questionnaire (HAQ), HAQII, or modified HAQ (see, e.g., Pincus et al. (1983) Arthritis Rheum. 26(11):1346-53).

A receptor binding agent described herein can be administered to a subject having or at risk for RA to delay onset and/or ameliorate one or more of the foregoing signs and symptoms. The subject can have moderate to severe active RA. The subject can be a non-responder to TNF inhibitor therapy (e.g., therapy with ENBREL® (etanercept), HUMIRA® (adalimumab), or REMICADE® (infliximab)); the subject can have previously been administered a TNF inhibitor; or the subject can also be continuing to receive a TNF inhibitor (and responding or not responding).

The subject can also be administered methotrexate. The subject can be administered one or more other DMARDS (disease modifying anti-rheumatic drugs), a corticosteroid, and/or a non-steroidal anti-inflammatory. Still other drugs which can be co-administered with a receptor binding agent include inhibitors of CD28 (e.g., CTLA4-Ig), inhibitors of RANKL, IFNγ, IL-6, IL-8, and IL-17. Inhibitors include antibodies to such mediators, soluble receptors specific for such mediators, and/or antibodies to receptors for such mediators.

Juvenile Chronic Arthritis.

A receptor binding agent can be used to treat juvenile chronic arthritis, e.g., in a subject that is less than 21, 18, 17, 16, 15, or 14 years of age. Juvenile chronic arthritis resembles RA in several respects. Subjects can be rheumatoid factor positive. Subjects may have pauciarticular, polyarticular, or systemic forms of the disease. The arthritis can cause joint ankylosis and retarded growth and can also lead to chronic anterior uveitis and systemic amyloidosis. A receptor binding agent can be used delay onset of or ameliorate one or more such symptoms.

A receptor binding agent can be used to treat juvenile idiopathic arthritis, including systemic onset juvenile idiopathic arthritis (SO-JIA). Subjects may have failed prior corticosteroid treatment or required corticosteroid treatment at a daily dose equal to or over 0.3 mg/kg. See e.g., Quartier et al. (2011) Ann Rheum Dis. 70(5):747-54.

Other Rheumatic Disorders.

A receptor binding agent described herein can also be used to treat other rheumatic disorders including scleroderma, systemic lupus erythematosus, gout, osteoarthritis, polymyalgia rheumatica, psoriatic arthritis and chronic Lyme arthritis, inflammation of the voluntary muscle and other muscles, including dermatomyositis, inclusion body myositis, polymyositis, and lymphangioleimyomatosis, pyrogenic arthritis syndrome, pediatric granulomatous arthritis (PGA)/Blau syndrome, and other rheumatic disorders discussed herein.

A receptor binding agent can be used to treat metabolic rheumatic disorders, e.g., disorders associated with hyperuricemia, e.g., gout including chronic acute gout, and other crystal-mediated arthropathies. The agent can be used to treat drug-induced flares associated with gout, including for example flares induced by xanthine oxidase inhibitors, urate oxidase, or uricosuric agents. In gout, crystals of uric acid can activate the inflammasome and trigger the release of IL-1β.

Spondyloarthropathies.

A receptor binding agent can be used to treat spondyloarthropathies, which include disorders such as ankylosing spondylitis, Reiter's syndrome, arthritis associated with inflammatory bowel disease, spondylitis associated with psoriasis, juvenile onset spondyloarthropathy and undifferentiated spondyloarthropathy. Spondyloarthropathies are frequently associated with the HLA-B27 gene. Subjects may lack rheumatoid factor and may exhibit sacroileitis with or without spondylitis and inflammatory asymmetric arthritis. Subjects may also have ocular inflammation (see below).

Scleroderma.

A receptor binding agent can be used to treat scleroderma or systemic sclerosis. Scleroderma is characterized by induration of the skin which may be localized or systemic. Vascular lesions and endothelial cell injury in the microvasculature can also be present. Subjects may exhibit mononuclear cell infiltrates in the cutaneous lesions and have anti-nuclear antibodies. Other organs that show pathogenesis can include: the gastrointestinal tract which may have smooth muscle atrophy and fibrosis resulting in abnormal peristalsis/motility; the kidney which may have concentric subendothelial intimal proliferation affecting small arcuate and interlobular arteries with resultant reduced renal cortical blood flow, and which can cause proteinuria, azotemia and hypertension; skeletal muscle which may involve atrophy, interstitial fibrosis, inflammation, lung, interstitial pneumonitis and interstitial fibrosis; and heart which can exhibit, e.g., contraction band necrosis and scarring/fibrosis. A receptor binding agent described herein can be administered to a subject having or at risk for scleroderma to ameliorate one or more of the foregoing signs and symptoms.

Sjögren's Syndrome.

A receptor binding agent can be used to treat Sjögren's syndrome. Sjögren's syndrome is characterized by immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions can result in keratoconjunctivitis sicca, xerostomia, with other manifestations or associations including biliary cirrhosis, peripheral or sensory neuropathy, and palpable purpura. Treatment of ocular disorders associated with Sjögren's is also discussed below.

Thyroid Disorders.

A receptor binding agent can be used to treat a thyroid disorder. Exemplary thyroid disorders include Graves' disease, Hashimoto's thyroiditis, juvenile lymphocytic thyroiditis, and atrophic thyroiditis, and are the result of an autoimmune response against thyroid antigens with production of antibodies that react with proteins present in and often specific for the thyroid gland. Experimental models are available including spontaneous models: rats (BUF and BB rats) and chickens (obese chicken strain) and inducible models created by immunization of animals with either thyroglobulin, thyroid microsomal antigen (thyroid peroxidase).

Diabetic & Metabolic Disorders.

A receptor binding agent can be used to treat a diabetic disorder such as juvenile onset diabetes (including autoimmune diabetes mellitus and insulin-dependent types of diabetes) and maturity onset diabetes (including non-insulin dependent and obesity-mediated diabetes), type I diabetes and type II diabetes. For example, type I diabetes mellitus or insulin-dependent diabetes is associated with the autoimmune destruction of pancreatic islet cells caused by autoantibodies and auto-reactive T cells. In addition, reducing IL-1β activity can improve glucose control and beta-cell function and can be used to treat type II diabetes. See e.g. Owyang et al. Endocrinology. 2010; 151(6):2515-27. For example, in some embodiments, a receptor binding agent described herein can be administered to a subject that is not being administered insulin, e.g., the subject is not insulin dependent. For example, the subject can be pre-diabetic. The subject can have either impaired glucose tolerance or impaired fasting glucose. The subject can be obese or have a body mass index that is above 23, 25, 30, 35, or 40 kg/m$^2$. The subject can be insulin resistant, and/or characterized by hyperglycemia or hyperinsulinemia. The subject can be at risk for progression to type II diabetes. See also Larsen, et al. (2007) NEJM 356:1517-26 and Larsen, et al. (2009). Diabetes Care 32:1663-8. In some embodiments, the subject has a fasting plasma glucose of greater than 6.1, 6.5, 7, or 8 mmol/L. In some embodiments, the subject has an A1C level greater than 5.5, 5.7, 6, 6.4, 7, 7.5 or 8%.

In some embodiments, the subject is also administered an insulin secretagogue, e.g., such as an sulfonylurea (e.g., chlorpropamide, tolazamide, acetohexamide, tolbutamide, glyburide, glimepiride, glipizide) and/or meglitinides (e.g., repaglinide, nateglinide) that stimulate insulin secretion. The subject can also be administered a biguanide (e.g., metformin). The receptor binding agent can be administered to reduce loss of and/or damage to pancreatic beta cells.

In some embodiments, the subject is heterozygous or homozygous for the C allele of rs4251961, located near the 5' of the gene URN.

Treatment with a receptor binding agent includes ameliorating or preventing deterioration of secondary conditions associated with diabetes, such as diabetic retinopathy, kidney transplant rejection in diabetic patients, obesity-mediated insulin resistance, and renal failure, which itself may be associated with proteinuria and hypertension.

Gastrointestinal Disorders.

Receptor binding agents described herein can be used to treat a inflammatory gastrointestinal disorder, including for example coeliac disease, Crohn's disease, ulcerative colitis, idiopathic gastroparesis pancreatitis including chronic pancreatitis, acute pancreatitis, inflammatory bowel disease and ulcers including gastric and duodenal ulcers.

Pulmonary Disorders.

A receptor binding agent can be used to treat a pulmonary disease mediated by IL-1. Exemplary pulmonary diseases that can be treated include chronic obstructive pulmonary disease (e.g. emphysema and chronic bronchitis), pulmonary alveolar proteinosis, bleomycin-induced pneumopathy and fibrosis, pulmonary fibrosis, including idiopathic pulmonary fibrosis and radiation-induced pulmonary fibrosis, pulmonary sarcoidosis, cystic fibrosis, collagen accumulation in the lungs, ARDS, broncho-pulmonary dysplasia (BPD), chronic obstructive pulmonary diseases, and chronic fibrotic lung disease of preterm infants. In addition, the receptor binding agents described herein can be used to treat occupational lung diseases, including asbestosis, coal worker's pneumoconiosis, silicosis or similar conditions associated with long-term exposure to fine particles. Inflammatory and fibrotic lung disease including eosinophilic pneumonia, idiopathic pulmonary fibrosis, and hypersensitivity pneumonitis may involve a misregulated immune-inflammatory response that can be treated using a receptor binding agent.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Cardiovascular Disorders.

A receptor binding agent described herein can be used to treat a cardiovascular disorder or injury, such as aortic aneurysms, acute coronary syndrome, arteritis, vascular occlusion, including cerebral artery occlusion, complications of coronary by-pass surgery, ischemia/reperfusion injury, heart disease, including atherosclerotic heart disease, myocarditis, including chronic autoimmune myocarditis and viral myocarditis, heart failure, including chronic heart failure, congestive heart failure, myocardial infarction, restenosis and/or atherosclerosis after heart surgery or after carotid artery balloon angioplastic procedures, silent myocardial ischemia, left ventricular pump dysfunction, post implantation complications of left ventricular assist devices, Raynaud's phenomena, thrombophlebitis, vasculitis including Kawasaki's vasculitis, veno-occlusive disease, giant cell arteritis, Wegener's granulomatosis, and Schoenlein-Henoch purpura. The receptor binding agent can also be provided prophylactically, e.g., to reduce risk of such cardiovascular disorder. In some embodiments, the receptor binding agent is administered to a patient to treat atherosclerosis or to reduce risk thereof.

IL-1 mediated signaling is activated by acute myocardial infarction and can initiate apoptotic cell death in the peri-infarct myocardial cells, extending the size of the infarct zone. A receptor binding agent described herein can be administered to reduce damage caused by myocardial infarction. For example, the receptor binding agent can be administered a subject who is at risk for a myocardial infarction, or a subject who has experienced a myocardial infarction, particularly an acute myocardial infarction, e.g., within the last 2, 4, 6, 12, 24, or 48 hours. The agent can be administered in combination with other agents, including, e.g., heparin and aspirin.

A receptor binding agent can also be used to treat stroke, sub-arachnoid hemorrhage, head trauma or brain injury, and/or inflammation associated with a cardiovascular disorder. For example, elevated levels of IL-1$\beta$ have been implicated neuroinflammation associated with stroke and brain injury (Rothwell, N. J., et al., TINS 23(12): 618-625, 2000). The receptor binding agent can be administered to reduce such inflammation and other inflammation associated with ischemia and/or hypoxia. In addition, the receptor binding agent can also be provided prophylactically, e.g., to reduce risk of such disorders and/or inflammation associated with such disorders. For example, the receptor binding agent can be administered a subject who is at risk for a stroke, an ischemic event, other cardiovascular event, or a hemorrhagic event (such as a sub-arachnoid hemorrhage), or a subject who has experienced a stroke, an ischemic event, other cardiovascular event, or a hemorrhagic event (such as a sub-arachnoid hemorrhage), e.g., within the last 2, 4, 6, 12, 24, or 48 hours.

Genitourinary and Renal Disorders.

Disorders of the genitourinary system can also be treated with a receptor binding agent described herein. Such disorders include glomerulonephritis, including autoimmune glomerulonephritis, glomerulonephritis due to exposure to toxins or glomerulonephritis secondary to infections with haemolytic streptococci or other infectious agents. Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens.

Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

A receptor binding agent can also be used to treat uremic syndrome and its clinical complications (for example, renal failure, anemia, and hypertrophic cardiomyopathy), including uremic syndrome associated with exposure to environmental toxins, drugs or other causes. Complications that arise from inflammation of the gallbladder wall that leads to alteration in absorptive function can also be treated. Included in such complications are cholelithiasis (gallstones) and choliedocholithiasis (bile duct stones) and the recurrence of cholelithiasis and choliedocholithiasis. Further conditions that can be treated are complications of hemodialysis; prostate conditions, including benign prostatic hypertrophy, nonbacterial prostatitis and chronic prostatitis; and complications of hemodialysis. A receptor binding agent can also be used to treat chronic pain conditions, such as chronic pelvic pain, including chronic prostatitis/pelvic pain syndrome, and post-herpetic pain.

Hematologic and Oncologic Disorders.

A receptor binding agent described herein can be used to treat various forms of cancer, including acute myelogenous leukemia, chronic myelogenous leukemia, Epstein-Barr virus-positive nasopharyngeal carcinoma, glioma, colon, stomach, prostate, renal cell, cervical and ovarian cancers, lung cancer (SCLC and NSCLC), including cancer-associated cachexia, fatigue, asthenia, paraneoplastic syndrome of cachexia and hypercalcemia. See, e.g., Voronov et al. (2003) PNAS 100:2645-2650. Solid tumors, including sarcoma, osteosarcoma, and carcinoma, such as adenocarcinoma (for example, breast cancer) and squamous cell carcinoma are also treatable. Regarding the role of IL-1β in certain tumors, see e.g., Krelin et al. (2007) Cancer Res. 67:1062-1071. Additional cancers include esophogeal cancer, gastric cancer, gall bladder carcinoma, leukemia, including acute myelogenous leukemia, chronic myelogenous leukemia, myeloid leukemia, chronic or acute lymphoblastic leukemia and hairy cell leukemia. Other malignancies with invasive metastatic potential, including multiple myeloma, can be treated with the receptor binding agents. See, e.g., Lust et al. (2009) Mayo Clin Proc 84(2):114-122.

A receptor binding agent can also be used to treat anemias and hematologic disorders, including chronic idiopathic neutropenia, anemia of chronic disease, aplastic anemia, including Fanconi's aplastic anemia; idiopathic thrombocytopenic purpura (ITP); thrombotic thrombocytopenic purpura, myelodysplastic syndromes (including refractory anemia, refractory anemia with ringed sideroblasts, refractory anemia with excess blasts, refractory anemia with excess blasts in transformation); myelofibrosis/myeloid metaplasia; and sickle cell vasocclusive crisis.

Autoimmune hemolytic anemia, immune pancytopenia, and paroxysmal nocturnal hemoglobinuria can result from production of antibodies that react with antigens expressed on the surface of red blood cells (and in some cases other blood cells including platelets as well) and is a consequence of the removal of those antibody coated cells via complement mediated lysis and/or ADCC/Fc-receptor-mediated mechanisms. In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

The receptor binding agent can also be administered to subjects having or at risk for various lymphoproliferative disorders, including autoimmune lymphoproliferative syndrome (ALPS), chronic lymphoblastic leukemia, hairy cell leukemia, chronic lymphatic leukemia, peripheral T-cell lymphoma, small lymphocytic lymphoma, mantle cell lymphoma, follicular lymphoma, Burkitt's lymphoma, Epstein-Barr virus-positive T cell lymphoma, histiocytic lymphoma, Hodgkin's disease, diffuse aggressive lymphoma, acute lymphatic leukemias, T gamma lymphoproliferative disease, cutaneous B cell lymphoma, cutaneous T cell lymphoma (i.e., mycosis fungoides) and Sezary syndrome.

Hepatic Disorders.

The receptor binding agents disclosed herein are also useful for treating conditions of the liver such as hepatitis, including acute alcoholic hepatitis, acute drug-induced or viral hepatitis, hepatitis A, B and C, sclerosing cholangitis, hepatic sinusoid epithelium, and inflammation of the liver due to unknown causes.

Hearing Disorders.

Receptor binding agents can also be used to treat disorders that involve hearing loss and that are associated with abnormal IL-1 expression. Such disorders include cochlear nerve-associated hearing loss that is thought to result from an autoimmune process, e.g., autoimmune hearing loss, Meniere's syndrome and cholesteatoma, a middle ear disorder often associated with hearing loss.

Bone Disorders.

Non-arthritic disorders of the bones and joints and also treatable with the receptor binding agents described herein. This encompasses inflammatory disorders of the bone or joint, osteoclast disorders that lead to bone loss, such as but not limited to osteoporosis, including post-menopausal osteoporosis, osteoarthritis, periodontitis resulting in tooth loosening or loss, and prosthesis loosening after joint replacement (generally associated with an inflammatory response to wear debris), e.g., orthopedic implant osteolysis.

Amyloid Disorders.

Further, the receptor binding agents described herein can be used to treat primary amyloidosis and the secondary amyloidosis that is characteristic of various conditions, including Alzheimer's disease, secondary reactive amyloidosis; Down's syndrome; and dialysis-associated amyloidosis. In addition, receptor binding agents can be used to treat Amyotrophic lateral sclerosis (ALS), Huntington's disease, and Parkinson's disease. These diseases can also involve formation of aggregates and amyloids that can trigger inflammatory responses.

Neurological Disorders.

Receptor binding agents can also be used to treat neuroinflammation and demyelinating diseases of the central and peripheral nervous systems, including multiple sclerosis; idiopathic demyelinating polyneuropathy or Guillain-Barre syndrome; and chronic inflammatory demyelinating polyneuropathy. These disorders are believed to have an autoimmune basis and result in nerve demyelination as a result of damage caused to oligodendrocytes or to myelin directly. In multiple sclerosis disease induction and involve T lymphocytes. Multiple sclerosis has either a relapsing-remitting course or a chronic progressive course. Lesions contain infiltrates of predominantly T lymphocyte mediated, microglial cells and infiltrating macrophages; $CD4^+$ T lymphocytes are the predominant cell type at lesions. The mechanism of oligodendrocyte cell death and subsequent demyelination is not known but is likely T lymphocyte driven.

Myopathies.

Receptor binding agents can be used to treat myopathies associated with inflammation and autoimmunity. Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Vasculitis Disorders.

A receptor binding agent described herein can be used to treat a vasculitis disorder, e.g., a systemic vasculitis. Systemic vasculitis includes diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes.

Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behcet's disease, thromboangiitis obliterans (Buerger's disease) and cutaneous necrotizing venulitis. The pathogenic mechanism of these vasculitis disorders is believed to be primarily due to the deposition of immunoglobulin complexes in the vessel wall and subsequent induction of an inflammatory response either via ADCC, complement activation, or both.

CAPS.

A receptor binding agent can be used to treat a CAPS disorder, i.e., CIAS1 Associated Periodic Syndromes. CAPS includes three genetic syndromes: Neonatal Onset Multisystem Inflammatory Disorder (NOMID), Muckle-Wells Syndrome (MWS), and Familial Cold Autoinflammatory Syndrome (FCAS). (Hoffman et al. 2001 Naure 29:301-305; Feldmann et al. 2002 Am J Hum Genet 71:198-203; Aksentijevich et al. 2002 Arthritis Rheum 46:3340-3348). CAPS are inherited in an autosomal dominant manner with a sporadic or familial pattern. CIAS1 encodes NALP3, a protein component of the "inflammasome", a subcellular enzyme complex that regulates the activity of caspase 1. Mutations in CIAS1 lead to increased production of IL-1 and numerous pathological consequences (Aksentijevich et al. 2002 supra). IL-1 strongly induces the production of acute phase reactants in the liver, such as C-reactive protein (CRP) and serum amyloid A (SAA).

CAPS disorders share common clinical features and present as a spectrum of clinical severity. NOMID is the most seriously disabling, MWS somewhat less so and FCAS is the least severe. CAPS disorders have several overlapping features and individuals can have unique constellations of signs and symptoms. Features common to all these conditions include fevers, urticaria-like rash, arthritis or arthralgia, myalgia, malaise, and conjunctivitis.

In NOMID, chronic aseptic meningitis may lead to mental retardation and these patients may also suffer disfiguring and disabling bony overgrowth at the epiphyses and patellae. These patients may also suffer blindness due to optic nerve atrophy that results from increased intracranial pressure. MWS and NOMID are commonly associated with severe inflammation that may include the auditory system, meninges, and joints. These patients may suffer daily high spiking fevers and a chronic rash that frequently changes in distribution and intensity. Patients may suffer hearing loss or deafness. Conjunctivitis and papilledema are frequently observed. Amyloidosis may develop and lead to renal failure due to chronic inflammation and overproduction of acute phase reactants (particularly SM). A receptor binding agent can be administered to a subject having NOMID, MWS, or FCAS or diagnosed as have a genotype associated with NOMID, MWS, or FCAS. In addition, a receptor binding agent can be administered to a subject having TRAPS (TNF receptor associated periodic syndrome).

Dermatological Disorders.

A receptor binding agent can be used to treat a dermatological disorder, such as an inflammatory dermatological disorder or an autoimmune or immune-mediated skin disease. An exemplary disorder is psoriasis. Additional autoimmune or immune-mediated skin disease including bullous skin diseases, erythema multiforme, and contact dermatitis are mediated by auto-antibodies, the genesis of which is T lymphocyte-dependent. Psoriasis is a T lymphocyte-mediated inflammatory disease. Lesions contain infiltrates of T lymphocytes, macrophages and antigen processing cells, and some neutrophils.

Additional disorders of the skin or mucous membranes that can be treated include acantholytic diseases, including Darier's disease, keratosis follicularis and pemphigus vulgaris. Further additional disorders include: acne, acne rosacea, alopecia areata, aphthous stomatitis, bullous pemphigoid, burns, eczema, erythema, including erythema multiforme and erythema multiforme bullosum (Stevens-Johnson syndrome), inflammatory skin disease, lichen planus, linear IgA bullous disease (chronic bullous dermatosis of childhood), loss of skin elasticity, mucosal surface ulcers, including gastric ulcers, neutrophilic dermatitis (Sweet's syndrome), dermatomyositis, pityriasis rubra pilaris, psoriasis, pyoderma gangrenosum, multicentric reticulohistiocytosis, and toxic epidermal necrolysis. Other skin related conditions treatable by receptor binding agents include dermatitis herpetiformis (Duhring's disease), atopic dermatitis, contact dermatitis, and urticaria (including chronic idiopathic urticaria).

Allergic Disorders.

A receptor binding agent can be used to treat an allergic disorder, such as asthma, allergic rhinitis, atopic dermatitis, food hypersensitivity, allergic conjunctivitis (see also below) and urticaria. These diseases are frequently mediated by T lymphocyte induced inflammation, IgE mediated-inflammation, or both.

Asthma is a chronic condition involving the respiratory system in which the airway occasionally constricts, becomes inflamed, and is lined with excessive amounts of mucus, often in response to one or more triggers. Episodes may be triggered by such things as exposure to an environmental stimulant (or allergen) such as cold air, warm air, moist air, exercise or exertion, emotional stress, and viral illness. Airway narrowing causes symptoms such as wheezing, shortness of breath, chest tightness, and coughing. A receptor binding agent can be used to treat asthma and can be formulated for topical or pulmonary delivery for such treatment or can be delivered parenterally.

Transplantation.

A receptor binding agent can be administered to a subject that is about to undergo, is undergoing, or is recovering from a transplantation. Transplantation associated diseases, including graft rejection and graft-versus-host-disease (GVHD), are T lymphocyte-dependent; inhibition of T lymphocyte function is ameliorative. Corneal transplantation can be associated with neovascularization which can be ameliorated by treatment with a receptor binding agent. A receptor binding agent can be also used to treat complications resulting from solid organ transplantation, such as heart, liver, skin, kidney, lung (lung transplant airway obliteration) or other transplants, including bone marrow transplants.

Infectious Diseases.

The receptor binding agents described herein are useful for treating protozoal diseases, including malaria and schistosomiasis and to treat erythema nodosum leprosum; bacterial or viral meningitis; tuberculosis, including pulmonary tuberculosis; and pneumonitis secondary to a bacterial or viral infection including influenza infection and infectious mononucleosis.

Also treatable with a receptor binding agent are inherited periodic fever syndromes, including familial Mediterranean fever, hyperimmunoglobulin D and periodic fever syndrome and TNF-receptor associated periodic syndromes (TRAPS), and Adult-onset Still's disease, Schnitzler's syndrome, and fibrosing alveolitis.

In some embodiments, a receptor binding agent is administered to a subject to reduce activity or expression of IL-6 in the subject. For example, the subject can have a disorder that is associated or mediated at least in part by IL-6.

Ocular Disorders and Ocular Delivery

The receptor binding agents described herein can be used to treat ocular disorders, including ocular disorders affecting the surface of the eye, inflammatory ocular disorders, and ocular disorders mediated at least in part by an autoimmune reaction.

In some embodiments, the ocular disorder is a dry eye disorder that affects the surface of the eye. The disorder includes conditions also referred to keratoconjunctivitis sicca, keratitis sicca, sicca syndrome, xerophthalmia, tear film disorder, decreased tear production, aqueous tear deficiency, and Meibomian gland dysfunction. Dry eye can include forms that are associated with Sjögren's syndrome (SS), e.g., Sjögren's syndrome associated keratoconjunctivitis sicca, but also forms that are not so associated, e.g., non-Sjögren's syndrome associated keratoconjunctivitis sicca. The patient may or may not have other manifestations of a systemic autoimmune disorder. IL-1 has been implicated in the pathogenesis of dry eye disorders. See, e.g., Enriquez de Salamanca et al. (2010), Mol. Vis. 16:862-873.

Subjects having a dry eye syndrome can exhibit inflammation of the eye dry, and can experience scratchy, stingy, itchy, burning or pressured sensations, irritation, pain, and redness. Dry eye can be associated with both excessive eye watering and conversely insufficient tear production. A receptor binding agent can be administered to such subjects to ameliorate or prevent the onset or worsening of one or more such symptoms. A receptor binding agent can also be used to mitigate pain, e.g., ocular pain, such as due to neuroinflammation, in a subject who is experiencing such pain.

In some embodiments, the ocular disorder is an ocular disorder associated with a systemic autoimmune disorder (such as Sjögren's syndrome and rheumatoid arthritis) or with a disorder associated with IL-1 or another IL-1 cytokine family member. The patient may or may not have a systemic autoimmune disorder or other manifestations of a systemic autoimmune disorder.

A receptor binding agent can also be used to treat other disorders affecting the surface of the eye, such as the cornea. Such disorders include corneal ocular surface inflammatory conditions, corneal neovascularization, keratitis, including peripheral ulcerative keratitis and microbial keratitis. The receptor binding agent can be used to treat a subject undergoing corneal wound healing (e.g., a subject having a corneal wound). A receptor binding agent can be administered to a subject who is about to receive, undergoing, or recovering from a procedure involving the eye, e.g., corneal transplantation/keratoplasty, keratoprosthesis surgery, lamellar transplantation, selective endothelial transplantation. See, e.g., Dana (2007) Trans Am Ophthalmol Soc 105: 330-43; Dekaris et al. (1999) Curr Eye Res 19(5): 456-9; and Dana et al. (1997) Transplantation 63:1501-7. A receptor binding agent can be used to treat disorders affecting the conjunctiva, including conjunctival scarring disorders and conjunctivitis. The receptor binding agent can be used to treat still other disorders such as pemphigoid syndrome and Stevens-Johnson syndrome. A receptor binding agent described herein can be administered to a subject to modulate neovascularization in or around the eye. See, e.g., Dana (2007) Trans Am Ophthalmol Soc 105: 330-43.

A receptor binding agent can be administered to a subject having an allergic reaction affecting the eye, e.g., a subject experiencing severe allergic (atopic) eye disease such as allergic conjunctivitis. For example, the receptor binding agent can be administered topically. See also, e.g., Keane-Myers A M et al. (1999) Invest Ophthalmol Vis Sci, 40(12): 3041-6.

A receptor binding agent can be administered to a subject having an autoimmune disorder affecting the eye. Exemplary autoimmune ocular disorders include sympathetic ophthalmia, Vogt-Koyanagi Harada (VKH) syndrome, birdshot retinochoriodopathy, ocular cicatricial pemphigoid, Fuchs' heterochronic iridocyclitis, and various forms of uveitis. A receptor binding agent can be administered to a subject to treat any of the foregoing disorders.

A receptor binding agent can be administered to a subject who has or is at risk for diabetic retinopathy. See, e.g., Demircan et al. (2006) Eye 20:1366-1369 and Doganay et al. (2006) Eye, 16:163-170

Uveitis includes acute and chronic forms and includes inflammation of one or more of the iris, the ciliary body, and the choroid. Chronic forms may be associated with systemic autoimmune disease, e.g., Behcet's syndrome, ankylosing spondylitis, juvenile rheumatoid arthritis, Reiter's syndrome, and inflammatory bowel disease. In anterior uveitis, inflammation is primarily in the iris (also iritis). Anterior uveitis can affect subjects who have systemic autoimmune disease, but also subjects who do not have systemic autoimmune disease. Intermediate uveitis involves inflammation of the anterior vitreous, peripheral retina, and ciliary body, often with little anterior or chorioretinal inflammation. Pan planitis results from inflammation of the pars plana between the iris and the choroid. Posterior uveitis involves the uveal tract and primarily the choroid, and is also referred to as choroiditis. Posterior uveitis can be associated with a systemic infection or an autoimmune disease. It can persist for months and even years. A receptor binding agent can be administered to a subject to treat any of the foregoing forms of uveitis. See also e.g., Tsai et al. (2009) Mol Vis 15:1542-1552 and Trittibach P et al. (2008) Gene Ther. 15(22): 1478-88.

In some embodiments, a receptor binding agent is used to treat a subject having or at risk for age-related macular degeneration (AMD). The receptor binding agent can be applied topically to the eye, injected (e.g., intravitreally) or provided systemically. See, e.g., Olson et al. (2009) Ocul Immunol Inflamm 17(3):195-200.

A receptor binding agent described herein can be administered by any mode to treat an ocular disease. The agent can be delivered by a parenteral mode. Alternatively or in addition, the agent can be delivered directly to the eye or in the vicinity of the eye. For example, the protein can be administered topically or intraocularly, e.g., as described below.

Formulations and Methods for Ocular Delivery

Ophthalmic formulations containing a receptor binding agent can be delivered for topical administration, e.g., for administration as a liquid drop or an ointment, or for implantation, e.g., into an anterior chamber of the eye or the conjunctival sac. Liquid drops can be delivered using an eye dropper. When formulated for ocular delivery, the receptor binding agent can be present at 0.0001-0.1%, 0.001-5%, e.g., 0.005-0.5%, 0.05-0.5%, 0.01-5%, 0.1-2% or 1%-5% concentration. Frequently the ophthalmic formulation is applied directly to the eye including topical application to the eyelids or instillation into the space (cul-de-sac) between the eyeball and the eyelids. The ophthalmic formulation can be designed to mix readily with the lacrimal fluids and spread over the surfaces of the cornea and conjunctiva. With the usual technique of administration, the major portion of the drug is deposited in the lower fornix. Capillarity, diffusional forces, and the blinking reflex drive incorporation of the drug in the precorneal film from which it penetrates into and through the cornea.

Ophthalmic formulations can also include one or more other agents, e.g., an anti-inflammatory steroid such as rimexolone, loteprednol, medrysone and hydrocortisone, or a non-steroidal anti-inflammatory. For example, the steroid can be present at a concentration of 0.001 to 1%. In some embodiments, no steroid is present. For example, the receptor binding agent is the only active agent in the formulation.

The formulation can also include one or more of the following components: surfactants, tonicity agents, buffers, preservatives, co-solvents and viscosity building agents. Tonicity agents can be used to adjust the tonicity of the composition, e.g., to that of natural tears. For example, potassium chloride, sodium chloride, magnesium chloride, calcium chloride, dextrose and/or mannitol may be added to achieve an appropriate tonicity, e.g., physiological tonicity. Tonicity agents can be added in an amount sufficient to provide an osmolality of about 150-450 mOsm or 250-350 mOsm.

The formulation can also include buffering suitable for ophthalmic delivery. The buffer can include one or more buffering components (e.g., sodium phosphate, sodium acetate, sodium citrate, sodium borate or boric acid) to changes in pH especially under storage conditions. For example, the buffer can be selected to provide a target pH within the range of pH 6.0-7.5, e.g., 6.5-7.5.

The formulation can include an aqueous or phospholipid carrier. Particularly for treating dry eye disorders, the formulation can include agents to provide short-term relief, e.g., compounds which lubricate the eye and assist in tear formation. For example, phospholipid carriers (which include one or more phospholipids) can be used to provide short-term relief. Examples or artificial tears compositions useful as artificial tears carriers include commercial products such as Tears Naturale™ (Alcon Labs, Inc., TX USA). For example, per ml, the formulation can include: 1 mg dextran, 70 and 3 mg hydroxypropyl methylcellulose, and optionally a preservative such POLYQUAD® (polyquaternium-1) 0.001% (m/v). Examples of phospholipid carrier formulations include those disclosed in U.S. Pat. No. 4,804,539, U.S. Pat. No. 4,883,658, U.S. Pat. No. 5,075,104, U.S. Pat. No. 5,278,151, and U.S. Pat. No. 5,578,586.

The formulation can also include other compounds that act as a lubricant or wetting agent. These include viscosity agents such as: monomeric polyols, such as, glycerol, propylene glycol, ethylene glycol; polymeric polyols, such as polyethylene glycol, various polymers of the cellulose family: hydroxypropylmethyl cellulose ("HPMC"), carboxy methylcellulose sodium, hydroxy propylcellulose ("HPC"), dextrans, such as dextran 70; water soluble proteins, such as gelatin; and vinyl polymers, such as polyvinyl alcohol, polyvinylpyrrolidone, povidone and carbomers, such as carbomer 934P, carbomer 941; carbomer 940, carbomer 974P. Still additional examples include polysaccharides, such as hyaluronic acid and its salts and chondroitin sulfate and its salts, and acrylic acid polymers. In certain embodiments, the formulation has a viscosity between 1 to 400 cP.

The formulation can be packaged for single or multi-dose use, e.g., in a bottle with an associated dropper or as a set of single-use droppers. The formulation can include one or more preservatives, e.g., to prevent microbial and fungal contamination during use. Exemplary preservatives include: benzalkonium chloride, chlorobutanol, benzododecinium bromide, methyl paraben, propyl paraben, phenylethyl alcohol, edetate disodium, sorbic acid, and polyquaternium-1, and can be included at a concentration of from 0.001 to 1.0% w/v. It is also possible to provide a formulation containing a receptor binding agent that is sterile yet free of preservatives. The formulation can be prepared for single use application.

Ophthalmic packs may be used to give prolonged contact of an ophthalmic formulation with the eye. A cotton pledget is saturated with the formulation and then inserted into the superior or inferior fornix. A receptor binding agent may also be administered by the way of iontophoresis. This procedure keeps the solution in contact with the cornea in an eyecup bearing an electrode. Diffusion of the drug is effected by difference of electrical potential.

A receptor binding agent may also be delivered by injection, e.g., subconjunctival injection. The formulation can be injected underneath the conjunctiva facilitating passage through the sclera and into the eye by simple diffusion. The formulation can also be injected underneath the conjunctiva and the underlying Tenon's capsule in the more posterior portion of the eye to deliver the agent to the ciliary body, choroid, and retina. The formulation may also be administered by retrobulbar injection.

With respect to dry eye and other surface disorders, subjects can be evaluated using one or more of the following approaches: the Ocular Surface Disease Index (OSDI), corneal and conjunctival staining, and the Schirmer test.

The Ocular Surface Disease Index (OSDI) is a 12-item questionnaire that provides a rapid assessment of the symptoms of ocular irritation consistent with ocular surface inflammatory disorders, including DES, and their impact on vision-related functioning. See e.g. Ocul Immunol Inflamm. September-October 2007; 15(5):389-93. The 12 items of the OSDI questionnaire are graded on a scale of 0 to 4. Scores are derived based on responses to provide an OSDI score on a scale of 0 to 100, with higher scores representing greater disability. A negative change from baseline indicates an improvement in vision-related function and the ocular inflammatory disorders.

Corneal and Conjunctival Staining: Corneal staining is a measure of epithelial disease, or break in the epithelial barrier of the ocular surface, typically seen with ocular surface inflammatory disorders such as dry eye. Corneal staining can exist even without clinically evident dry eye, if there is significant lid disease, such as posterior blepharitis. Corneal staining is highly correlated with ocular discomfort in many, though not all patients; in general corneal staining is associated with high scores in the OSDI, as described above. For corneal fluorescein staining, saline-moistened fluorescein strips or 1% sodium fluorescein solution are used to stain the tear film. The entire cornea is then examined using slit-lamp evaluation with a yellow barrier filter (#12 Wratten) and cobalt blue illumination. Staining is graded according to the Oxford Schema. Conjunctival staining is likewise a measure of epithelial disease or break in the epithelial barrier of the ocular surface. Conjunctival staining is performed under the slit-lamp using lissamine green. Saline-moistened strip or 1% lissamine green solution is used to stain the tear film, and interpalpebral conjunctival staining is evaluated more than 30 seconds but less than 2 minutes later. Using white light of moderate intensity, only the interpalpebral region of the nasal and temporal conjunctival staining is graded using the Oxford Schema.

Schirmer Test: The Schirmer test is performed in the presence and in the absence of anesthesia by placing a narrow filter-paper strip (5×3 5 mm strip of Whatman #41 filter paper) in the inferior cul-de-sac. This test is conducted in a dimly lit room. The patient gently closes his/her eyes until five minutes have elapsed and the strips are removed. Because the tear front will continue advancing a few millimeters after it has been removed from the eyes, the tear front is marked with a ball-point pen at precisely five minutes. Aqueous tear production is measured by the length in millimeters that the strip wets during 5 minutes. Results of 10 mm or less for the Schirmer test without anesthesia and 5 mm or less for the Schirmer test with anesthesia are considered abnormal. A positive change from baseline indicates improvement of one or more symptoms of an ocular inflammatory disorder described herein.

Formulations and Methods for Pulmonary Delivery

A receptor binding agent can be formulated for inhalatory or other mode of pulmonary delivery, e.g., to administer the agent to a tissue of the respiratory tract, e.g., the upper and lower respiratory tract. The three common systems that can be used to deliver agents locally to the pulmonary air passages include dry powder inhalers (DPIs), metered dose inhalers (MDIs) and nebulizers. MDIs may be used to deliver receptor binding agents in a solubilized form or as a dispersion. Typically MDIs include a freon or other relatively high vapor pressure propellant that forces aerosolized medication into the respiratory tract upon activation of the device. In contrast DPIs generally rely on the inspiratory efforts of the patient to introduce a medicament in a dry powder form to the lungs. Nebulizers form a medicament aerosol to be inhaled by imparting energy to a liquid solution. The agent can be stored in a lyophilized form (e.g., at room temperature) and reconstituted in solution prior to inhalation. Direct pulmonary delivery of drugs during liquid ventilation or pulmonary lavage using a fluorochemical medium are also possible delivery modes. These and other methods can be used to deliver receptor binding agent. For example, the agent is delivered in a dosage unit form of at least about 0.02, 0.1, 0.5, 1, 1.5, 2, 5, 10, 20, 40, or 50 mg/puff or more.

The receptor binding agent may be conveniently delivered in the form of an aerosol spray presentation from pressurized packs or a nebulizer, with the use of a suitable propellant, e.g., dichlorodifluoromethane, trichlorofluoromethane, dielilorotetrafluoroctliane, carbon dioxide or other suitable gas. In the case of a pressurized aerosol, the dosage unit may be determined by providing a valve to deliver a metered amount. Capsules and cartridges for use in an inhaler or insufflator may be formulated containing a powder mix of the receptor binding agent and a suitable powder base such as lactose or starch, if the particle is a formulated particle. In addition to the formulated or unformulated receptor binding agent, other materials such as 100% DPPC or other surfactants can be mixed together to promote the delivery and dispersion of the formulated or unformulated receptor binding agent. Particle size can also be varied to control whether deliver is to the lower or upper respiratory tract. For example, particles in the size range of 1-5 microns or 10-50 microns can be used for the lower and upper respiratory tracts respectively.

Delivery enhancers such as surfactants can be used to further enhance pulmonary delivery. A surfactant is generally a compound having a hydrophilic and lipophilic moiety, which promotes absorption of a drug by interacting with an interface between two immiscible phases. Surfactants are useful in the dry particles for several reasons, e.g., reduction of particle agglomeration and reduction of macrophage phagocytosis. Surfactants are well known in the art and include phosphoglycerides, e.g., phosphatidylcholines, L-alpha-phosphatidylcholine dipalmitoyl (DPPC) and diphosphatidyl glycerol (DPPG); hexadecanol; fatty acids; polyethylene glycol (PEG); polyoxyethylene-9-; auryl ether; palmitic acid; oleic acid; sorbitan trioleate (Span 85); glycocholate; surfactin; poloxomer; sorbitan fatty acid ester; sorbitan trioleate; tyloxapol; and phospholipids.

Also featured herein are antibodies that specifically recognize a chimeric cytokine domain described herein. For example, such antibodies preferentially bind to a chimeric domain relative to any parental cytokine domain. For example, a specific antibody can bind to an epitope that includes a junction between a segment from a first parental cytokine and a second parental cytokine.

Nucleic Acid Delivery

A receptor-binding agent can be provided to a subject by delivering a nucleic acid that encodes and can express the receptor-binding agent. For example, a nucleic acid sequence encoding the receptor-binding agent can be placed under control of transcription control sequences and positioned in a nucleic acid vector for gene delivery, e.g., a viral vector. Exemplary viral vectors include adenoviral, retroviral, or adeno-associated viral vectors. Vectors can be in the form of a plasmid or linear molecule, e.g., a linear double stranded DNA. The delivered nucleic acid can be designed to be incorporated into the genome of the target cell, e.g., to integrate into the genome of the target cell. Alternatively, the delivered nucleic acid can be designed such that after delivery it exists autonomously in the cell.

Transcriptional control sequences can be engineered to provide transient or constitutive expression. Transient control can include control regulated by an exogenous agent, e.g., by using transcriptional response elements for transcription factors responsive to exogenous agents (e.g., a steroid hormone or FK506) or environmental signals.

Expression of genes provided on the delivered nucleic acid can be evaluated, e.g., by detection of the protein encoded by the gene (e.g., using antibodies) or by detection of the mRNA, e.g., using PCR or Northern hybridization. The delivered nucleic acid is generally engineered so that transcriptional and translational regulatory DNA are appropriately positioned relative to the coding sequence for the receptor-binding agent such that transcription is initiated and that protein is translated from the resulting message. The nucleic acid can include transcriptional and translational regulatory nucleic acid sequences from mammalian cells, particularly humans. Such sequences include, e.g., promoter sequences, ribosomal binding sites, transcriptional start and stop sequences, translational start and stop sequences, and enhancer or activator sequences.

In addition, the expression vector may include additional elements. For example, for integrating expression vectors, the expression vector can contain at least one or two sequences homologous to the host cell genome, e.g., flanking the expression construct. The integrating vector may be directed to a specific locus in the host cell by selecting the appropriate homologous sequence for inclusion in the vector. Constructs for integrating vectors are well known in the art.

Exemplary adenoviral vectors include modified versions of human adenoviruses such as Ad2 or Ad5, in which the genetic elements necessary for the virus to replicate in vivo have been removed. For example, the E1 region can be removed and the genome can be further modified to accept an expression cassette coding for the receptor-binding agent.

Exemplary retroviral vectors include LNL6, LXSN, LNCX, and lentiviral vectors. Particular lentiviral vectors are described by Pawliuk et al. (2001) Science 294:2368 and Imren et al. (2002) PNAS 99:14380 and include limited to, human immunodeficiency virus (e.g., HIV-1, HIV-2), feline immunodeficiency virus (FIV), simian immunodeficiency virus (SIV), bovine immunodeficiency virus (BIV), and equine infectious anemia virus (EIAV). These vectors can be constructed and engineered to be safe, e.g., by separating the essential genes (e.g., gag and pol) onto separate vectors and by rendering retrovirus replication defective. The replication defective retrovirus is then packaged into virions through the use of a helper virus or a packaging cell line, by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. The retroviral vector can include, in addition to sequences for expressing a receptor-binding agent, a left (5') retroviral LTR; a retroviral export element, optionally a reverse response element (RRE); a promoter, and a locus control region (LCR) or other transcriptional insulator sequence and a right (3') retroviral LTR. Retroviral vectors can further contain a central polypurine tract (cPPT) or DNA flap to increase viral titers and transduction efficiency.

The nucleic acid containing a sequence encoding a receptor-binding agent can be delivered to any appropriate target cells, e.g., ex vivo or in vivo. Exemplary target cells include synovial cells, hematopoietic cells, dermal cells, and so forth. The nucleic acid can be delivered to target cells associated with the eye, e.g., corneal epithelial cells. Delivery may include the debridement, or scraping of the corneal epithelium to expose a basal layer of epithelium. The nucleic acid for delivery is then added. In another embodiment, the nucleic acid is delivered to corneal endothelial cells, cells of the trabecular meshwork beneath the periphery of the cornea, cells of the choroid layer of the eye, cells of the retina, sclera or ciliary body, cells of the retinal or ocular vasculature, or cells of the vitreous body or cells of the lens, for example the lens epithelium.

Delivery methods include, e.g., retroviral infection, adenoviral infection, transformation with plasmids, transformation with liposomes containing exogenous nucleic acid, biolistic nucleic acid delivery (e.g., loading the nucleic acid onto gold or other metal particles and shooting or injecting into the cells), adeno-associated virus infection and Epstein-Barr virus infection. Delivery can be into cells or tissue by any method including needle injection, hypospray, electroporation, or a gene gun.

Other methods for gene delivery can be found in, e.g., Kay, M. A. (1997) Chest 111(6 Supp.):138S-142S; Ferry, N. and Heard, J. M. (1998) Hum. Gene Ther. 9:1975-81; Shiratory, Y. et al. (1999) Liver 19:265-74; Oka, K. et al. (2000) Curr. Opin. Lipidol. 11:179-86; Thule, P. M. and Liu, J. M. (2000) Gene Ther. 7:1744-52; Yang, N. S. (1992) Crit. Rev. Biotechnol. 12:335-56; Alt, M. (1995) J. Hepatol. 23:746-58; Brody, S. L. and Crystal, R. G. (1994) Ann. N.Y. Acad. Sci. 716:90-101; Strayer, D. S. (1999) Expert Opin. Investig. Drugs 8:2159-2172; Smith-Arica, J. R. and Bartlett, J. S. (2001) Curr. Cardiol. Rep. 3:43-49; and Lee, H. C. et al. (2000) Nature 408:483-8.

Exemplary Second Agents

A receptor binding agent described herein can be administered with a second agent. The two agents can be co-administered, or administered separately, e.g., using different regimes. Exemplary second agents include an anti-inflammatory agent. In one embodiment, the second agent is an IL-17 antagonist (encompassing antagonists of all IL-17 family members, e.g., antagonists of IL-17A, IL-17F, IL-17B, IL-17C, IL-17D, and IL-17E). Exemplary IL-17 antagonists include: agents (such as antibodies and other binding proteins) that bind to IL-17 (including IL-17A, IL-17F, IL-17B, IL-17C, IL-17D, and IL-17E) and which antagonize IL-17 mediated signaling; agents (such as antibodies and other binding proteins) that bind to one or more receptors for IL-17, such as IL-17RA and IL-17RC and which antagonize IL-17 mediated signaling; agents (such as antibodies and other binding proteins) that bind to a complex containing IL-17 and at least one receptor subunit, e.g., IL-17 and Il-17RA, or IL-17, IL-17RA, and IL-17RC and which antagonize IL-17 mediated signaling; and agents such as soluble receptors that include one or more of soluble extracellular domains of IL-17RA and IL-17RC and which antagonize IL-17 mediated signaling.

In another embodiment, the second agent is an IL-12 antagonist. Exemplary IL-12 antagonists include: agents (such as antibodies and other binding proteins) that bind to IL-12 (including p35 and p40) and which antagonize IL-12 mediated signaling; agents (such as antibodies and other binding proteins) that bind to one or more receptors for IL-12, such as IL-12Rβ1 or IL-12Rβ2 and which antagonize IL-12 mediated signaling; agents (such as antibodies and other binding proteins) that bind to a complex containing p35, p40 and at least one receptor subunit, e.g., IL-12Rβ1 or IL-12Rβ2 and which antagonize IL-12 mediated signaling; and agents such as soluble receptors that include one or more of soluble extracellular domains of IL-12Rβ1 or IL-12Rβ2 and which antagonize IL-12 mediated signaling.

In another embodiment, the second agent is an IL-23 antagonist. Exemplary IL-23 antagonists include: agents (such as antibodies and other binding proteins) that bind to IL-23 (including p19 and p40) and which antagonize IL-23 mediated signaling; agents (such as antibodies and other binding proteins) that bind to one or more receptors for IL-23, such as IL-12Rβ1 or IL-23R and which antagonize IL-23 mediated signaling; agents (such as antibodies and other binding proteins) that bind to a complex containing p19, p40 and at least one receptor subunit, e.g., IL-12Rβ1 or IL-23R and which antagonize IL-23 mediated signaling; and agents such as soluble receptors that include one or more of soluble extracellular domains of IL-12Rβ1 or IL-23R and which antagonize IL-23 mediated signaling.

Exemplary antibodies to IL-23 have been described. See e.g., Beyer et al., J. Mol. Biol. (2008), doi:10.1016/j.jmb.2008.08.001.

Animal Models

A receptor binding agent can be evaluated in an animal model for human disease, e.g., a human autoimmune and/or human inflammatory disease. The agent can have specificity for the corresponding target protein in the animal.

Rheumatoid Arthritis Models.

A receptor binding agent can be evaluated in an animal model of rheumatoid arthritis, e.g., the collagen-induced arthritis (CIA) model. See, for example, McIndoe et al., 1999, Proc. Natl. Acad. Sci. USA, 96:2210-2214; Issekutz, A. C. et al., Immunology (1996) 88:569; and Current Protocols in Immunology, Unit 15.5, Coligan et al. (eds.), John Wiley & Sons, Inc. The model is produced by the immunization of susceptible strains of rat/mice with native type II collagen. Collagen is emulsified in Complete Freund's Adjuvant (CFA) and injected intradermally (100 μg collagen:100 μg CFA/mouse) at the base of the tail. Control mice are injected intradermally with 0.05 ml of distilled water/CFA emulsion. A booster injection of collagen in incomplete adjuvant is given 21 days after the initial immunization. Disease is due to an autoimmune response induced upon immunization with collagen.

The joints can be scored for arthritis, inflammation, pannus, cartilage damage and bone resorption using a defined scale. For example the severity of arthritis can be scored as follows: 0=no visible effects of arthritis; 1=edema and erythema of one digit or joint; 2=edema and erythema of two joints; 3=edema and erythema of more than two joint; 4=severe arthritis of the entire paw and digits, accompanied by ankylosis of the ankle and deformity of the limb. The score for each limb is summed and recorded as the arthritic index (AI) for each individual animal. Other scoring schemes can also be used for these and other criteria.

Multiple Sclerosis.

Experimental allergic encephalomyelitis (EAE) is a useful murine model for multiple sclerosis. A receptor binding agent can be evaluated in the EAE model. EAE is a T cell mediated autoimmune disorder characterized by T cell and mononuclear cell inflammation and subsequent demyelination of axons in the central nervous system. (See, for example, Bolton, C., 1995, Multiple Sclerosis, 143.) Exemplary protocols can be found in Current Protocols in Immunology, Unit 15.1 and 15.2; Coligan et al. (eds.), John Wiley & Sons, Inc. Models are also available for myelin disease in which oligodendrocytes or Schwann cells are grafted into the central nervous system, for example, as described in Duncan et al., 1997, Molec. Med. Today, 554-561.

Allograft.

A receptor binding agent can be evaluated in an animal model for skin allograft rejection, e.g., using murine tail-skin grafts. Skin allograft rejection is mediated by T cells, helper T cells and killer-effector T cells. See, for example, Current Protocols in Immunology, Unit 4.4; Coligan et al. (eds.), 1995, John Wiley & Sons, Inc. Other transplant rejection models can also be used. See, e.g., Tinubu et al., 1994, J. Immunol., 4330-4338.

IBD and Colitis Models.

An exemplary model for inflammatory bowel disease is the use of CD4+ CD45Rb-high cells transferred to SCID mice. See e.g., Hirano et al., J Pharmacol Sci. June 2009; 110(2):169-81 and the use of transgenic IL-10 deficient mice. See e.g., Inaba et al., Inflamm Bowel Dis., DOI: 10.1002/ibd.21253 (2010). Yet another exemplary colitis model employs dextran sulfate sodium (DSS) to induce acute colitis. For example, colitis can be induced in mice by administration of 5% (wt/vol) DSS (molecular mass 30-40 kDa; ICN Biomedicals, Aurora, Ohio) in drinking water ad libitum. Symptoms resulting from this treatment bloody diarrhea, weight loss, colon shortening and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. See, e.g., Hassan et al. PLoS One. Jan. 25, 2010; 5(1):e8868.

Dry Eye Disease Models.

A receptor binding agent can be evaluated in a mouse model for dry eye disease. Dry eye can be induced in mice by subcutaneous injection of scopolamine and then placement of the mice in controlled-environment chambers. By way of a specific example, normal healthy 6 to 10 weeks old female C57BL/6 mice can be induced to have dry eye by continuous exposure to dry environment in a controlled environmental chamber. The chamber has low relative humidity of less than 30% (generally about 19%), high airflow (15 liters/minute) and constant temperature (about 22° C.). The mice placed in the chamber are also treated with scopolamine to inhibit tear secretion. Sustained-release transdermal scopolamine patches can be obtained from Novartis (Summit, N.J.). One-fourth of a patch is applied to the depilated mid-tail of mice every 48 hours. The combination of the controlled environmental chamber and scopolamine produces severe dry eye in a relative short period of time (about 2-4 days). The controlled environmental chamber can be prepared as described in Barbino et al., Invest. Ophthal. Vis. Sci., 46: 2766-2711 (2005), and enables control of air flow, humidity, and temperature.

Mice can be monitored for signs of dry eye, e.g., by performing: a) cotton thread test to measure aqueous tear production, which is generally decreased in patients with dry eye; b) corneal fluorescein staining which is a marker of corneal surface damage; and general ophthalmic examination.

Cotton Thread Test: Tear production can be measured with cotton thread test, impregnated with phenol red (Zone-Quick, Lacrimedics, Eastsound, Wash.). Under a magnifying fluorescent lamp, the thread is held with jeweler forceps and placed in the lateral cantus of the conjunctival fornix of the right eye for 30 or 60 seconds. The tear distance in mm is read under a microscope using the scale of a hemacytometer.

Corneal Fluorescein Staining: Corneal fluorescein staining can be evaluated by applying 1.0 μl of 5% fluorescein by a micropipette into the inferior conjunctival sac of the eye. The cornea is examined with a slit lamp biomicroscope using cobalt blue light 3 minutes after the fluorescein instillation. Punctuate staining is recorded in a masked fashion using a standardized National Eye Institute (NEI)

grading system of 0-3 for each of the five areas in which the corneal surface has been divided.

Diagnostic and Other Uses

A receptor binding agent described herein can be used to detect IL-1R1 in a sample, or cells expressing such a receptor. For example, the agent can be labeled directly or indirectly with a moiety that is a label or produces a signal, e.g., an enzyme, a radiolabel, an epitope, or a fluorescent protein (such as green fluorescent protein). The agent can be contacted to a sample or to cells to determine if the receptor is present in the sample or on the cells, e.g., using standard immunoblotting, immunofluorescence, enzyme immunoassay (EIA), radioimmunoassay (RIA), fluorescence energy transfer, Western blot, and other diagnostic and detection techniques.

The receptor binding agent can also be labeled for in vivo detection and administered to a subject. The subject can be imaged, e.g., by NMR or other tomographic means. For example, the binding agent can be labeled with a radiolabel such as $^{131}$I, $^{111}$In, $^{123}$I, $^{99m}$Tc, $^{32}$P, $^{125}$I, $^{3}$H, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. The agent can be labeled with a contrast agent such as paramagnetic agents and ferromagnetic or superparamagnetic (which primarily alter T2 response)

A receptor binding agent can also be used to purify cells which express the receptor to which it binds. For example, the receptor binding agent can be coupled to an immobilized support (e.g., magnetic beads or a column matrix) and contacted to cells which may express the receptor. The support can be washed, e.g., with a physiological buffer, and the cells can be recovered from the support.

A receptor binding agent can also be used to purify soluble forms of the receptor to which it binds. For example, samples containing the soluble receptor can be contacted to immobilized receptor binding agent and then, e.g., after washing, can be recovered from the immobilized agent.

The following non-limiting examples further illustrate embodiments of the inventions described herein.

EXAMPLES

Example 1

Nucleic acids encoding the proteins with the amino acid sequences listed in Table 4 (below) were constructed in a pET vector containing a T7 promoter and ampicillin (pET31 series) or kanamycin resistance genes (pET28 series) (EMD Chemicals, Gibbstown N.J., USA), and expressed. Examples of coding sequences that can be used for expression are provided in Table 5.

TABLE 4

| Exemplary chimeric proteins | SEQ ID NO: |
|---|---|
| P01 APVRSLAFRIWDVNQKTFYLRNNQLVAGYLQGPNVNLEEKIDVS FVQGEESNDKIPVALGIHGGKMCLSCVKSGDETRLQLEAVDPKN YPKKKMDKRFAFIRSDSGPTTSFESAACPGWFLCTAMEADQPVS LTNMPDEGVMVTKFYMQFVSS | 17 |
| P02 APVRSLAFRIWDVNQKTFYLRNNQLVAGYLQGPNVNLEEKIDVS FVQGEESNDKIPVALGIHGGKMCLSCVKSGDETRLQLEAVDPKN | 18 |

TABLE 4-continued

| Exemplary chimeric proteins | SEQ ID NO: |
|---|---|
| YPKKKMEKRFVFNKIEINNKLSFESAACPGWFLCTAMEADQPVS LTNMPDEGVMVTKFYMQFVSS | |
| P03 APVRSLAFRIWDVNQKTFYLRNNQLVAGYLQGPNVNLEEKFSMS FVQGEESNDKIPVALGLKEKNLYLSCVLKDDKPTLQLESVDPKN YPKKKMEKRFVFIRSDSGPTTSFESAACPGWFLCTAMEADQPVS LTNMPDEGVMVTKFTMQFVSS | 19 |
| P04 APVRSLAFRIWDVNQKTFYLRNNQLVAGYLQGPNVNLEEKFSMS FVQGEESNDKIPVALGLKEKNLYLSCVLKDDKPTLQLESVDPKN YPKKKMEKRFVFNKIEINNKLEFESAACPGWFLCTAMEADQPVS LTNMPDEGVMVTKFTMQFVSS | 20 |
| P05 APVRSLNCRIWDVNQKTFYLRNNQLVAGYLQGPNVNLEEKFSMS FVQGEESNDKIPVALGLKEKNLYLSCVLKDDKPTLQLESVDPKN YPKKKMEKRFVFNKIEINNKLEFESAQFPNWFLCTAMEADQPVS LTNMPDEGVMVTKFYMQFVSS | 21 |
| P06 APVRSLNCTLWDVNQKTFYLRNNQLVAGYLQGPNVEQQVVFSMS FVQGEESNDKIPVALGLKEKNLYLSCVLKDDKPTLQLESVDPKN YPKKKMEKRFVFNKIEINNKLEFESAQFPNWYISTSMEADQPVF LGGTKGGQDITDFTMQFVSS | 23 |
| P07 APVRSLNCRIWDVNQKTFYLRNNQLVAGYLQGPNVNLEEKFSMS FVQGEESNDKIPVALGLKEKNLYLSCVLKDDKPTLQLESVDPKN YPKKKMEKRFVFNKIEINNKLEFESAQFPNWFLCTAMEADQPVS LTNMPDEGQDITDFTMQFVSS | 24 |

Exemplary nucleic acid sequences encoding the above proteins are listed in Table 5. In some embodiments, the nucleic acid sequence further includes an ATG prior to the first nucleotide listed below. In some embodiments, the nucleic acid sequence further includes a stop codon (such as TAA, TAG, or TGA) after the last nucleotide listed below.

TABLE 5

| Nucleic acids encoding exemplary chimeric proteins | SEQ ID NO: |
|---|---|
| P01 GCACCTGTACGATCACTGGCCTTCAGAATCTGGGATGTTAACCA GAAGACCTTCTATCTGAGGAACAACCAACTAGTTGCTGGATACT TGCAAGGACCAAATGTCAATTTAGAAGAAAAGATAGATGTGTCC TTTGTACAAGGAGAAGAAAGTAATGACAAAATACCTGTGGCCTT GGGCATCCATGGAGGGAAGATGTGCCTGTCCTGTGTCAAGTCTG GTGATGAGACCAGACTCCAGCTGGAGGCAGTTGATCCCAAAAAT TACCCAAAGAAGAAGATGGACAAGCGCTTCGCCTTCATCCGCTC AGACAGCGGCCCCACCACCAGTTTTGAGTCTGCCGCCTGCCCCG GTTGGTTCCTCTGCACAGCGATGGAAGCTGACCAGCCCGTCAGC CTCACCAATATGCCTGACGAAGGCGTCATGGTCACCAAATTCTA CATGCAATTTGTGTCTTCC | 25 |
| P02 GCACCTGTACGATCACTGGCCTTCAGAATCTGGGATGTTAACCA GAAGACCTTCTATCTGAGGAACAACCAACTAGTTGCTGGATACT TGCAAGGACCAAATGTCAATTTAGAAGAAAAGATAGATGTGTCC TTTGTACAAGGAGAAGAAAGTAATGACAAAATACCTGTGGCCTT GGGCATCCATGGAGGGAAGATGTGCCTGTCCTGTGTCAAGTCTG GTGATGAGACCAGACTCCAGCTGGAGGCAGTTGATCCCAAAAAT TACCCAAAGAAGAAGATGGAAAAGCGATTTGTCTTCAACAAGAT AGAAATCAATAACAAGCTGAGTTTTGAGTCTGCCGCCTGCCCCG GTTGGTTCCTCTGCACAGCGATGGAAGCTGACCAGCCCGTCAGC CTCACCAATATGCCTGACGAAGGCGTCATGGTCACCAAATTCTA CATGCAATTTGTGTCTTCC | 26 |
| P03 GCACCTGTACGATCACTGGCCTTCAGAATCTGGGATGTTAACCA GAAGACCTTCTATCTGAGGAACAACCAACTAGTTGCTGGATACT TGCAAGGACCAAATGTCAATTTAGAAGAAAAGTTCTCCATGTCC TTTGTACAAGGAGAAGAAAGTAATGACAAAATACCTGTGGCCTT GGGCCTCAAGGAAAAGAATCTGTACCTGTCCTGCGTGTTGAAAG ATGATAAGCCCACTCTACAGCTGGAGAGTGTAGATCCCAAAAAT TACCCAAAGAAGAAGATGGAAAAGCGATTTGTCTTCATCCGCTC AGACAGCGGCCCCACCACCAGTTTTGAGTCTGCCGCCTGCCCCG | 27 |

TABLE 5-continued

| Nucleic acids encoding exemplary chimeric proteins | | SEQ ID NO: |
|---|---|---|
| | GTTGGTTCCTCTGCACAGCGATGGAAGCTGACCAGCCCGTCAGC CTCACCAATATGCCTGACGAAGGCGTCATGGTCACCAAATTCAC CATGCAATTTGTGTCTTCC | |
| P04 | GCACCTGTACGATCACTGGCCTTCAGAATCTGGGATGTTAACCA GAAGACCTTCTATCTGAGGAACAACCAACTAGTTGCTGGATACT TGCAAGGACCAAATGTCAATTTAGAAGAAAAGTTCTCCATGTCC TTTGTACAAGGAGAAGAAAGTAATGACAAAATACCTGTGGCCTT GGGCCTCAAGGAAAAGAATCTGTACCTGTCCTGCGTGTTGAAAG ATGATAAGCCCACTCTACAGCTGGAGAGTGTAGATCCCAAAAAT TACCCAAAGAAGAAGATGGAAAAGCGATTTGTCTTCAACAAGAT AGAAATCAATAACAAGCTGGAATTTGAGTCTGCCGCCTGCCCCG GTTGGTTCCTCTGCACAGCGATGGAAGCTGACCAGCCCGTCAGC CTCACCAATATGCCTGACGAAGGCGTCATGGTCACCAAATTCAC CATGCAATTTGTGTCTTCC | 28 |
| P05 | GCACCTGTACGATCACTGAACTGCAGAATCTGGGATGTTAACCA GAAGACCTTCTATCTGAGGAACAACCAACTAGTTGCTGGATACT TGCAAGGACCAAATGTCAATTTAGAAGAAAAGTTCTCCATGTCC TTTGTACAAGGAGAAGAAAGTAATGACAAAATACCTGTGGCCTT GGGCCTCAAGGAAAAGAATCTGTACCTGTCCTGCGTGTTGAAAG ATGATAAGCCCACTCTACAGCTGGAGAGTGTAGATCCCAAAAAT TACCCAAAGAAGAAGATGGAAAAGCGATTTGTCTTCAACAAGAT AGAAATCAATAACAAGCTGGAATTTGAGTCTGCCCAGTTCCCA ACTGGTTCCTCTGCACAGCGATGGAAGCTGACCAGCCCGTCAGC CTCACCAATATGCCTGACGAAGGCGTCATGGTCACCAAATTCTA CATGCAATTTGTGTCTTCC | 29 |
| P06 | GCACCTGTACGATCACTGAACTGCACGCTCTGGGATGTTAACCA GAAGACCTTCTATCTGAGGAACAACCAACTAGTTGCTGGATACT TGCAAGGACCAAATGTCGAGCAACAAGTGGTGTTCTCCATGTCC TTTGTACAAGGAGAAGAAAGTAATGACAAAATACCTGTGGCCTT GGGCCTCAAGGAAAAGAATCTGTACCTGTCCTGCGTGTTGAAAG ATGATAAGCCCACTCTACAGCTGGAGAGTGTAGATCCCAAAAAT TACCCAAAGAAGAAGATGGAAAAGCGATTTGTCTTCAACAAGAT AGAAATCAATAACAAGCTGGAATTTGAGTCTGCCCAGTTCCCA ACTGGTACATCAGCACCTCTATGGAAGCTGACCAGCCCGTCTTC CTGGGAGGGACCAAAGGCGGCCAGGATATAACTGACTTCACCAT GCAATTTGTGTCTTCC | 30 |
| P07 | GCACCTGTACGATCACTGAACTGCAGAATCTGGGATGTTAACCA GAAGACCTTCTATCTGAGGAACAACCAACTAGTTGCTGGATACT TGCAAGGACCAAATGTCAATTTAGAAGAAAAGTTCTCCATGTCC TTTGTACAAGGAGAAGAAAGTAATGACAAAATACCTGTGGCCTT GGGCCTCAAGGAAAAGAATCTGTACCTGTCCTGCGTGTTGAAAG ATGATAAGCCCACTCTACAGCTGGAGAGTGTAGATCCCAAAAAT TACCCAAAGAAGAAGATGGAAAAGCGATTTGTCTTCAACAAGAT AGAAATCAATAACAAGCTGGAATTTGAGTCTGCCCAGTTCCCA ACTGGTTCCTCTGCACAGCGATGGAAGCTGACCAGCCCGTCAGC CTCACCAATATGCCTGACGAAGGCCAGGATATAACTGACTTCAC CATGCAATTTGTGTCTTCC | 31 |

The proteins can include a range of different residues from IL-1β and IL-1Ra as illustrated below. Among the examples P01, P02, P03, P04, and P05, the cytokine domains can have 48-70% residues from IL-1β and 55-78% residues from IL-1Ra. (Because a number of amino acid residues are conserved between the two proteins, the sum of the percentage identity to IL-1β and to IL-1Ra can be greater than 100%.)

TABLE 6

| | IL-1β residues | IL-1RA residues | Total residues | % IL-1β | % IL-1RA |
|---|---|---|---|---|---|
| P06 | 130 | 62 | 152 | 85.5 | 40.8 |
| P07 | 113 | 80 | 153 | 73.9 | 52.3 |
| P05 | 108 | 85 | 153 | 70.6 | 55.6 |
| P04 | 104 | 89 | 153 | 68.0 | 58.2 |
| P03 | 94 | 99 | 153 | 61.4 | 64.7 |
| P02 | 85 | 108 | 153 | 55.6 | 70.6 |
| P01 | 74 | 119 | 153 | 48.4 | 77.8 |

Example 2

Proteins that contain a hexa-histidine tag (SEQ ID NO:42) were expressed in *E. coli* cells BL21(DES) strain by induction with 1 mM IPTG at 37° C. for 3 hours in LB broth media. The cells were lysed in 20-50 mM Tris, 0.5 M NaCl, 2.5 mM EDTA, 0.1% Triton X-100, pH 8.0. Lysates were subjected to IMAC chromatography using a HiTrap@ prepacked column (GE Healthcare, Piscataway N.J., USA). The protein was loaded in 20 mM sodium phosphate, 0.5 M NaCl 10 mM imidazole, pH 7.4 buffer. It was eluted with 200 mM imidazole, 20 mM sodium phosphate, 0.5 M NaCl pH 7.4 buffer. Eluted protein was dialyzed extensively against PBS, 0.1% Polysorbate 80, pH 7.4, concentrated using an Amicon Ultra@ (10K) filter, and stored at 4° or −80° C.

Figure 6:
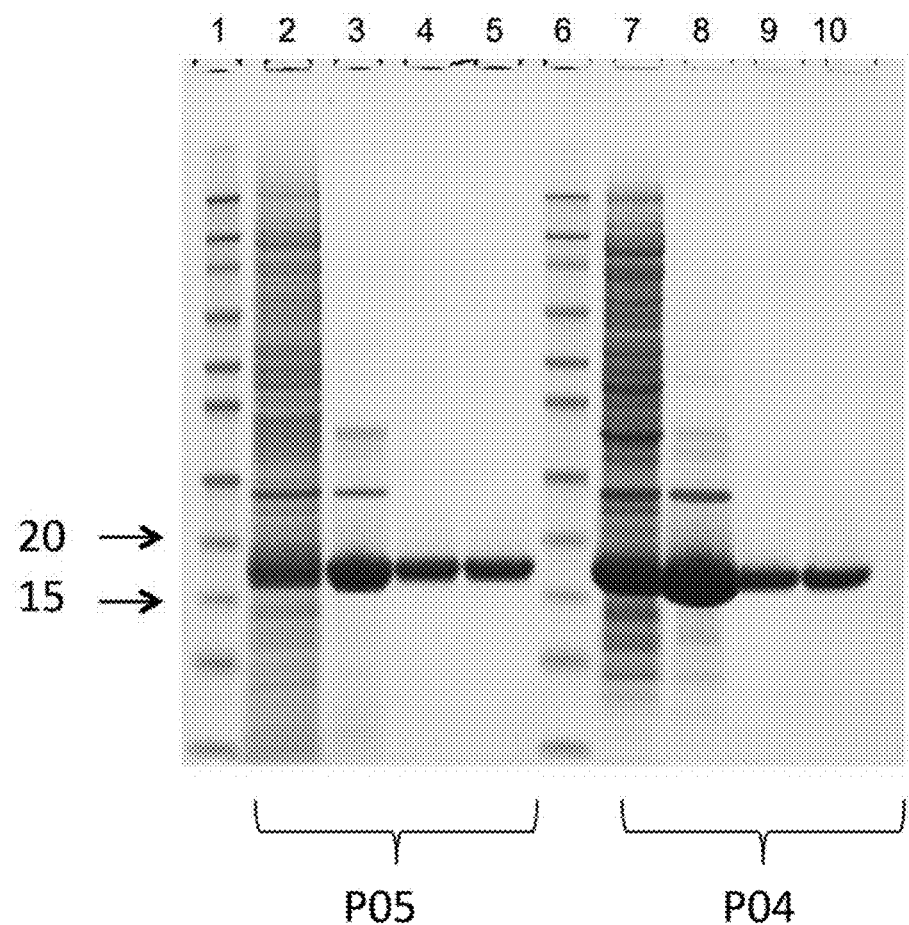
FIG. 6 is an image of an SDS-PAGE gel showing exemplary samples of protein purified from *E. coli* cells expressing receptor binding agents. The 15 and 20 kDa molecular weight markers are indicated at left. Lanes are as follows: molecular weight marker (lane 1 and 6), extract (lanes 2 and 7), material purified by cation exchange chromatography (lanes 3 and 8), material additionally purified by anion exchange chromatography (lanes 4 and 9), and reduced samples of such material (lanes 5 and 10). Lanes 2-5 are of P05 purification, and Lanes 6-10 are of P04 purification. See also Example 2.

Proteins lacking a hexa-histidine tag (SEQ ID NO:42) were purified by ion exchange chromatography. P05 protein was purified by ion exchange chromatography. Lysate from expressing cells was applied to a GigaCapS™ column (Tosoh Bioscience LLC, King of Prussia, Pa., USA) at low pH (approximately pH 5.5) in the absence of salt (conductivity approximately 1 mS/cm). The column was then eluted by a pH gradient (Buffer A=10 mM acetic acid, pH 5.5; Buffer B=20 mM Tris pH 8). A 5 ml fraction containing the eluted protein was then diluted with 5 ml of H$_2$O and 5 ml of 20 mM Tris pH 8) and then applied to CaptoQ™ resin (GE Healthcare, Piscataway N.J., USA) and eluted with a 0 mM to 250 mM NaCl gradient in 20 mM Tris pH 8.0. The eluted protein was dialyzed extensively against 1.25×PBS 0.1% TWEEN® 80 or 1.25×PBS lacking TWEEN® and stored. See FIG. 6. P03 and P04 proteins were purified using similar methods.

Cells expressing P05 were also grown in TEKNOVA™ Terrific Broth with animal free soytone (#T7660) supplemented with 10 g/L glucose, 10 mM MgSO$_4$, trace elements (1 mg/ml TEKNOVA™ 1000× Trace Elements, #T1001), and antibiotic in a Sartorius 2L BIOSTAT™ A+ and were induced at OD 35-40 with 1 mM IPTG for about 6 hours. Cells are grown at 37° C. with 30% dissolved oxygen at pH 7.0, and agitation at 200-800 rpm with oxygen sparge at 2 L/min. Cells are fed 9 g glucose/L/hr when glucose is depleted as detected by a pH increase. Feed is reduced to 6 g glucose/L/hr when the pH decreases (about 2.5 hrs after induction).

Cells were collected and lysed in lysis buffer (20 mM Tris, 10 mM EDTA, 0.1% Triton, pH 8.0; 20 mM Tris, 10 mM EDTA, 0.1% Triton, pH 7.0; 50 mM MOPS, 10 mM EDTA, 0.1% Triton, pH 6.5; or 50 mM MOPS, 10 mM EDTA, 0.1% Triton, pH 6.0). Lysate is loaded onto Poros XS® cation ion exchange media (Life Technologies Corp., Carlsbad Calif. USA) at pH 5.3 and 3 mS/cm (35 mg product per ml column resin).

In an exemplary procedure, P05 protein is eluted by a step to pH 7.0 using buffer containing 100 mM MOPS 25 mM NaCl pH 7.0. The first eluting peak was discarded, and the second eluting peak was collected in pools and contained P05 protein. Early pools are enriched for intact P05 protein relative to a des-Ala species. This eluted material is then flowed over CaptoQ™ anion exchange resin. The flow through, which contains intact P05 protein, is collected.

In another exemplary procedure, the media is washed with 100 mM MOPS 20 mM NaCl pH 6.0. P05 protein is eluted by a step to pH 6.0 using buffer containing 100 mM MOPS 50-58 mM NaCl pH 6.0. The first eluting peak was separated from subsequent peaks and contained intact P05 protein. This eluted material is then flowed over CaptoQ™ anion exchange resin. The flow through, which contains intact P05 protein, is collected.

Example 3

The proteins or supernatants containing the proteins were evaluated in a cell-based assay for IL-1 activity. HEK-Blue™ IL-1β responsive cells were used to monitor IL-1β activity (available from InvivoGen Inc., San Diego Calif., USA). These cells include a SEAP reporter gene under the control of the IFN-β minimal promoter fused to five NF-κB and five AP-1 binding sites. IL-1β engagement of IL-1 receptors on the cell surface lead to NF-κB activation and SEAP production. The SEAP report can be detected, e.g., using QUANTI-Blue™ (InvivoGen Inc., San Diego Calif., USA) and spectrophotometric analysis. A HEK-Blue IL-1β cell suspension was prepared from cells cultured to 70-80% confluence. The resuspended cells were adjusted to ~330,000 cells/ml in fresh growth medium (DMEM, 4.5 g/l glucose, 2 mM L-Glutamine, 10% (v/v) heat-inactivated fetal bovine serum (30 min at 56° C.), 50 U/ml penicillin, 50 μg/ml streptomycin, 100 μg/ml NormocinT).

Reagents were added to wells of a flat-bottom 96-well cell culture plate: 10 μl of IL-1β at 20 ng/ml, 1 μl of the agent of interest and 30 μl of cell culture medium to a final volume of 50 μl. Positive and negative controls samples were prepared in parallel. Then 150 μl of HEK-Blue IL-1β cell suspension (~50,000 cells) was added to each well and the plate was cultured overnight at 37° C. in 5% $CO_2$ tissue culture incubator. Generally the final IL-1β concentration (in the 200 μl final volume) was 0.1 ng/ml. IL-1β activity was evaluated the next day (12-15 hours later). Prior to quantitation, the QUANTI-Blue™ reagent was prepared according to the manufacturer's instructions. A flat bottomed 96-well assay plate was prepared in which 150 μl of QUANTI-Blue™ solution was added to each well. 50 μl of conditioned media from the wells of the 96 well tissue culture plate was added to each well of the assay plate. The plate was incubated at 37° C. for approximately 15-20 minutes. SEAP levels were then measured using a spectrophotometer at 620-655 nm.

Figure 7A:
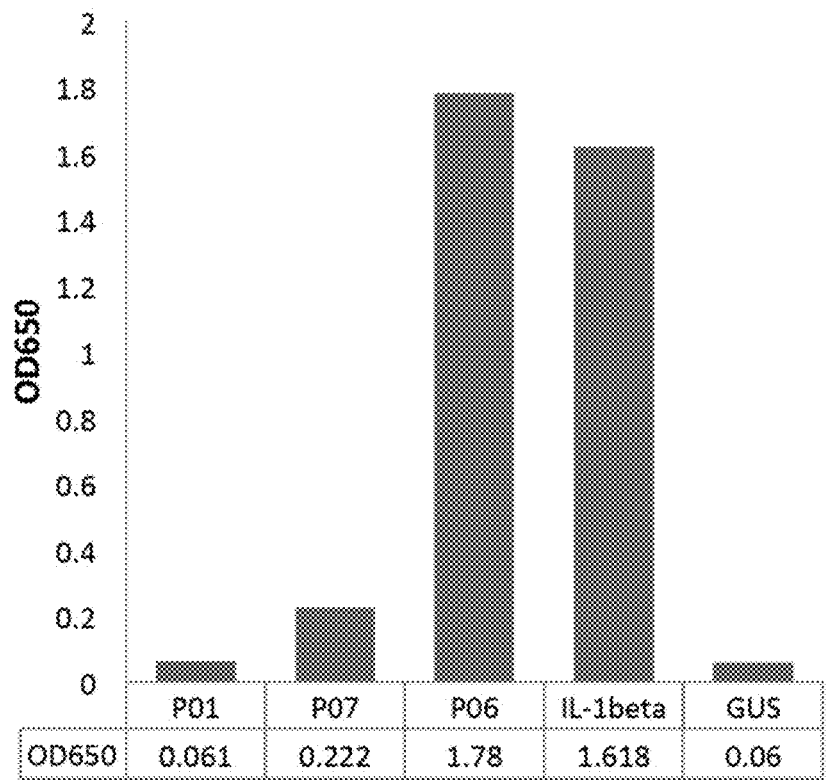
FIG. 7A is a table and accompanying bar graph showing the ability of the P06, P07, and P01 proteins to agonize signaling relative to IL-1β and a negative control, β-glucuronidase (GUS) protein.
Figure 7B:
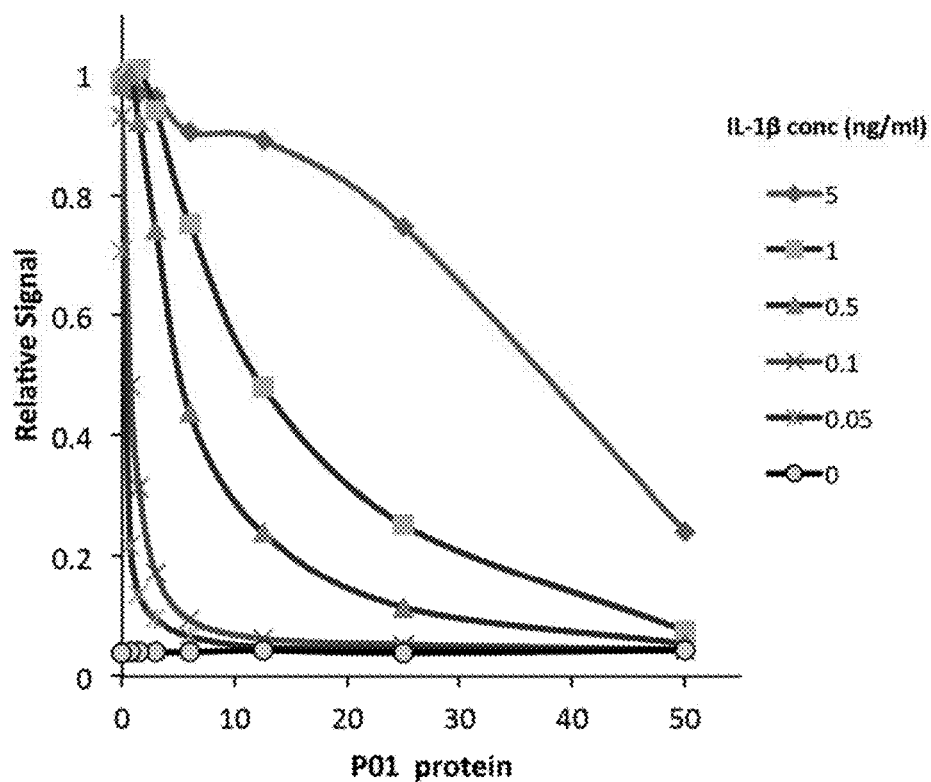
FIG. 7B is a graph depicting antagonism of IL-1β at various IL-1β concentrations by P01.

Results. As shown in FIG. 7A, in this assay, the P06 protein behaved as an IL-1RI agonist, the P07 protein behaved as a partial agonist, and the P01 protein failed to agonize. In fact, the P01 protein behaved as an antagonist when assayed in the presence of IL-1β. FIG. 7B shows antagonism of IL-1β activity by P01 at a range of IL-1β protein concentrations using the HEKBlue™ cell assay above. Antagonism increased with increasing amounts of P01 (x-axis reflects microliters of supernatant containing P01).

Figure 8A:
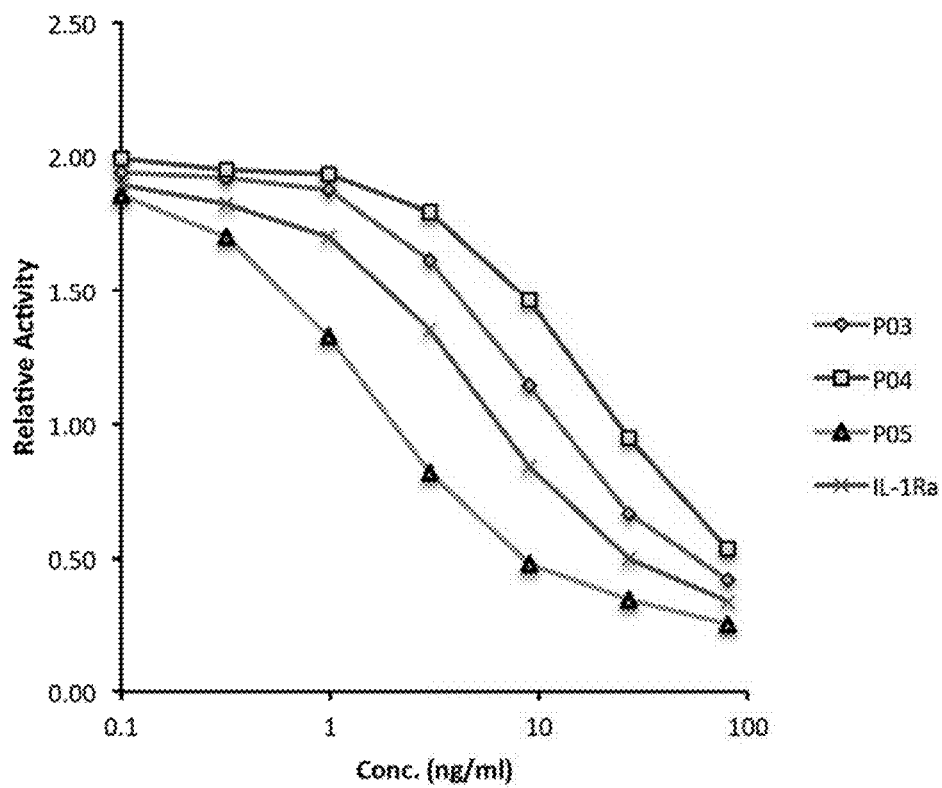
FIG. 8A is a graph depicting IL-1β antagonism by P03 (hexa-histidine (SEQ ID NO:42) tagged), P04 (hexa-histidine (SEQ ID NO:42) tagged), P05 (hexa-histidine (SEQ ID NO:42) tagged), and IL-1Ra in the presence of 0.1 ng/ml IL-1β (human).
Figure 8B:
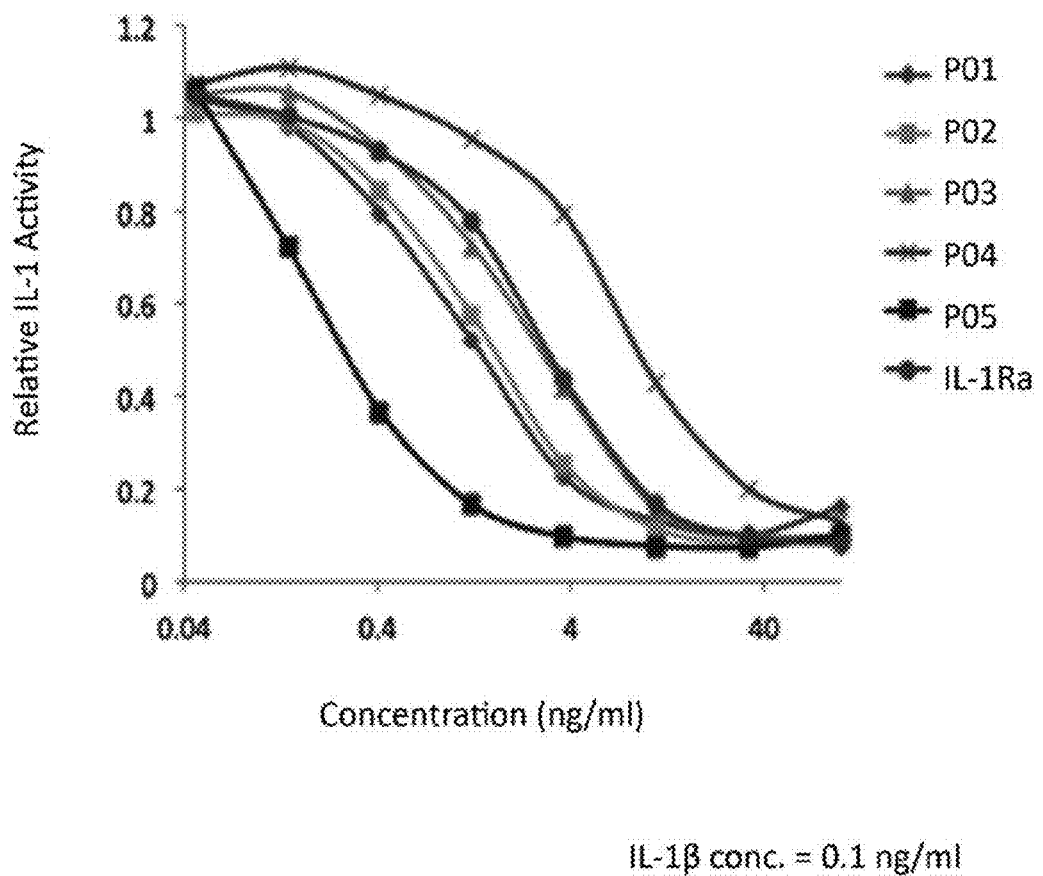
FIG. 8B is a graph depicting IL-1β antagonism by lysates containing untagged forms of P01, P02, P03, P04, and P05, and IL-1Ra in the presence of 0.1 ng/ml IL-1β (human) and using estimates of the concentration of protein in the respective lysates.

The proteins P01, P02, P03, P04, and P05 each antagonized IL-1β activity. See FIGS. 8A and 8B, for example. The IC50 of P05 was less than about 5 ng/ml. P05 was test for ability to agonize IL-1RI in this assay and was not observed to have any detectable agonistic activity even at the highest concentrations tested, 1 mg/ml. P01, P02, P03, P04, and P05 also inhibited IL-1β induced IL-6 expression in MG-63 cells, a human osteosarcoma cell line that is responsive to IL-1β. In a murine model of dry eye disease, hexa-histidine (SEQ ID NO:42) tagged P05 was observed to have biological activity. See also Example 8 below regarding untagged P05.

Example 4

Figure 9A:
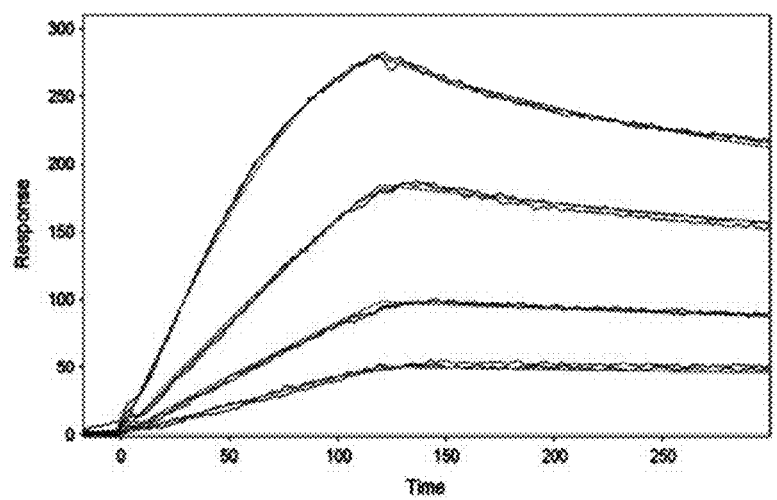
FIG. 9A-D contain graphs of SPR data showing binding kinetics to immobilized soluble IL-1RI for the following proteins: IL-1β (FIG. 9A), IL-1Ra (FIG. 9B), P04 (FIG. 9C), and P05 (FIG. 9D).

The binding properties of proteins for soluble recombinant human IL-1RI (corresponding to the extracellular domain of IL-1RI) were evaluated using surface plasmon resonance with a Reichert SR7000DC Dual Channel SPR system. Binding was evaluated in phosphate buffered saline with 0.005% Tween 20. IL-1β was observed to have a $K_D$ of between 8-9 nM and a dissociation constant ($K_d$) of between $2\text{-}3 \times 10^{-3}$ $s^{-1}$, and in another experiment a $K_D$ of about 2 nM, an association constant of $1.3\text{-}1.5 \times 10^6$ $M^{-1}$ $s^{-1}$, and a dissociation constant ($K_d$) of about $2.9\text{-}3.0 \times 10^{-3}$ $s^{-1}$. See FIG. 9A. The P01 protein bound with similar association kinetics as IL-1β, but did not dissociate during of the dissociation phase of the binding experiment (about 180 seconds). Thus, the P01 protein bound to IL-1RI with a greater affinity than did IL-1β under similar conditions.

Figure 9B:
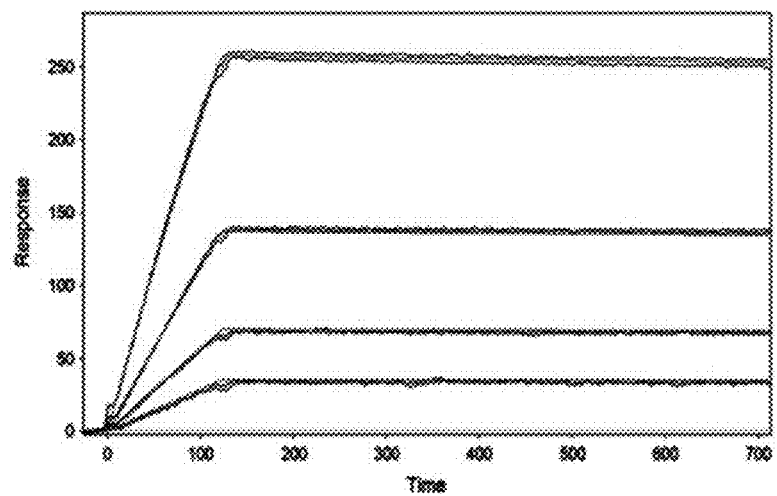
Figure 9C:
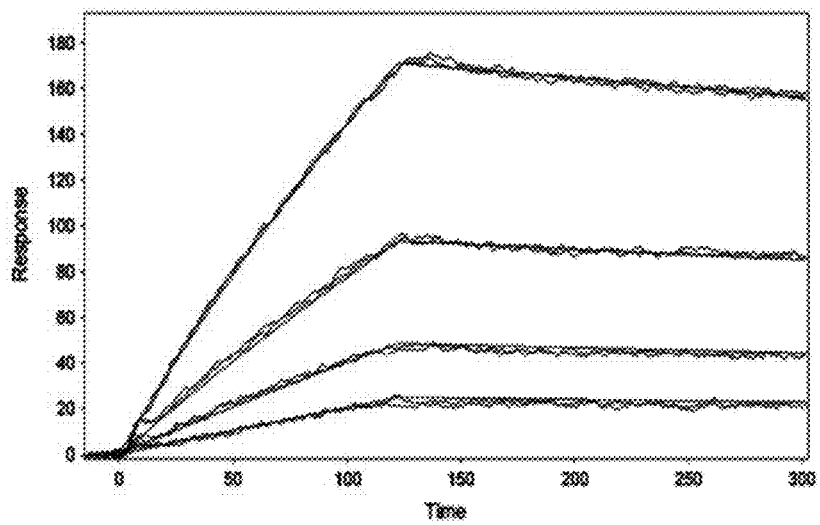
Figure 9D:
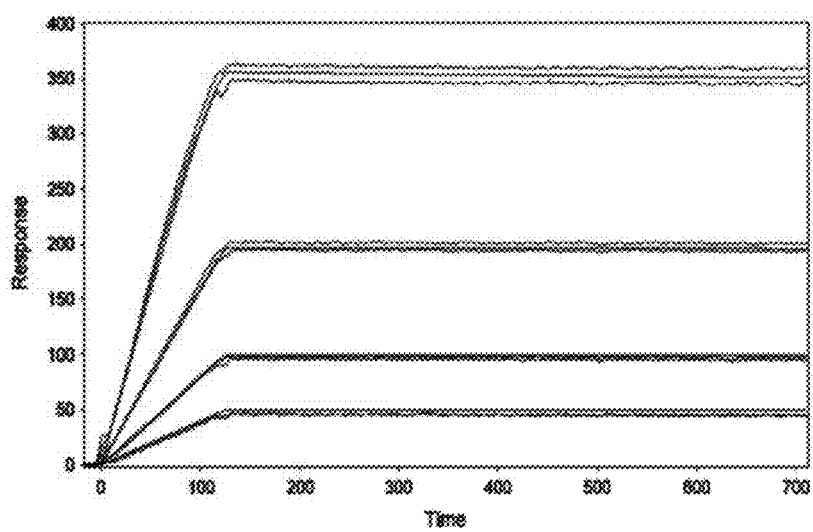

Binding of IL-1Ra was observed to have a $K_D$ of about 0.33 nM, an association constant ($K_a$) of about $2 \times 10^5$ $M^{-1}$ $s^{-1}$, and a dissociation constant ($K_d$) of about $6.6 \times 10^{-5}$ $s^{-1}$. See FIG. 9B. Chimeric cytokine domains P01, P02, P03, P04, and P05 were observed to have $K_D$ ranging from about 12-1700 μM, an association constant ($K_a$) ranging from about $3 \times 10^4$ $M^{-1}$ $s^{-1}$ to $3 \times 10^6$ $M^{-1}$ $s^{-1}$, and a dissociation constant ($K_d$) ranging from about $2 \times 10^{-6}$ to $1 \times 10^{-3}$ $s^{-1}$. See for example FIGS. 9C and 9D and Table 7 below.

TABLE 7

| Protein | $k_a$ ($M^{-1}s^{-1}$) | $K_d$ ($s^{-1}$) | $K_D$ (pM) |
|---|---|---|---|
| IL-1β | $1.47 \times 10^6$ $M^{-1}s^{-1}$ | $2.95 \times 10^{-3}$ $s^{-1}$ | 2010 |
| IL-1Ra | $2.01 \times 10^5$ $M^{-1}s^{-1}$ | $6.58 \times 10^{-5}$ $s^{-1}$ | 326 |
| P01 | $4.93 \times 10^4$ $M^{-1}s^{-1}$ | $2.32 \times 10^{-5}$ $s^{-1}$ | 470 |
| P02 | $3.39 \times 10^4$ $M^{-1}s^{-1}$ | $2.16 \times 10^{-5}$ $s^{-1}$ | 636 |
| P03 | $4.1 \times 10^6$ $M^{-1}s^{-1}$ | $1.2 \times 10^{-3}$ $s^{-1}$ | 290 |
| P04 | $3.00 \times 10^4$ $M^{-1}s^{-1}$ | $5.14 \times 10^{-4}$ $s^{-1}$ | 1714 |
| P05 | $3.47 \times 10^6$ $M^{-1}s^{-1}$ | $4.15 \times 10^{-5}$ $s^{-1}$ | 12 |
| P06 | $4.8 \times 10^6$ $M^{-1}s^{-1}$ | $1.7 \times 10^{-3}$ $s^{-1}$ | 410 |
| P07 | $1.58 \times 10^4$ $M^{-1}s^{-1}$ | $1.46 \times 10^{-3}$ $s^{-1}$ | 92553 |

Example 5

Additional exemplary chimeric IL-1 family proteins also include the following:

P08

SEQ ID NO: 32
APVRSLAFRIWDVNQKTFYLRNNQLVAGYLQGPNVNLEEKFSMSFVQG
EESNDKIPVALGLKEKNLYLSCVLKDDKPTLQLESVDPKNYPKKKMEK
RFVFNKIEINNKLEFESAQFPNWFLCTAMEADQPVSLTNMPDEGVMVT
KFYMQFVSS

P09

SEQ ID NO: 33
APVRSQAFRIWDVNQKTFYLRNNQLVAGYLQGPNVNLEEKFSMSFVQG
EESNDKIPVALGLKEKNLYLSCVLKDDKPTLQLESVDPKNYPKKKMEK
RFVFNKIEINNKLEFESAQFPNWFLCTAMEADQPVSLTNMPDEGVMVT
KFYMQFVSS

P10

SEQ ID NO: 34
APVRSLAFRIWDVNQKTFYLRNNQLVAGYLQGPNVNLEEKIDVSFVQG
EESNDKIPVALGLKEKNLYLSCVLKDDKPTLQLESVDPKNYPKKKMEK
RFVFNKIEINNKLEFESAQFPNWFLCTAMEADQPVSLTNMPDEGVMVT
KFYMQFVSS

P11

SEQ ID NO: 35
APVRSLNCRIWDVNQKTFYLRNNQLVAGYLQGPNVNLEEKIDVSFVQG
EESNDKIPVALGLKEKNLYLSCVLKDDKPTLQLESVDPKNYPKKKMEK
RFVFNKIEINNKLEFESAQFPNWFLCTAMEADQPVSLTNMPDEGVMVT
KFYMQFVSS

-continued

P12

SEQ ID NO: 36
APVRSLNCRIWDVNQKTFYLRNNQLVAGYLQGPNVNLEEKFSMSFVQG
EESNDKIPVALGLKEKNLYLSCVLKDDKPTLQLESVDPKNYPKKKMEK
RFVFNKIEINNKLEFESAQFPNWFLCTAMEADQPVSLTNMPDEGVMVT
KFTMQFVSS

P13

SEQ ID NO: 37
APVRSLAFRIWDVNQKTFYLRNNQLVAGYLQGPNVNLEEKFSMSFVQG
EESNDKIPVALGLKEKNLYLSCVLKDDKPTLQLESVDPKNYPKKKMEK
RFVFNKIEINNKLEFESAQFPNWFLCTAMEADQPVSLTNMPDEGVMVT
KFYFQED

P14

SEQ ID NO: 38
APVRSLNCRIWDVNQKTFYLRNNQLVAGYLQGPNVNLEEKFSMSFVQG
EESNDKIPVALGLKEKNLYLSCVLKDDKPTLQLESVDPKNYPKKKMEK
RFVFNKIEINNKLEFESAQFPNWFLCTAMEADQPVSLTNMPDEGVMVT
KFYFQED

The polypeptide below is a chimeric domain that includes at least two segments from IL-1α and at least two segments from IL-1Ra.

SEQ ID NO: 39

```
SAPFSFLSNVKYNFMRIIKYEFRIWDVNQKTFYLRNNQLVAGYLQGPNVN

LEEKFDMGAYKSSKDDAKITVILRISKTQLYVTAQDEDQPVLLKEMPEIP

KTITGSETNLLFFWETHGTKNYFTSVAHPNLFLCTAMEADQPVSLTNMPD

EGVMVTKFYILENQA
```

Example 6

A circularly permuted IL-1 chimeric domain can be constructed by linking the N-terminus to the C-terminus of the molecule using a linker sequence and selecting a new location for each of the termini. For proteins having termini derived from IL-1β, the linker length can be between five to ten, e.g., about seven amino acids. Preferred locations for new termini are in loops which face away from the receptors, such as the β6-β7 loop (e.g., amino acids corresponding to 71-80 of SEQ ID NO:1) or the β7-β8 loop (e.g., amino acids corresponding to 84-99 of SEQ ID NO:1).

Examples of such circularly permuted IL-1 chimeric domains include:

(SEQ ID NO: 40)

```
DKPTLQLESVDPKNYPKKKMEKRFVFNKIEINNKLEFESAQFPNWFLCTA
MEADQPVSLTNMPDEGVMVTKFYMQFVSSGGSGGGSAPVRSLNCRIWDVN
QKTFYLRNNQLVAGYLQGPNVNLEEKFSMSFVQGEESNDKIPVALGLKEK
NLYLSCVLKD
``` and (SEQ ID NO: 41)

```
NYPKKKMEKRFVFNKIEINNKLEFESAQFPNWFLCTAMEADQPVSLTNMP
DEGVMVTKFYMQFVSSGGSGGGSAPVRSLNCRIWDVNQKTFYLRNNQLVA
GYLQGPNVNLEEKFSMSFVQGEESNDKIPVALGLKEKNLYLSCVLKDDKP
TLQLESVDPK
```

Example 7

Proteins P03, P04, P05, mIL-1Ra (methionyl IL-1Ra), and IL-1β were prepared in phosphate-buffered saline (PBS), pH 7.4, at 0.5 mg/ml. The proteins were combined with SYPRO orange dye (Invitrogen, CA) at a 1:500 dilution of the stock concentration and subject to differential scanning fluorimetry. See, e.g., He et al. (2010) J. Pharm.

Sciences, 99 1707-1720. Fluorescence measurements were monitored using an Agilent Mx3005 QPCR machine as the temperature was increased from 25° C. to 95° C. at a rate of 1° C. per minute. Melting temperature ($T_m$) values were derived from the maxima value of the first derivative of the fluorescence transition. The proteins P03, P04, and P05 were observed to have an onset of unfolding of greater than 50° C. and as high as 59° C., and $T_m$ of greater than 59, 60, 62, and 64° C. Results are shown in Table 8 below and FIGS. 10A & 10B:

TABLE 8

| Protein | $T_m$ (° C.) | Onset of unfolding (° C.) |
|---|---|---|
| mIL-1Ra | 56 | 48 |
| IL-1β | 56 | 41 |
| P03 | 65 | 59 |
| P04 | 60 | 51 |
| P05 | 65 | 59 |

P04 has a $T_m$ that is about 4 degrees higher than mIL-1Ra and IL-1β and exhibits an onset of unfolding about 3 degrees higher than mIL-1Ra and about 10 degrees higher than IL-1β. P03 and P05 have a $T_m$ that is about 9 degrees higher than mIL-1Ra and IL-1β and exhibit an onset of unfolding about 11 degrees higher than mIL-1Ra and about 18 degrees higher than IL-1β.

Example 8

Purified P05 (lacking a hexa-histidine tag (SEQ ID NO:42)) was prepared in 1.25×PBS and tested in a murine model of dry eye disease. In this model, female C57BL/6 mice 6 to 10 weeks of age from Jackson Laboratories (acclimated 1 to 2 weeks in an animal holding room with ≥30% relative humidity, hydrogel food supplement, and envirodry environment enrichment) were pre-screened for fluorescein staining on Day 0. For fluorescein staining, freshly made fluorescein diluted in WFI $H_2O$ at 10 mg/mL was administered at 0.4 µL to each eye. Approximately 8-13 minutes after administration, eyes were scored using an Olympus fluorescent dissecting microscope. Punctuate staining was recorded using the standardized National Eye Institute (NEI) grading system of 0-3 for each of the five areas into which the corneal surface has been divided (score range 0-15/eye). Using a teaching bridge, two masked scorers evaluated mice at the same time to give a single collective score for each eye.

Mice with scores ≤7 for each eye (out of a maximal score of 15) were placed in a dry eye chamber (20%±2% humidity and constant air flow ~21 Umin/cage) on day 1 and were maintained in this chamber during the course of the experiment (except for examination). On day 3, mice were scored again and randomized into treatment groups with 8 to 10 mice/group. Mice were randomized such that each cage of 4 to 5 mice had approximately the same mean disease score. Beginning on day 3 and after randomization, mice were topically administered P05 or vehicle (1.25×PBS) in an eye drop at 3 µL/eye BID frequency. Mice were examined and scored on days 7, 9, and 11 for corneal fluorescein staining as described above. Scorers were blinded as to the treatment groups during the course of the experiment.

FIG. 11A is a bar graph of mean corneal staining score±SEM at day 0, 3, 7, 9, and 11 for mice from two identical experiments under the following bid treatments: no treatment, vehicle (1.25×PBS), and 10 mg/ml (1%) P05. 10 mg/ml P05 significantly reduced corneal staining on days 7, 9, and 11 of the experiment. Efficacy as evaluated by a reduction in corneal staining was also observed with doses as low as 0.1 mg/ml P05. Recombinant IL-1Ra produced in *E. coli* also moderately reduced corneal staining in the animal model.

Figure 10A:
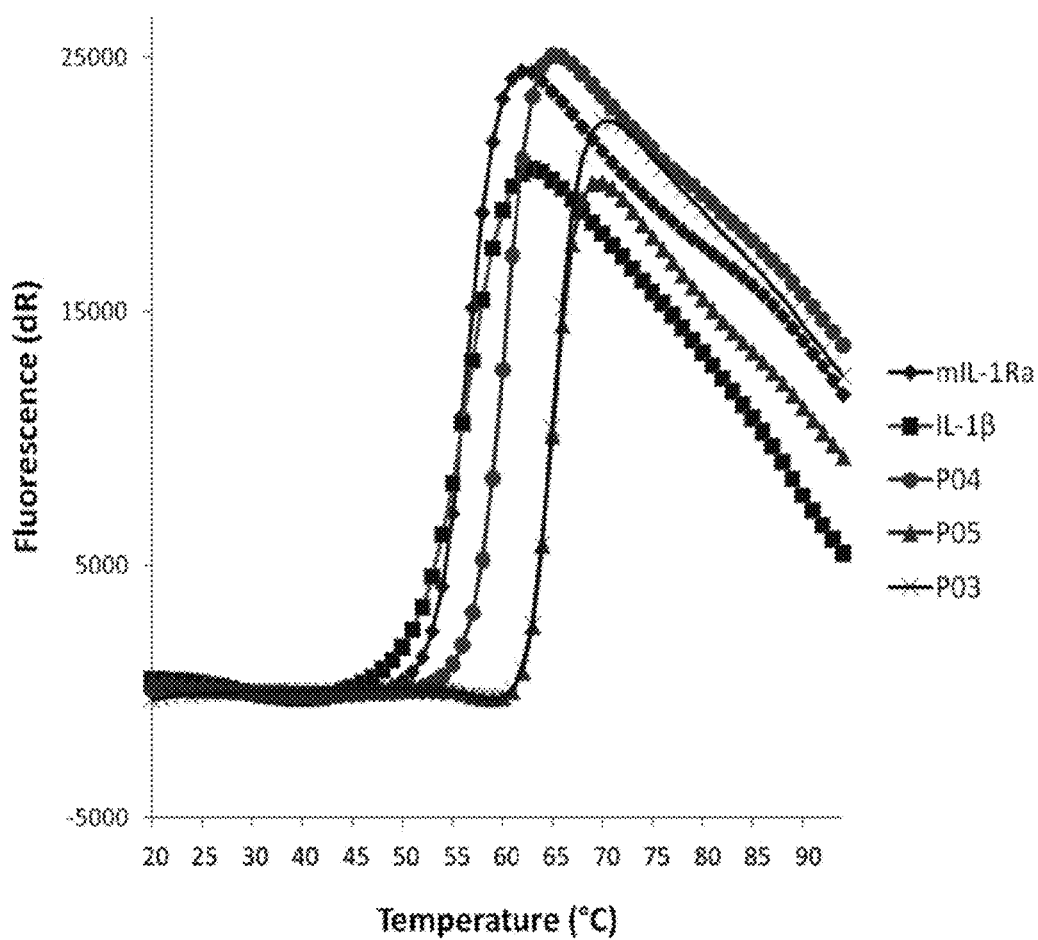
FIG. 10A is a graph depicting thermal denaturation of IL-1Ra, IL-1β, P03, P04, and P05 as described in Example 7.
Figure 10B:
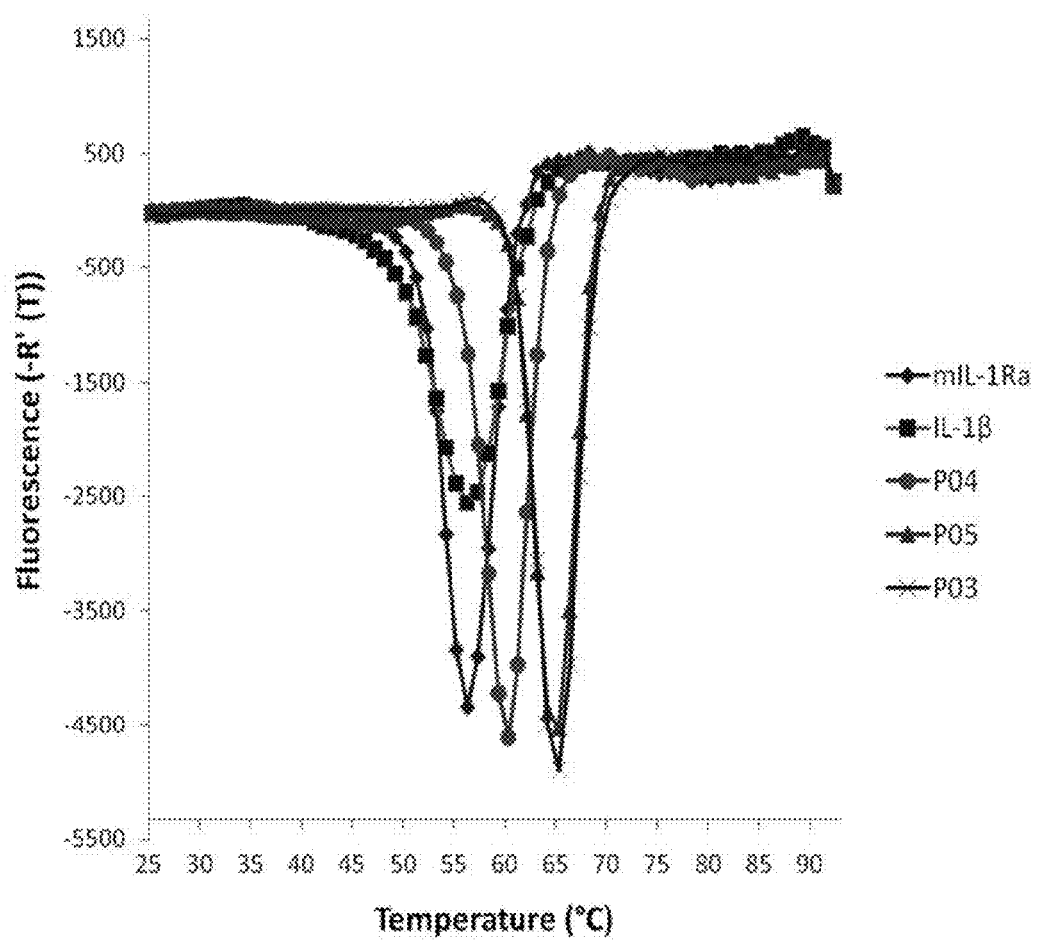
FIG. 10B depicts the negative first derivative of the graph in FIG. 10A.
Figure 11A:
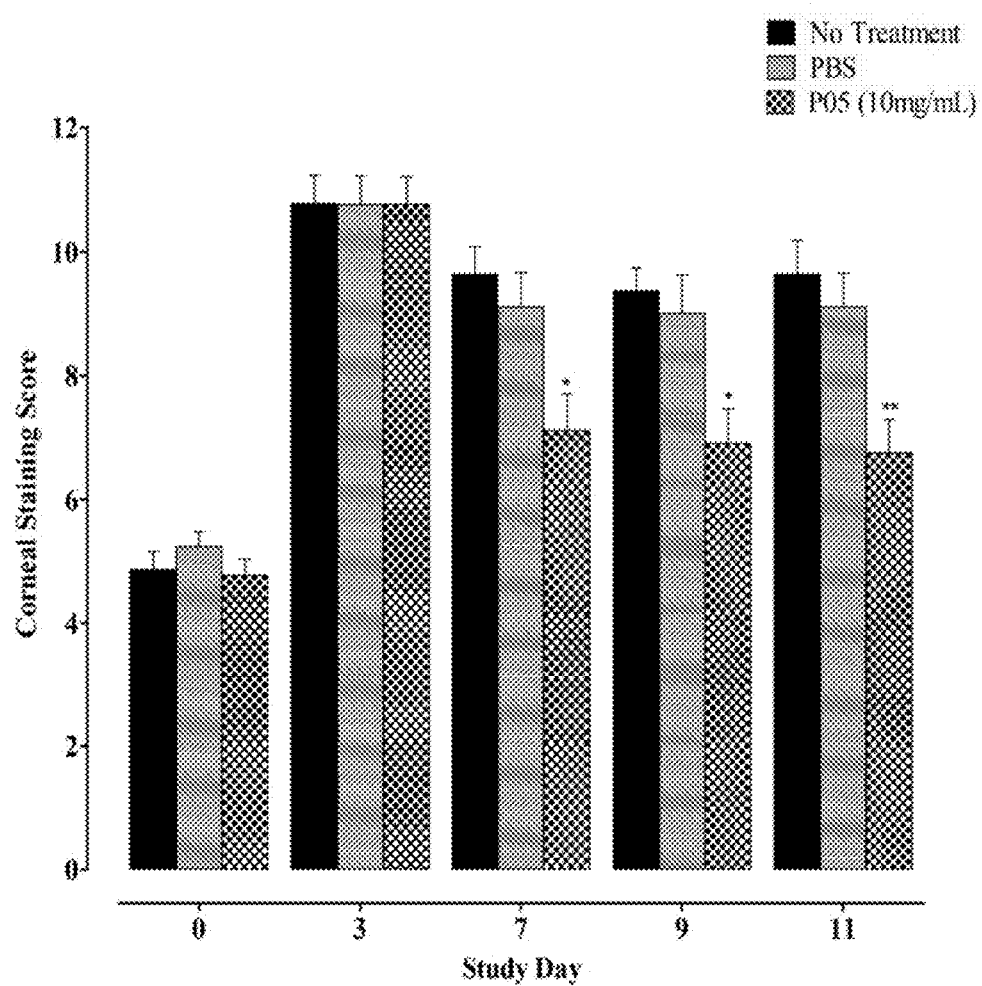
FIG. 11A is a bar graph showing the mean corneal staining score±SEM as tested by fluorescein staining of the cornea per eye of two independent studies, on days 0, 3, 7, 9, and 11 for mice in a dry eye model. The mice received no treatment (n=18), 10 mg/ml P05 (n=19), or 1.25×PBS, the vehicle (n=20). Asterisks indicate statistical significance of P05 relative to vehicle as follows: * ($P<0.05$) and ** ($P<0.005$).
Figure 11B:
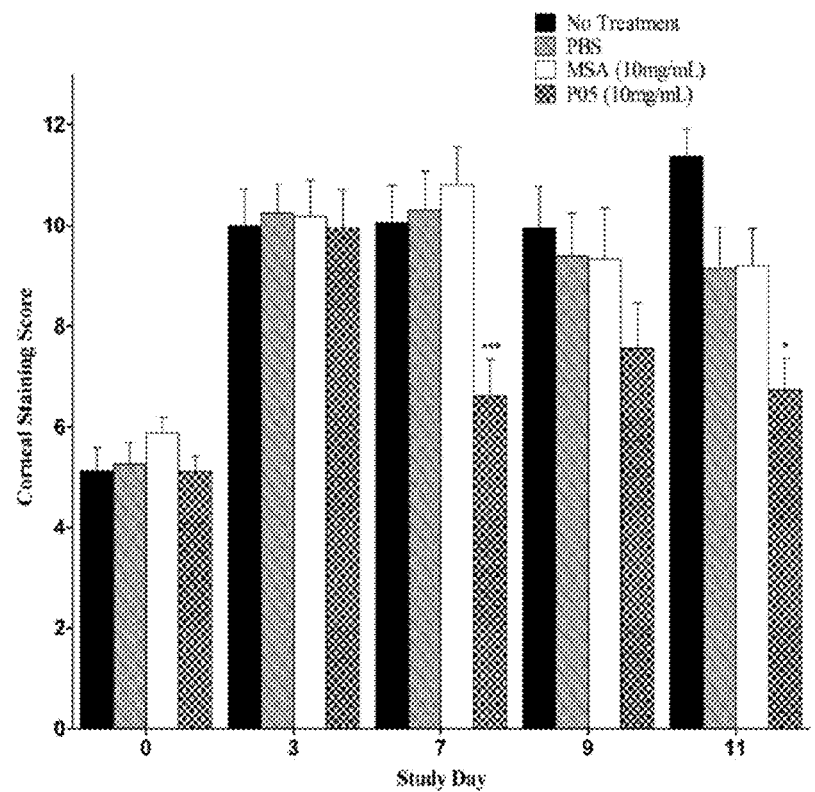
FIG. 11B is a bar graph representing data from a separate experiment showing mean corneal staining score±SEM of the cornea per eye, on days 0, 3, 7, 9, and 11 for mice in a dry eye model. The mice received no treatment (n=8), 1.25×PBS vehicle (n=8), 10 mg/ml murine serum albumin (MSA) (n=8), or 10 mg/ml P05 (n=9). Asterisks indicate statistical significance of P05 relative to murine serum albumin as follows: * ($P<0.05$) and *** ($P<0.0005$).
Figure 11C:
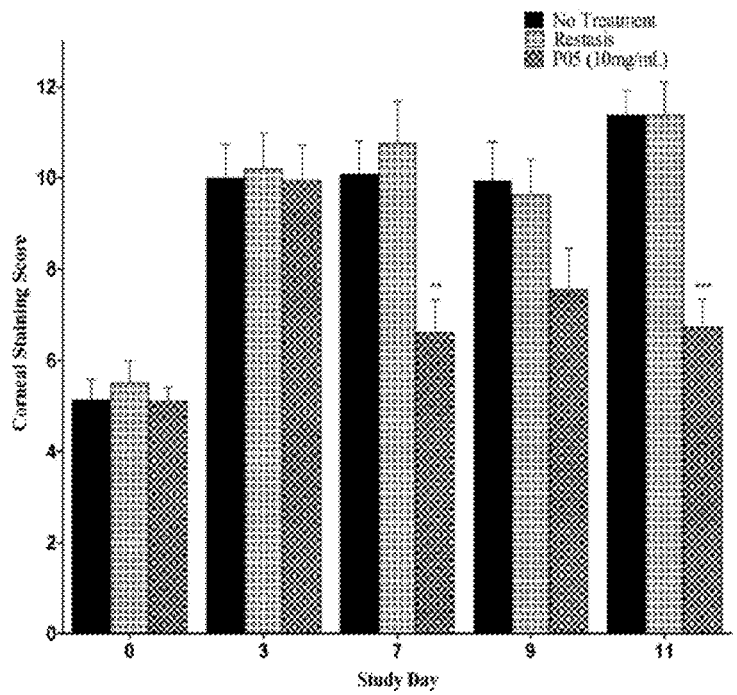
FIG. 11C is a bar graph including data for mice that were treated with Restasis® (0.05% cyclosporine emulsion) (n=8) in the same experiment as FIG. 11B. Asterisks indicate statistical significance of P05 relative to Restasis® as follows:  ($P<0.005$) and * ($P<0.0005$).

As shown in FIG. 11B, the effect of 10 mg/ml P05 was specific based on a comparison to 10 mg/ml murine serum albumin in the same vehicle. No effect was seen with 10 mg/ml murine serum albumin (MSA) relative to vehicle, and the effect of 10 mg/ml P05 was statistically significant relative to 10 mg/ml murine serum albumin. As shown in FIG. 11C, 10 mg/ml P05 was also compared to 0.05% cyclosporine in an ophthalmic emulsion (Restasis®). Whereas P05 reduced corneal staining, no effect was observed for the 0.05% cyclosporine ophthalmic emulsion after ~1 week of bid dosing.

Example 9

A capture step has been developed for the purification of P05 produced by fermentation in BLR(DE3) *E. coli* cells. The elution conditions were defined through a statistical design of experiment approach (DOE) on a 1 mL column. The optimized conditions were performed on an intermediate scale (10 mL column).

The product is extracted by microfluidization in a lysis buffer consisting of 20 mM Tris at pH 7.0 with 10 mM EDTA added. The clarified lysate is adjusted to a pH of 5.3 and a conductivity of 3 mS/cm. The conditioned lysate is loaded onto a PorosXS (strong cation exchange resin) with a 2 min residence time to a capacity of 25-30 mg P05/mL column. The column is washed with equilibration buffer to remove unbound species. A second wash at pH 6.0 and 3 mS/cm is implemented to remove a population of impurities. The product is eluted at pH 6.0 and 6.6 mS/cm. A product related species is eluted at pH 6.0 and 12.4 mS/cm. The column is cleaned with a high salt buffer and NaOH.

P05 is a 17 kDa protein with a pI of 6.58. The pI of the des-ALA species is 6.8 and is readily resolved by analytical weak cation exchange chromatography. This species is likely to be a product of aminopeptidase P activity found in *E. coli*. The species can be identified by mass spectroscopy, peptide mapping, and HPLC methods.

Chromatographic Materials.

PorosXS is based on a crosslinked poly(styrene-divinyl-benzene) bead with a nominal 50 μm particle size. The chromatographic matrix has sulfopropyl surface chemistry and was designed to tolerate elevated levels of salt during binding. The PorosXS (CN 4404339, Life Technologies) material was procured as a bulk slurry and packed into a 5×50 mm Tricorn column (CN 28-4064-09, GE Healthcare) with a final column volume of 1 mL (5 cm bed height) or into a 10×150 mm Tricorn column (CN 28-4064-16, GE Healthcare) packed to a final volume of 10.5 mL (13.4 cm bed height).

Buffers.

All buffers were prepared with MilliQ water volumetrically. To reach the desired pH, either 10 N HCl or 1 M NaOH (made from a stock solution of 10 M NaOH) was added to titrate the buffer. After preparation, all buffers were filtered through 0.2 μm PES bottle top filters. All pH and conductivity measurements were performed at room temperature (~20-25° C.).

PorosXS Buffers: CEX equilibration buffer—10 mM acetic acid (HoAC) with 21 mM NaCl made by adding 0.57 mL of glacial acetic acid and 2.44 g of NaCl per L of buffer. The final pH was 5.3 and the final conductivity was 3 mS/cm.

CEX wash buffer—100 mM MOPS with 22 mM NaCl made by adding 19.5 g of MOPS free acid, 1.5 g of MOPS sodium salt, and 1.28 g of NaCl per L of buffer. The final pH was 5.7-6.6 (as desired) and the final conductivity was 3 mS/cm.

CEX elution buffer—100 mM MOPS with 118 mM NaCl made by adding 19.5 g of MOPS free acid, 1.5 g of MOPS sodium salt, and 6.93 g of NaCl per L of buffer. The final pH was 5.7-6.6 (as desired) and the final conductivity was 12.4 mS/cm.

CEX strip buffer—10 mM acetic acid with 3 M NaCl made by adding 0.57 mL of glacial acetic acid and 175 g of NaCl per L of buffer. The final pH was 5.3 and the final conductivity was 188 mS/cm.

Lysate Preparation.

The pH of the lysate was adjusted using 200 mM acetic acid at pH 4.5 made by mixing 11.5 mL of glacial acetic acid per L of buffer. The solution was titrated to a final pH of 4.5 using 1 M NaOH. This solution was used in order to avoid localized precipitation due to low pH of concentrated or strong acids.

The load material for these experiments was an extract from a 2 L fed-batch bioreactor run. The extraction of the product from the cell pellet was performed using 20 mM Tris at pH 7.0 with 10 mM EDTA added. The fresh extract was diluted to a conductivity of 3 mS/cm with MilliQ water (typically 1:1-1.5 dilution). The diluted extract was frozen at −20° C. in 41 mL aliquots. To prepare the load, an aliquot was thawed at room temperature and titrated to pH 5.3 using 200 mM acetic acid at pH 4.5. Small adjustments in conductivity were made by addition of MilliQ water when needed after titration. Finally, the load was diluted 2.5× to a concentration of ~1.7 g/L using CEX equilibration buffer. The load was sterile filtered through a 0.8/0.2 μm filter. The conditioned load was used the same day as prepared.

Host Cell Protein Determination.

The host cell protein (HCP) levels were determined by an enzyme-linked immunosorbent assay (ELISA) kit specific for an *E. coli* expression system (CN F410, Cygnus Technologies). The protocol supplied with the kit was followed exactly. Samples to be assayed for HCP levels were diluted using sample diluent (CN I028, Cygnus Technologies) with a minimum dilution of 10×. Samples were typically run at two dilutions and plated in duplicate for each dilution. The level of HCP is represented in terms of parts per million (ppm) or ng-HCP/mg-product.

SDS-PAGE Analysis.

For purity analysis by sodium dodecyl sulfate polyacrylamide gel electrophoresis (SDS-PAGE), either 1 mm×10 well or 1 mm×15 well NuPAGE 4-12% BisTris gels (CN NP0322Box and NP0323Box, respectively, Invitrogen) are used. The running buffer is 1×MES SDS running buffer prepared from a 20× concentration (CN NP0002, Invitrogen). Novex sharp prestained protein standards (CN 57318, Invitrogen) are used as molecular weight indicators. Samples for analysis were prepared by dilution with MilliQ water to a final volume of 30 μL and 10 μL of 4× Lithium dodecyl sulfate (LDS) (CN NP0008, Invitrogen) was added to a final concentration of 1×. The samples were mixed by vortex for 5 s. Based on the calculated protein concentration from the A280/A320 measurement, a target of 3 μg per well was loaded.

wCEX.

P05 was evaluated by weak cation exchange chromatography (wCEX) using a Dionex ProPac® WCX-10 4×250 mm column (Product Number 054993), with a flow rate of 1.2 mL/min using mobile phase solutions of 10 mM sodium acetate pH 5.5 (buffer A) and 10 mM sodium acetate pH 5.5, 250 mM NaCl (buffer B). A gradient is performed from 10% B to 25% B over 20 minutes. Intact P05 elutes approximately 1.5 to 2.5 minutes before the des-Ala species in the later part of the gradient.

Cation Exchange Capture Chromatography.

Chromatography was performed on an AKTA Explorer 100 chromatography system. A 10 mL PorosXS column was packed. Material was loaded at 40 mg of P05/ml, or can be loaded at 25-30 mg of P05/ml. The chromatography method is summarized in Table 9. The residence time was held constant during loading and elution steps at 2 min. Mock elution pools were made and assayed for product recovery, HCP level, and % intact protein. A total of 2 runs were completed on the 10 mL column with % B at 30% and 35% at pH 6.0.

TABLE 9

| Step | Column volumes (CV) | Buffer |
|---|---|---|
| Equilibration | 10 | 10 mM HoAC + 21 mM NaCl pH 5.3 |
| Load | 40 | Conditioned lysate, 3 mS/cm pH 5.3 |
| Wash #1 | 5-10 | 10 mM HoAC + 21 mM NaCl pH 5.3 |
| Wash #2 | 9-10 | 100 mM MOPS + 22 mM NaCl pH 6.0 (3 mS/cm) |
| Elution #1 | 30 | 100 mM MOPS + 22 mM NaCl pH 6.0 (3 mS/cm) blended with 30-35% 100 mM MOPS + 118 mM NaCl pH 6.0 |
| Elution #2 | 6 | 100 mM MOPS + 118 mM NaCl pH 6.0 |
| Strip | 5-6 | 10 mM HoAC + 3M NaCl pH 5.3 |
| Clean | 20 | 1M NaOH |
| Neutralization (NaCl) | 10 | 100 mM MOPS + 118 mM NaCl pH 6.0 |
| Re-equilibration | 20 | 10 mM HoAC + 21 mM NaCl pH 5.3 |

Wash #2 results in a peak comprised mainly of impurities. Elutions #1 with 30% and 35% B result in >95% pure product by SDS-PAGE analysis. The salt concentration of Wash #2 can be increased by a small amount to remove the shoulder on the elution peak.

Example 10

P04 was purified, and diffraction quality crystals were grown in 25% PEG1500, 0.1 M PCB (pH 4.0) at 20° C. The protein crystallized in the space group $P2_12_12_1$, with typical unit cell dimensions of a=44.5, b=46.4, c=64.8. The crystals diffracted to high resolution, and a dataset extending to 1.47 Å was collected at the Advanced Photon Source, beamline LS-CAT 21ID-F (Chicago Ill., USA). The X-ray structure of P04 was solved by molecular replacement using a model incorporating the relevant portions of known IL-1β and IL-1Ra structures from PDB structures 1ITB and 1IRA (Vigers et al., (1997) Nature 386: 190-194 and Schreuder et al., (1997) Nature 386: 194-200). The final model was refined to a $R_{work}/R_{free}$ of 17.6%/20.4% and contains one P04 molecule (140 residues) and 98 water molecules (Table 10). P04 residues 1-2, 48-49 and 85-93 were not visible in the electron density and are missing in the final model.

TABLE 10

Crystallographic Data Collection and Refinement Statistics

| Data Collection Statistics | |
|---|---|
| Space group | $P2_12_12_1$ |
| Cell dimensions | |
| a, b, c (Å) | 44.5, 46.4, 64.8 |
| α, β, γ (°) | 90, 90, 90 |
| Wavelength (Å) | 0.9787 |
| Resolution (Å) | 50.0-1.47 (1.52-1.47) |
| $R_{merge}$ | 0.039 (0.56) |
| I/σI | 37.7 (2.9) |
| Completeness (%) | 99.8 (100) |
| Redundancy | 6 (5.9) |
| Refinement Statistics | |
| Resolution (Å) | 28.64-1.47 (1.53-1.47) |
| No. of reflections | 22926 |
| $R_{work}/R_{free}$ | 17.6/20.4 |
| Average B (Å) | 22.3 |
| Rmsd bond lengths (Å) | 0.007 |
| Rmsd bond angles (°) | 1.137 |

Numbers in parentheses correspond to highest resolution shell
$R_{merge} = \Sigma_{hkl} [\Sigma_i |I_i - <I>|/\Sigma_i I_i]$
$R_{work} = \Sigma_{hkl}||F_{obs}| - |F_{calc}||/\Sigma_{hkl}|F_{obs}|$ where $F_{obs}$ and $F_{calc}$ are the observed and calculated structure factors
$R_{free}$ was calculated from a subset of reflections (5%) not used for refinement.

Figure 12A:
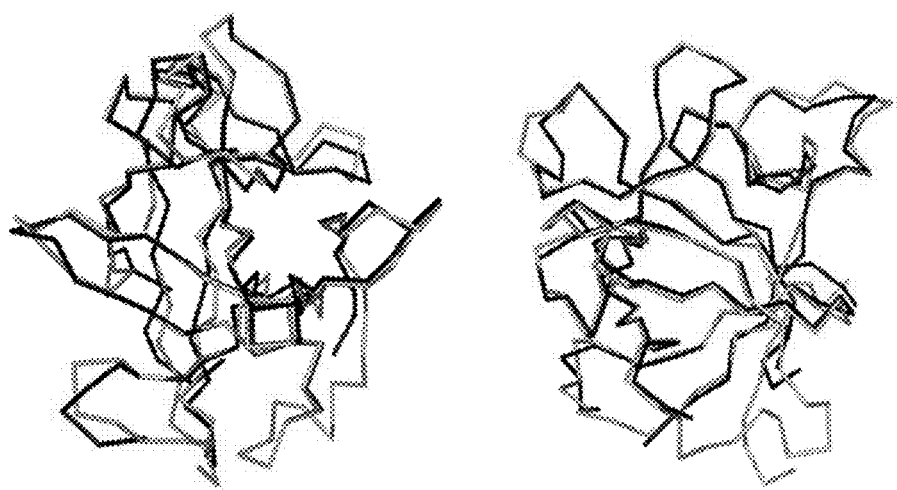
FIG. 12A depicts the structure of the X-ray crystallographic structure (black) of P04 overlaid on a computed model (gray) of its structure.
Figure 12B:
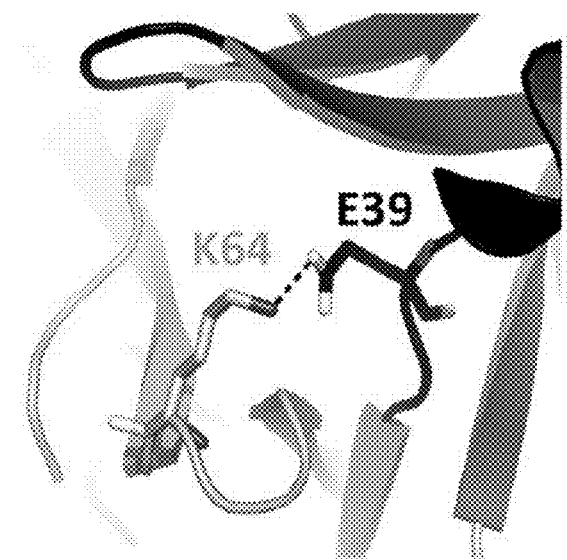
FIG. 12B illustrates interactions between K64 and E39 of P04.
Figure 12C:
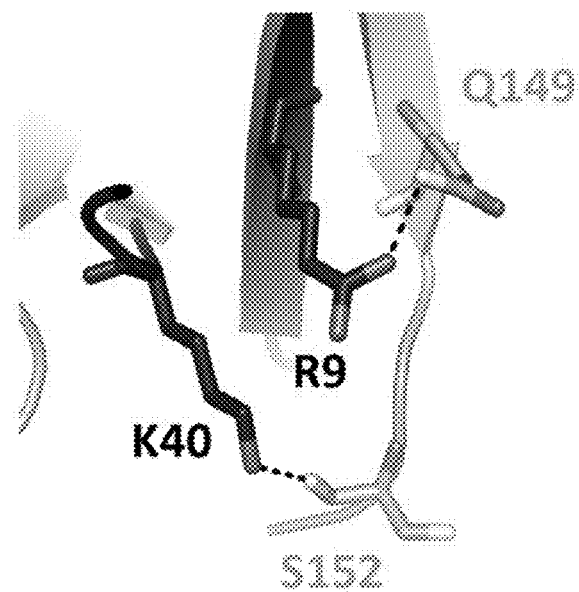
FIG. 12C illustrates interactions between the C-terminal residues Q149 and S152 with K40 and R9 of P04.

The P04 crystal structure has a fold similar to that predicted by the modeling. A view of this structure is shown in FIG. 1. An overlay of the two structures is shown in FIG. 12A. The RMSD for backbone carbons was 1.41 Å and 1.09 Å for the IL-1β and IL-1Ra segments versus the same residues on the respective parent molecules. P04 has at least one unique salt bridge and two unique hydrogen bonds that involve an interaction between a residue derived from IL-1β and a counterpart derived from IL-1Ra: (i) Glu39-Lys64 (Glu39 from IL-1RA; Lys64 from IL-1β) as shown in FIG. 12B, (ii) Arg9-Gln149 (Arg9 from IL-1RA; Gln149 from IL-1β) as shown in FIG. 12C and (iii) Ser152-Lys40 (Ser152 from IL-1RA; Lys50 from IL-1β) as shown in FIG. 12C. These unique interactions can explain P04's increased thermal stability as these interactions are absent in the IL-1β and IL-1Ra structures. The residues involved in these interactions are also present in P03 and P05, proteins that likewise have increased thermal stability.

Other embodiments are within the scope of the following claims.

What is claimed is:

1. An isolated nucleic acid comprising a sequence encoding an amino acid sequence at least 95% identical to SEQ ID NO:21.

2. An isolated nucleic acid vector comprising the nucleic acid of claim 1, wherein the sequence is operably linked to a transcription control sequence.

3. A recombinant host cell comprising a recombinant isolated nucleic acid according to claim 1.

4. The host cell of claim 3 that is an *E. coli* host cell.

5. The isolated nucleic acid of claim 1, wherein the amino acid sequence has 7 or fewer substitutions relative to SEQ ID NO:21.

6. The isolated nucleic acid of claim 1, wherein the amino acid sequence has 6 or fewer substitutions relative to SEQ ID NO:21.

7. The isolated nucleic acid of claim 1, wherein the amino acid sequence has 5 or fewer substitutions relative to SEQ ID NO:21.

8. The isolated nucleic acid of claim 1, wherein the amino acid sequence has 4 or fewer substitutions relative to SEQ ID NO:21.

9. The isolated nucleic acid of claim 1, wherein the amino acid sequence has 3 or fewer substitutions relative to SEQ ID NO:21.

10. The isolated nucleic acid of claim 1, wherein the amino acid sequence has 2 or fewer substitutions relative to SEQ ID NO:21.

11. The isolated nucleic acid of claim 1, wherein the amino acid sequence has 1 substitution relative to SEQ ID NO:21.

12. The isolated nucleic acid of claim 1, wherein the amino acid sequence has 7 or fewer non-conservative substitutions relative to SEQ ID NO:21.

13. The isolated nucleic acid of claim 1, wherein the amino acid sequence has 6 or fewer non-conservative substitutions relative to SEQ ID NO:21.

14. The isolated nucleic acid of claim 1, wherein the amino acid sequence has 5 or fewer non-conservative substitutions relative to SEQ ID NO:21.

15. The isolated nucleic acid of claim 1, wherein the amino acid sequence has 4 or fewer non-conservative substitutions relative to SEQ ID NO:21.

16. The isolated nucleic acid of claim 1, wherein the amino acid sequence has 3 or fewer non-conservative substitutions relative to SEQ ID NO:21.

17. The isolated nucleic acid of claim 1, wherein the amino acid sequence 2 or fewer non-conservative substitutions relative to SEQ ID NO:21.

18. The isolated nucleic acid of claim 1, wherein the amino acid sequence has 1 non-conservative substitution relative to SEQ ID NO:21.

19. The isolated nucleic acid of claim 1, wherein the amino acid sequence consists of a single polypeptide chain that is 150-156 amino acids in length.

20. The isolated nucleic acid of claim 1, further comprising a sequence encoding a hexa-histidine tag.

21. The isolated nucleic acid of claim 1, wherein the amino acid sequence is at least 98% identical to SEQ ID NO:21.

22. The isolated nucleic acid of claim 1, further comprising a sequence encoding a hexa-histidine tag.

23. The isolated nucleic acid of claim 1, consisting of a sequence encoding an amino acid sequence at least 95% identical to SEQ ID NO:21.

24. An isolated nucleic acid comprising a sequence encoding SEQ ID NO:21.

25. An isolated nucleic acid comprising a sequence at least 95% identical to SEQ ID NO:29 and encoding an amino acid sequence at least 95% identical to SEQ ID NO:21.

26. The isolated nucleic acid of claim 25, wherein the sequence is at least 98% identical to SEQ ID NO:29.

27. The isolated nucleic acid of claim 25, wherein the sequence is identical to SEQ ID NO:29.

28. An isolated nucleic acid vector comprising the nucleic acid of claim 25, wherein the sequence is operably linked to a transcription control sequence.

29. A recombinant host cell comprising a recombinant isolated nucleic acid according to claim 25.

* * * * *

SEQUENCE LISTING

<160> NUMBER OF SEQ ID NOS: 58

<210> SEQ ID NO 1
<211> LENGTH: 153
<212> TYPE: PRT
<213> ORGANISM: Homo sapiens

<400> SEQUENCE: 1

```
Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140

Asp Phe Thr Met Gln Phe Val Ser Ser
145                 150

<210> SEQ ID NO 2
<211> LENGTH: 159
<212> TYPE: PRT
<213> ORGANISM: Homo sapiens

<400> SEQUENCE: 2

Ser Ala Pro Phe Ser Phe Leu Ser Asn Val Lys Tyr Asn Phe Met Arg
1               5                   10                  15

Ile Ile Lys Tyr Glu Phe Ile Leu Asn Asp Ala Leu Asn Gln Ser Ile
            20                  25                  30

Ile Arg Ala Asn Asp Gln Tyr Leu Thr Ala Ala Ala Leu His Asn Leu
        35                  40                  45

Asp Glu Ala Val Lys Phe Asp Met Gly Ala Tyr Lys Ser Ser Lys Asp
    50                  55                  60

Asp Ala Lys Ile Thr Val Ile Leu Arg Ile Ser Lys Thr Gln Leu Tyr
65                  70                  75                  80

Val Thr Ala Gln Asp Glu Asp Gln Pro Val Leu Leu Lys Glu Met Pro
                85                  90                  95

Glu Ile Pro Lys Thr Ile Thr Gly Ser Glu Thr Asn Leu Leu Phe Phe
            100                 105                 110

Trp Glu Thr His Gly Thr Lys Asn Tyr Phe Thr Ser Val Ala His Pro
        115                 120                 125

Asn Leu Phe Ile Ala Thr Lys Gln Asp Tyr Trp Val Cys Leu Ala Gly
    130                 135                 140

Gly Pro Pro Ser Ile Thr Asp Phe Gln Ile Leu Glu Asn Gln Ala
145                 150                 155

<210> SEQ ID NO 3
<211> LENGTH: 151
<212> TYPE: PRT
<213> ORGANISM: Homo sapiens

<400> SEQUENCE: 3

Arg Pro Ser Gly Arg Lys Ser Ser Lys Met Gln Ala Phe Arg Ile Trp
1               5                   10                  15
```

```
Asp Val Asn Gln Lys Thr Phe Tyr Leu Arg Asn Asn Gln Leu Val Ala
            20                  25                  30

Gly Tyr Leu Gln Gly Pro Asn Val Asn Leu Glu Glu Lys Ile Asp Val
        35                  40                  45

Val Pro Ile Glu Pro His Ala Leu Phe Leu Gly Ile His Gly Gly Lys
    50                  55                  60

Met Cys Leu Ser Cys Val Lys Ser Gly Asp Glu Thr Arg Leu Gln Leu
65                  70                  75                  80

Glu Ala Val Asn Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp
145                 150

<210> SEQ ID NO 4
<211> LENGTH: 160
<212> TYPE: PRT
<213> ORGANISM: Homo sapiens

<400> SEQUENCE: 4

Ser Ser Ile Thr Gly Ile Ser Pro Ile Thr Glu Tyr Leu Ala Ser Leu
1               5                   10                  15

Ser Thr Tyr Asn Asp Gln Ser Ile Thr Phe Ala Leu Glu Asp Glu Ser
            20                  25                  30

Tyr Glu Ile Tyr Val Glu Asp Leu Lys Lys Asp Glu Lys Lys Asp Lys
        35                  40                  45

Val Leu Leu Ser Tyr Tyr Glu Ser Gln His Pro Ser Asn Glu Ser Gly
    50                  55                  60

Asp Gly Val Asp Gly Lys Met Leu Met Val Thr Leu Ser Pro Thr Lys
65                  70                  75                  80

Asp Phe Trp Leu His Ala Asn Asn Lys Glu His Ser Val Glu Leu His
                85                  90                  95

Lys Cys Glu Lys Pro Leu Pro Asp Gln Ala Phe Phe Val Leu His Asn
            100                 105                 110

Met His Ser Asn Cys Val Ser Phe Glu Cys Lys Thr Asp Pro Gly Val
        115                 120                 125

Phe Ile Gly Val Lys Asp Asn His Leu Ala Leu Ile Lys Val Asp Ser
    130                 135                 140

Ser Glu Asn Leu Cys Thr Glu Asn Ile Leu Phe Lys Leu Ser Glu Thr
145                 150                 155                 160

<210> SEQ ID NO 5
<211> LENGTH: 154
<212> TYPE: PRT
<213> ORGANISM: Homo sapiens

<400> SEQUENCE: 5

Val Leu Ser Gly Ala Leu Cys Phe Arg Met Lys Asp Ser Ala Leu Lys
1               5                   10                  15

Val Leu Tyr Leu His Asn Asn Gln Leu Leu Ala Gly Gly Leu His Ala
            20                  25                  30
```

```
Gly Lys Val Ile Lys Gly Glu Ile Ser Val Pro Asn Arg Trp
            35                  40                  45

Leu Asp Ala Ser Leu Ser Pro Val Ile Leu Gly Val Gln Gly Gly Ser
 50                  55                  60

Gln Cys Leu Ser Cys Gly Val Gly Gln Glu Pro Thr Leu Thr Leu Glu
 65                  70                  75                  80

Pro Val Asn Ile Met Glu Leu Tyr Leu Gly Ala Lys Glu Ser Lys Ser
                 85                  90                  95

Phe Thr Phe Tyr Arg Arg Asp Met Gly Leu Thr Ser Ser Phe Glu Ser
                100                 105                 110

Ala Ala Tyr Pro Gly Trp Phe Leu Cys Thr Val Pro Glu Ala Asp Gln
            115                 120                 125

Pro Val Arg Leu Thr Gln Leu Pro Glu Asn Gly Gly Trp Asn Ala Pro
130                 135                 140

Ile Thr Asp Phe Tyr Phe Gln Gln Cys Asp
145                 150

<210> SEQ ID NO 6
<211> LENGTH: 158
<212> TYPE: PRT
<213> ORGANISM: Homo sapiens

<400> SEQUENCE: 6

Met Glu Lys Ala Leu Lys Ile Asp Thr Pro Gln Gln Gly Ser Ile Gln
 1               5                  10                  15

Asp Ile Asn His Arg Val Trp Val Leu Gln Asp Gln Thr Leu Ile Ala
                 20                  25                  30

Val Pro Arg Lys Asp Arg Met Ser Pro Val Thr Ile Ala Leu Ile Ser
            35                  40                  45

Cys Arg His Val Glu Thr Leu Glu Lys Asp Arg Gly Asn Pro Ile Tyr
 50                  55                  60

Leu Gly Leu Asn Gly Leu Asn Leu Cys Leu Met Cys Ala Lys Val Gly
 65                  70                  75                  80

Asp Gln Pro Thr Leu Gln Leu Lys Glu Lys Asp Ile Met Asp Leu Tyr
                 85                  90                  95

Asn Gln Pro Glu Pro Val Lys Ser Phe Leu Phe Tyr His Ser Gln Ser
                100                 105                 110

Gly Arg Asn Ser Thr Phe Glu Ser Val Ala Phe Pro Gly Trp Phe Ile
            115                 120                 125

Ala Val Ser Ser Glu Gly Gly Cys Pro Leu Ile Leu Thr Gln Glu Leu
130                 135                 140

Gly Lys Ala Asn Thr Thr Asp Phe Gly Leu Thr Met Leu Phe
145                 150                 155

<210> SEQ ID NO 7
<211> LENGTH: 157
<212> TYPE: PRT
<213> ORGANISM: Homo sapiens

<400> SEQUENCE: 7

Met Asn Pro Gln Arg Glu Ala Ala Pro Lys Ser Tyr Ala Ile Arg Asp
 1               5                  10                  15

Ser Arg Gln Met Val Trp Val Leu Ser Gly Asn Ser Leu Ile Ala Ala
                 20                  25                  30

Pro Leu Ser Arg Ser Ile Lys Pro Val Thr Leu His Leu Ile Ala Cys
            35                  40                  45
```

-continued

```
Arg Asp Thr Glu Phe Ser Asp Lys Glu Lys Gly Asn Met Val Tyr Leu
 50                  55                  60

Gly Ile Lys Gly Lys Asp Leu Cys Leu Phe Cys Ala Glu Ile Gln Gly
 65                  70                  75                  80

Lys Pro Thr Leu Gln Leu Lys Glu Lys Asn Ile Met Asp Leu Tyr Val
                 85                  90                  95

Glu Lys Lys Ala Gln Lys Pro Phe Leu Phe Phe His Asn Lys Glu Gly
            100                 105                 110

Ser Thr Ser Val Phe Gln Ser Val Ser Tyr Pro Gly Trp Phe Ile Ala
                115                 120                 125

Thr Ser Thr Thr Ser Gly Gln Pro Ile Phe Leu Thr Lys Glu Arg Gly
            130                 135                 140

Ile Thr Asn Asn Thr Asn Phe Tyr Leu Asp Ser Val Glu
145                 150                 155
```

<210> SEQ ID NO 8
<211> LENGTH: 169
<212> TYPE: PRT
<213> ORGANISM: Homo sapiens

<400> SEQUENCE: 8

```
Met Arg Gly Thr Pro Gly Asp Ala Asp Gly Gly Arg Ala Val Tyr
 1               5                  10                  15

Gln Ser Met Cys Lys Pro Ile Thr Gly Thr Ile Asn Asp Leu Asn Gln
                20                  25                  30

Gln Val Trp Thr Leu Gln Gly Gln Asn Leu Val Ala Val Pro Arg Ser
            35                  40                  45

Asp Ser Val Thr Pro Val Thr Val Ala Val Ile Thr Cys Lys Tyr Pro
 50                  55                  60

Glu Ala Leu Glu Gln Gly Arg Gly Asp Pro Ile Tyr Leu Gly Ile Gln
 65                  70                  75                  80

Asn Pro Glu Met Cys Leu Tyr Cys Glu Lys Val Gly Glu Gln Pro Thr
                 85                  90                  95

Leu Gln Leu Lys Glu Gln Lys Ile Met Asp Leu Tyr Gly Gln Pro Glu
            100                 105                 110

Pro Val Lys Pro Phe Leu Phe Tyr Arg Ala Lys Thr Gly Arg Thr Ser
                115                 120                 125

Thr Leu Glu Ser Val Ala Phe Pro Asp Trp Phe Ile Ala Ser Ser Lys
            130                 135                 140

Arg Asp Gln Pro Ile Ile Leu Thr Ser Glu Leu Gly Lys Ser Tyr Asn
145                 150                 155                 160

Thr Ala Phe Glu Leu Asn Ile Asn Asp
                165
```

<210> SEQ ID NO 9
<211> LENGTH: 25
<212> TYPE: PRT
<213> ORGANISM: Homo sapiens

<400> SEQUENCE: 9

```
Trp Asp Val Asn Gln Lys Thr Phe Tyr Leu Arg Asn Asn Gln Leu Val
 1               5                  10                  15

Ala Gly Tyr Leu Gln Gly Pro Asn Val
                20                  25
```

<210> SEQ ID NO 10
<211> LENGTH: 5

```
<212> TYPE: PRT
<213> ORGANISM: Homo sapiens

<400> SEQUENCE: 10

Asn Leu Glu Glu Lys
1               5

<210> SEQ ID NO 11
<211> LENGTH: 32
<212> TYPE: PRT
<213> ORGANISM: Homo sapiens

<400> SEQUENCE: 11

Arg Ile Trp Asp Val Asn Gln Lys Thr Phe Tyr Leu Arg Asn Asn Gln
1               5                   10                  15

Leu Val Ala Gly Tyr Leu Gln Gly Pro Asn Val Asn Leu Glu Glu Lys
            20                  25                  30

<210> SEQ ID NO 12
<211> LENGTH: 7
<212> TYPE: PRT
<213> ORGANISM: Homo sapiens

<400> SEQUENCE: 12

Ala Met Glu Ala Asp Gln Pro
1               5

<210> SEQ ID NO 13
<211> LENGTH: 28
<212> TYPE: PRT
<213> ORGANISM: Homo sapiens

<400> SEQUENCE: 13

Phe Leu Cys Thr Ala Met Glu Ala Asp Gln Pro Val Ser Leu Thr Asn
1               5                   10                  15

Met Pro Asp Glu Gly Val Met Val Thr Lys Phe Tyr
            20                  25

<210> SEQ ID NO 14
<211> LENGTH: 10
<212> TYPE: PRT
<213> ORGANISM: Homo sapiens

<400> SEQUENCE: 14

Val Gln Gly Glu Glu Ser Asn Asp Lys Ile
1               5                   10

<210> SEQ ID NO 15
<211> LENGTH: 8
<212> TYPE: PRT
<213> ORGANISM: Homo sapiens

<400> SEQUENCE: 15

Lys Lys Lys Met Glu Lys Arg Phe
1               5

<210> SEQ ID NO 16
<211> LENGTH: 73
<212> TYPE: PRT
<213> ORGANISM: Homo sapiens

<400> SEQUENCE: 16

Phe Ser Met Ser Phe Val Gln Gly Glu Glu Ser Asn Asp Lys Ile Pro
1               5                   10                  15
```

```
Val Ala Leu Gly Leu Lys Glu Lys Asn Leu Tyr Leu Ser Cys Val Leu
         20                  25                  30

Lys Asp Asp Lys Pro Thr Leu Gln Leu Glu Ser Val Asp Pro Lys Asn
             35                  40                  45

Tyr Pro Lys Lys Met Glu Lys Arg Phe Val Phe Asn Lys Ile Glu
 50                  55                  60

Ile Asn Asn Lys Leu Glu Phe Glu Ser
 65                  70
```

<210> SEQ ID NO 17
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

```
Ala Pro Val Arg Ser Leu Ala Phe Arg Ile Trp Asp Val Asn Gln Lys
 1               5                  10                  15

Thr Phe Tyr Leu Arg Asn Asn Gln Leu Val Ala Gly Tyr Leu Gln Gly
             20                  25                  30

Pro Asn Val Asn Leu Glu Glu Lys Ile Asp Val Ser Phe Val Gln Gly
         35                  40                  45

Glu Glu Ser Asn Asp Lys Ile Pro Val Ala Leu Gly Ile His Gly Gly
     50                  55                  60

Lys Met Cys Leu Ser Cys Val Lys Ser Gly Asp Glu Thr Arg Leu Gln
 65                  70                  75                  80

Leu Glu Ala Val Asp Pro Lys Asn Tyr Pro Lys Lys Met Asp Lys
                 85                  90                  95

Arg Phe Ala Phe Ile Arg Ser Asp Ser Gly Pro Thr Thr Ser Phe Glu
             100                 105                 110

Ser Ala Ala Cys Pro Gly Trp Phe Leu Cys Thr Ala Met Glu Ala Asp
         115                 120                 125

Gln Pro Val Ser Leu Thr Asn Met Pro Asp Glu Gly Val Met Val Thr
     130                 135                 140

Lys Phe Tyr Met Gln Phe Val Ser Ser
145                 150
```

<210> SEQ ID NO 18
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

```
Ala Pro Val Arg Ser Leu Ala Phe Arg Ile Trp Asp Val Asn Gln Lys
 1               5                  10                  15

Thr Phe Tyr Leu Arg Asn Asn Gln Leu Val Ala Gly Tyr Leu Gln Gly
             20                  25                  30

Pro Asn Val Asn Leu Glu Glu Lys Ile Asp Val Ser Phe Val Gln Gly
         35                  40                  45

Glu Glu Ser Asn Asp Lys Ile Pro Val Ala Leu Gly Ile His Gly Gly
     50                  55                  60
```

Lys Met Cys Leu Ser Cys Val Lys Ser Gly Asp Glu Thr Arg Leu Gln
65                  70                  75                  80

Leu Glu Ala Val Asp Pro Lys Asn Tyr Pro Lys Lys Met Glu Lys
            85                  90                  95

Arg Phe Val Phe Asn Lys Ile Glu Ile Asn Asn Lys Leu Ser Phe Glu
                100                 105                 110

Ser Ala Ala Cys Pro Gly Trp Phe Leu Cys Thr Ala Met Glu Ala Asp
            115                 120                 125

Gln Pro Val Ser Leu Thr Asn Met Pro Asp Glu Gly Val Met Val Thr
        130                 135                 140

Lys Phe Tyr Met Gln Phe Val Ser Ser
145                 150

<210> SEQ ID NO 19
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Ala Pro Val Arg Ser Leu Ala Phe Arg Ile Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Asn Leu Glu Glu Lys Phe Ser Met Ser Phe Val Gln Gly
        35                  40                  45

Glu Glu Ser Asn Asp Lys Ile Pro Val Ala Leu Gly Leu Lys Glu Lys
    50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Met Glu Lys
            85                  90                  95

Arg Phe Val Phe Ile Arg Ser Asp Ser Gly Pro Thr Thr Ser Phe Glu
                100                 105                 110

Ser Ala Ala Cys Pro Gly Trp Phe Leu Cys Thr Ala Met Glu Ala Asp
            115                 120                 125

Gln Pro Val Ser Leu Thr Asn Met Pro Asp Glu Gly Val Met Val Thr
        130                 135                 140

Lys Phe Thr Met Gln Phe Val Ser Ser
145                 150

<210> SEQ ID NO 20
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Ala Pro Val Arg Ser Leu Ala Phe Arg Ile Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Asn Leu Glu Glu Lys Phe Ser Met Ser Phe Val Gln Gly

```
                 35                  40                  45

Glu Glu Ser Asn Asp Lys Ile Pro Val Ala Leu Gly Leu Lys Glu Lys
             50                  55                  60

Asn Leu Tyr Leu Ser Cys Val Leu Lys Asp Asp Lys Pro Thr Leu Gln
 65                  70                  75                  80

Leu Glu Ser Val Asp Pro Lys Asn Tyr Pro Lys Lys Met Glu Lys
                 85                  90                  95

Arg Phe Val Phe Asn Lys Ile Glu Ile Asn Asn Lys Leu Glu Phe Glu
                100                 105                 110

Ser Ala Ala Cys Pro Gly Trp Phe Leu Cys Thr Ala Met Glu Ala Asp
                115                 120                 125

Gln Pro Val Ser Leu Thr Asn Met Pro Asp Glu Gly Val Met Val Thr
            130                 135                 140

Lys Phe Thr Met Gln Phe Val Ser Ser
145                 150

<210> SEQ ID NO 21
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Ala Pro Val Arg Ser Leu Asn Cys Arg Ile Trp Asp Val Asn Gln Lys
1               5                  10                  15

Thr Phe Tyr Leu Arg Asn Asn Gln Leu Val Ala Gly Tyr Leu Gln Gly
                20                  25                  30

Pro Asn Val Asn Leu Glu Glu Lys Phe Ser Met Ser Phe Val Gln Gly
                35                  40                  45

Glu Glu Ser Asn Asp Lys Ile Pro Val Ala Leu Gly Leu Lys Glu Lys
             50                  55                  60

Asn Leu Tyr Leu Ser Cys Val Leu Lys Asp Asp Lys Pro Thr Leu Gln
 65                  70                  75                  80

Leu Glu Ser Val Asp Pro Lys Asn Tyr Pro Lys Lys Met Glu Lys
                 85                  90                  95

Arg Phe Val Phe Asn Lys Ile Glu Ile Asn Asn Lys Leu Glu Phe Glu
                100                 105                 110

Ser Ala Gln Phe Pro Asn Trp Phe Leu Cys Thr Ala Met Glu Ala Asp
                115                 120                 125

Gln Pro Val Ser Leu Thr Asn Met Pro Asp Glu Gly Val Met Val Thr
            130                 135                 140

Lys Phe Tyr Met Gln Phe Val Ser Ser
145                 150

<210> SEQ ID NO 22
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Asp Ile Cys Leu Pro Arg Trp Gly Cys Leu Trp
1               5                  10
```

<210> SEQ ID NO 23
<211> LENGTH: 152
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

Ala Pro Val Arg Ser Leu Asn Cys Thr Leu Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Glu Gln Gln Val Val Phe Ser Met Ser Phe Val Gln Gly
        35                  40                  45

Glu Glu Ser Asn Asp Lys Ile Pro Val Ala Leu Gly Leu Lys Glu Lys
    50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Met Glu Lys
                85                  90                  95

Arg Phe Val Phe Asn Lys Ile Glu Ile Asn Asn Lys Leu Glu Phe Glu
                100                 105                 110

Ser Ala Gln Phe Pro Asn Trp Tyr Ile Ser Thr Ser Met Glu Ala Asp
            115                 120                 125

Gln Pro Val Phe Leu Gly Gly Thr Lys Gly Gly Gln Asp Ile Thr Asp
        130                 135                 140

Phe Thr Met Gln Phe Val Ser Ser
145                 150

<210> SEQ ID NO 24
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

Ala Pro Val Arg Ser Leu Asn Cys Arg Ile Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Asn Leu Glu Glu Lys Phe Ser Met Ser Phe Val Gln Gly
        35                  40                  45

Glu Glu Ser Asn Asp Lys Ile Pro Val Ala Leu Gly Leu Lys Glu Lys
    50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Met Glu Lys
                85                  90                  95

Arg Phe Val Phe Asn Lys Ile Glu Ile Asn Asn Lys Leu Glu Phe Glu
                100                 105                 110

Ser Ala Gln Phe Pro Asn Trp Phe Leu Cys Thr Ala Met Glu Ala Asp
            115                 120                 125

Gln Pro Val Ser Leu Thr Asn Met Pro Asp Glu Gly Gln Asp Ile Thr
         130                 135                 140

Asp Phe Thr Met Gln Phe Val Ser Ser
145                 150

<210> SEQ ID NO 25
<211> LENGTH: 459
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
gcacctgtac gatcactggc cttcagaatc tgggatgtta accagaagac cttctatctg    60
aggaacaacc aactagttgc tggatacttg caaggaccaa atgtcaattt agaagaaaag   120
atagatgtgt cctttgtaca aggagaagaa agtaatgaca aaatacctgt ggccttgggc   180
atccatggag ggaagatgtg cctgtcctgt gtcaagtctg gtgatgagac agactccag    240 ctggaggcag ttgatcccaa aaattaccca agaagaaga tggacaagcg cttcgccttc    300
atccgctcag acagcggccc caccaccagt tttgagtctg ccgcctgccc cggttggttc    360
ctctgcacag cgatggaagc tgaccagccc gtcagcctca ccaatatgcc tgacgaaggc    420
gtcatggtca ccaaattcta catgcaattt gtgtcttcc                           459

<210> SEQ ID NO 26
<211> LENGTH: 459
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
gcacctgtac gatcactggc cttcagaatc tgggatgtta accagaagac cttctatctg    60
aggaacaacc aactagttgc tggatacttg caaggaccaa atgtcaattt agaagaaaag   120
atagatgtgt cctttgtaca aggagaagaa agtaatgaca aaatacctgt ggccttgggc   180
atccatggag ggaagatgtg cctgtcctgt gtcaagtctg gtgatgagac agactccag    240 ctggaggcag ttgatcccaa aaattaccca agaagaaga tggaaaagcg atttgtcttc    300
aacaagatag aaatcaataa caagctgagt tttgagtctg ccgcctgccc cggttggttc    360
ctctgcacag cgatggaagc tgaccagccc gtcagcctca ccaatatgcc tgacgaaggc    420
gtcatggtca ccaaattcta catgcaattt gtgtcttcc                           459

<210> SEQ ID NO 27
<211> LENGTH: 459
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
gcacctgtac gatcactggc cttcagaatc tgggatgtta accagaagac cttctatctg    60
aggaacaacc aactagttgc tggatacttg caaggaccaa atgtcaattt agaagaaaag   120
ttctccatgt cctttgtaca aggagaagaa agtaatgaca aaatacctgt ggccttgggc   180

```
ctcaaggaaa agaatctgta cctgtcctgc gtgttgaaag atgataagcc cactctacag    240
ctggagagtg tagatcccaa aaattaccca agaagaaga tggaaaagcg atttgtcttc     300
atccgctcag acagcggccc caccaccagt tttgagtctg ccgcctgccc cggttggttc    360
ctctgcacag cgatggaagc tgaccagccc gtcagcctca ccaatatgcc tgacgaaggc    420
gtcatggtca ccaaattcac catgcaattt gtgtcttcc                           459
```

<210> SEQ ID NO 28
<211> LENGTH: 459
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28

```
gcacctgtac gatcactggc cttcagaatc tgggatgtta accagaagac cttctatctg    60
aggaacaacc aactagttgc tggatacttg caaggaccaa atgtcaattt agaagaaaag    120
ttctccatgt cctttgtaca aggagaagaa agtaatgaca aaatacctgt ggccttgggc    180
ctcaaggaaa agaatctgta cctgtcctgc gtgttgaaag atgataagcc cactctacag    240
ctggagagtg tagatcccaa aaattaccca agaagaaga tggaaaagcg atttgtcttc     300
aacaagatag aaatcaataa caagctggaa tttgagtctg ccgcctgccc cggttggttc    360
ctctgcacag cgatggaagc tgaccagccc gtcagcctca ccaatatgcc tgacgaaggc    420
gtcatggtca ccaaattcac catgcaattt gtgtcttcc                           459
```

<210> SEQ ID NO 29
<211> LENGTH: 459
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29

```
gcacctgtac gatcactgaa ctgcagaatc tgggatgtta accagaagac cttctatctg    60
aggaacaacc aactagttgc tggatacttg caaggaccaa atgtcaattt agaagaaaag    120
ttctccatgt cctttgtaca aggagaagaa agtaatgaca aaatacctgt ggccttgggc    180
ctcaaggaaa agaatctgta cctgtcctgc gtgttgaaag atgataagcc cactctacag    240
ctggagagtg tagatcccaa aaattaccca agaagaaga tggaaaagcg atttgtcttc     300
aacaagatag aaatcaataa caagctggaa tttgagtctg cccagttccc caactggttc    360
ctctgcacag cgatggaagc tgaccagccc gtcagcctca ccaatatgcc tgacgaaggc    420
gtcatggtca ccaaattcta catgcaattt gtgtcttcc                           459
```

<210> SEQ ID NO 30
<211> LENGTH: 456
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30

```
gcacctgtac gatcactgaa ctgcacgctc tgggatgtta accagaagac cttctatctg    60
aggaacaacc aactagttgc tggatacttg caaggaccaa atgtcgagca acaagtggtg   120
ttctccatgt cctttgtaca aggagaagaa agtaatgaca aaatacctgt ggccttgggc   180
ctcaaggaaa agaatctgta cctgtcctgc gtgttgaaag atgataagcc cactctacag   240
ctggagagtg tagatcccaa aaattaccca agaagaaga tggaaaagcg atttgtcttc    300
aacaagatag aaatcaataa caagctggaa tttgagtctg cccagttccc caactggtac   360
atcagcacct ctatggaagc tgaccagccc gtcttcctgg agggaccaa aggcggccag    420 gatataactg acttcaccat gcaatttgtg tcttcc                             456
```

<210> SEQ ID NO 31
<211> LENGTH: 459
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 31

```
gcacctgtac gatcactgaa ctgcagaatc tgggatgtta accagaagac cttctatctg    60
aggaacaacc aactagttgc tggatacttg caaggaccaa atgtcaattt agaagaaaag   120
ttctccatgt cctttgtaca aggagaagaa agtaatgaca aaatacctgt ggccttgggc   180
ctcaaggaaa agaatctgta cctgtcctgc gtgttgaaag atgataagcc cactctacag   240
ctggagagtg tagatcccaa aaattaccca agaagaaga tggaaaagcg atttgtcttc    300
aacaagatag aaatcaataa caagctggaa tttgagtctg cccagttccc caactggttc   360
ctctgcacag cgatggaagc tgaccagccc gtcagcctca ccaatatgcc tgacgaaggc   420
caggatataa ctgacttcac catgcaattt gtgtcttcc                          459
```

<210> SEQ ID NO 32
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 32

```
Ala Pro Val Arg Ser Leu Ala Phe Arg Ile Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Asn Leu Glu Glu Lys Phe Ser Met Ser Phe Val Gln Gly
        35                  40                  45

Glu Glu Ser Asn Asp Lys Ile Pro Val Ala Leu Gly Leu Lys Glu Lys
    50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Met Glu Lys
                85                  90                  95

Arg Phe Val Phe Asn Lys Ile Glu Ile Asn Asn Lys Leu Glu Phe Glu
            100                 105                 110

Ser Ala Gln Phe Pro Asn Trp Phe Leu Cys Thr Ala Met Glu Ala Asp
        115                 120                 125
```

Gln Pro Val Ser Leu Thr Asn Met Pro Asp Glu Gly Val Met Val Thr
    130                 135                 140

Lys Phe Tyr Met Gln Phe Val Ser Ser
145                 150

<210> SEQ ID NO 33
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Ala Pro Val Arg Ser Gln Ala Phe Arg Ile Trp Asp Val Asn Gln Lys
1               5                   10                  15

Thr Phe Tyr Leu Arg Asn Asn Gln Leu Val Ala Gly Tyr Leu Gln Gly
                20                  25                  30

Pro Asn Val Asn Leu Glu Glu Lys Phe Ser Met Ser Phe Val Gln Gly
            35                  40                  45

Glu Glu Ser Asn Asp Lys Ile Pro Val Ala Leu Gly Leu Lys Glu Lys
50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Met Glu Lys
                85                  90                  95

Arg Phe Val Phe Asn Lys Ile Glu Ile Asn Asn Lys Leu Glu Phe Glu
            100                 105                 110

Ser Ala Gln Phe Pro Asn Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Met Gln Phe Val Ser Ser
145                 150

<210> SEQ ID NO 34
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Ala Pro Val Arg Ser Leu Ala Phe Arg Ile Trp Asp Val Asn Gln Lys
1               5                   10                  15

Thr Phe Tyr Leu Arg Asn Asn Gln Leu Val Ala Gly Tyr Leu Gln Gly
                20                  25                  30

Pro Asn Val Asn Leu Glu Glu Lys Ile Asp Val Ser Phe Val Gln Gly
            35                  40                  45

Glu Glu Ser Asn Asp Lys Ile Pro Val Ala Leu Gly Leu Lys Glu Lys
50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Lys Met Glu Lys
                85                  90                  95

```
Arg Phe Val Phe Asn Lys Ile Glu Ile Asn Asn Lys Leu Glu Phe Glu
            100                 105                 110

Ser Ala Gln Phe Pro Asn Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Met Gln Phe Val Ser Ser
145                 150
```

<210> SEQ ID NO 35
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 35

```
Ala Pro Val Arg Ser Leu Asn Cys Arg Ile Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Asn Leu Glu Glu Lys Ile Asp Val Ser Phe Val Gln Gly
        35                  40                  45

Glu Glu Ser Asn Asp Lys Ile Pro Val Ala Leu Gly Leu Lys Glu Lys
    50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Lys Met Glu Lys
                85                  90                  95

Arg Phe Val Phe Asn Lys Ile Glu Ile Asn Asn Lys Leu Glu Phe Glu
            100                 105                 110

Ser Ala Gln Phe Pro Asn Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Met Gln Phe Val Ser Ser
145                 150
```

<210> SEQ ID NO 36
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

```
Ala Pro Val Arg Ser Leu Asn Cys Arg Ile Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Asn Leu Glu Glu Lys Phe Ser Met Ser Phe Val Gln Gly
        35                  40                  45

Glu Glu Ser Asn Asp Lys Ile Pro Val Ala Leu Gly Leu Lys Glu Lys
    50                  55                  60

Asn Leu Tyr Leu Ser Cys Val Leu Lys Asp Asp Lys Pro Thr Leu Gln
```

```
                65                  70                  75                  80

Leu Glu Ser Val Asp Pro Lys Asn Tyr Pro Lys Lys Lys Met Glu Lys
                85                  90                  95

Arg Phe Val Phe Asn Lys Ile Glu Ile Asn Asn Lys Leu Glu Phe Glu
            100                 105                 110

Ser Ala Gln Phe Pro Asn Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Thr Met Gln Phe Val Ser Ser
145                 150

<210> SEQ ID NO 37
<211> LENGTH: 151
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Ala Pro Val Arg Ser Leu Ala Phe Arg Ile Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Asn Leu Glu Glu Lys Phe Ser Met Ser Phe Val Gln Gly
        35                  40                  45

Glu Glu Ser Asn Asp Lys Ile Pro Val Ala Leu Gly Leu Lys Glu Lys
    50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Lys Met Glu Lys
                85                  90                  95

Arg Phe Val Phe Asn Lys Ile Glu Ile Asn Asn Lys Leu Glu Phe Glu
            100                 105                 110

Ser Ala Gln Phe Pro Asn Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp
145                 150

<210> SEQ ID NO 38
<211> LENGTH: 151
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Ala Pro Val Arg Ser Leu Asn Cys Arg Ile Trp Asp Val Asn Gln Lys
1               5                   10                  15

Thr Phe Tyr Leu Arg Asn Asn Gln Leu Val Ala Gly Tyr Leu Gln Gly
            20                  25                  30

Pro Asn Val Asn Leu Glu Glu Lys Phe Ser Met Ser Phe Val Gln Gly
        35                  40                  45
```

```
Glu Glu Ser Asn Asp Lys Ile Pro Val Ala Leu Gly Leu Lys Glu Lys
            50                  55                  60

Asn Leu Tyr Leu Ser Cys Val Leu Lys Asp Asp Lys Pro Thr Leu Gln
 65                  70                  75                  80

Leu Glu Ser Val Asp Pro Lys Asn Tyr Pro Lys Lys Met Glu Lys
                 85                  90                  95

Arg Phe Val Phe Asn Lys Ile Glu Ile Asn Asn Lys Leu Glu Phe Glu
                100                 105                 110

Ser Ala Gln Phe Pro Asn Trp Phe Leu Cys Thr Ala Met Glu Ala Asp
                115                 120                 125

Gln Pro Val Ser Leu Thr Asn Met Pro Asp Glu Gly Val Met Val Thr
                130                 135                 140

Lys Phe Tyr Phe Gln Glu Asp
145                 150
```

<210> SEQ ID NO 39
<211> LENGTH: 165
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

```
Ser Ala Pro Phe Ser Phe Leu Ser Asn Val Lys Tyr Asn Phe Met Arg
 1               5                  10                  15

Ile Ile Lys Tyr Glu Phe Arg Ile Trp Asp Val Asn Gln Lys Thr Phe
                20                  25                  30

Tyr Leu Arg Asn Asn Gln Leu Val Ala Gly Tyr Leu Gln Gly Pro Asn
             35                  40                  45

Val Asn Leu Glu Glu Lys Phe Asp Met Gly Ala Tyr Lys Ser Ser Lys
 50                  55                  60

Asp Asp Ala Lys Ile Thr Val Ile Leu Arg Ile Ser Lys Thr Gln Leu
 65                  70                  75                  80

Tyr Val Thr Ala Gln Asp Glu Asp Gln Pro Val Leu Leu Lys Glu Met
                 85                  90                  95

Pro Glu Ile Pro Lys Thr Ile Thr Gly Ser Glu Thr Asn Leu Leu Phe
                100                 105                 110

Phe Trp Glu Thr His Gly Thr Lys Asn Tyr Phe Thr Ser Val Ala His
                115                 120                 125

Pro Asn Leu Phe Leu Cys Thr Ala Met Glu Ala Asp Gln Pro Val Ser
                130                 135                 140

Leu Thr Asn Met Pro Asp Glu Gly Val Met Val Thr Lys Phe Tyr Ile
145                 150                 155                 160

Leu Glu Asn Gln Ala
                165
```

<210> SEQ ID NO 40
<211> LENGTH: 160
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

```
Asp Lys Pro Thr Leu Gln Leu Glu Ser Val Asp Pro Lys Asn Tyr Pro
1               5                   10                  15

Lys Lys Lys Met Glu Lys Arg Phe Val Phe Asn Lys Ile Glu Ile Asn
            20                  25                  30

Asn Lys Leu Glu Phe Glu Ser Ala Gln Phe Pro Asn Trp Phe Leu Cys
            35                  40                  45

Thr Ala Met Glu Ala Asp Gln Pro Val Ser Leu Thr Asn Met Pro Asp
50                  55                  60

Glu Gly Val Met Val Thr Lys Phe Tyr Met Gln Phe Val Ser Ser Gly
65                  70                  75                  80

Gly Ser Gly Gly Gly Ser Ala Pro Val Arg Ser Leu Asn Cys Arg Ile
                85                  90                  95

Trp Asp Val Asn Gln Lys Thr Phe Tyr Leu Arg Asn Asn Gln Leu Val
            100                 105                 110

Ala Gly Tyr Leu Gln Gly Pro Asn Val Asn Leu Glu Glu Lys Phe Ser
            115                 120                 125

Met Ser Phe Val Gln Gly Glu Ser Asn Asp Lys Ile Pro Val Ala
            130                 135                 140

Leu Gly Leu Lys Glu Lys Asn Leu Tyr Leu Ser Cys Val Leu Lys Asp
145                 150                 155                 160
```

<210> SEQ ID NO 41
<211> LENGTH: 160
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

```
Asn Tyr Pro Lys Lys Lys Met Glu Lys Arg Phe Val Phe Asn Lys Ile
1               5                   10                  15

Glu Ile Asn Asn Lys Leu Glu Phe Glu Ser Ala Gln Phe Pro Asn Trp
            20                  25                  30

Phe Leu Cys Thr Ala Met Glu Ala Asp Gln Pro Val Ser Leu Thr Asn
            35                  40                  45

Met Pro Asp Glu Gly Val Met Val Thr Lys Phe Tyr Met Gln Phe Val
50                  55                  60

Ser Ser Gly Gly Ser Gly Gly Gly Ser Ala Pro Val Arg Ser Leu Asn
65                  70                  75                  80

Cys Arg Ile Trp Asp Val Asn Gln Lys Thr Phe Tyr Leu Arg Asn Asn
            85                  90                  95

Gln Leu Val Ala Gly Tyr Leu Gln Gly Pro Asn Val Asn Leu Glu Glu
            100                 105                 110

Lys Phe Ser Met Ser Phe Val Gln Gly Glu Glu Ser Asn Asp Lys Ile
            115                 120                 125

Pro Val Ala Leu Gly Leu Lys Glu Lys Asn Leu Tyr Leu Ser Cys Val
            130                 135                 140

Leu Lys Asp Asp Lys Pro Thr Leu Gln Leu Glu Ser Val Asp Pro Lys
145                 150                 155                 160
```

<210> SEQ ID NO 42
<211> LENGTH: 6
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic 6xHis tag"

<400> SEQUENCE: 42

His His His His His His
1               5

<210> SEQ ID NO 43
<211> LENGTH: 7
<212> TYPE: PRT
<213> ORGANISM: Homo sapiens

<400> SEQUENCE: 43

Tyr Leu Gln Gly Pro Asn Val
1               5

<210> SEQ ID NO 44
<211> LENGTH: 8
<212> TYPE: PRT
<213> ORGANISM: Homo sapiens

<400> SEQUENCE: 44

Met Glu Ala Asp Gln Pro Val Ser
1               5

<210> SEQ ID NO 45
<211> LENGTH: 6
<212> TYPE: PRT
<213> ORGANISM: Homo sapiens

<400> SEQUENCE: 45

Arg Ser Leu Ala Phe Arg
1               5

<210> SEQ ID NO 46
<211> LENGTH: 6
<212> TYPE: PRT
<213> ORGANISM: Homo sapiens

<400> SEQUENCE: 46

Ile Asp Val Ser Phe Val
1               5

<210> SEQ ID NO 47
<211> LENGTH: 6
<212> TYPE: PRT
<213> ORGANISM: Homo sapiens

<400> SEQUENCE: 47

Lys Lys Met Asp Lys Arg
1               5

<210> SEQ ID NO 48
<211> LENGTH: 6
<212> TYPE: PRT
<213> ORGANISM: Homo sapiens

<400> SEQUENCE: 48

Lys Phe Tyr Met Gln Phe
1               5

<210> SEQ ID NO 49
<211> LENGTH: 6
<212> TYPE: PRT
<213> ORGANISM: Homo sapiens
```

```
<400> SEQUENCE: 49

Asn Lys Leu Ser Phe Glu
1               5

<210> SEQ ID NO 50
<211> LENGTH: 6
<212> TYPE: PRT
<213> ORGANISM: Homo sapiens

<400> SEQUENCE: 50

Glu Glu Lys Phe Ser Met
1               5

<210> SEQ ID NO 51
<211> LENGTH: 6
<212> TYPE: PRT
<213> ORGANISM: Homo sapiens

<400> SEQUENCE: 51

Arg Phe Val Phe Ile Arg
1               5

<210> SEQ ID NO 52
<211> LENGTH: 6
<212> TYPE: PRT
<213> ORGANISM: Homo sapiens

<400> SEQUENCE: 52

Val Thr Lys Phe Thr Met
1               5

<210> SEQ ID NO 53
<211> LENGTH: 6
<212> TYPE: PRT
<213> ORGANISM: Homo sapiens

<400> SEQUENCE: 53

Phe Glu Ser Ala Ala Cys
1               5

<210> SEQ ID NO 54
<211> LENGTH: 6
<212> TYPE: PRT
<213> ORGANISM: Homo sapiens

<400> SEQUENCE: 54

Val Thr Lys Phe Thr Met
1               5

<210> SEQ ID NO 55
<211> LENGTH: 6
<212> TYPE: PRT
<213> ORGANISM: Homo sapiens

<400> SEQUENCE: 55

Leu Asn Cys Arg Ile Trp
1               5

<210> SEQ ID NO 56
<211> LENGTH: 6
<212> TYPE: PRT
<213> ORGANISM: Homo sapiens

<400> SEQUENCE: 56
```

```
Pro Asn Trp Phe Leu Cys
1               5

<210> SEQ ID NO 57
<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(14)
<223> OTHER INFORMATION: Any amino acid
<220> FEATURE:
<221> NAME/KEY: misc_feature
<222> LOCATION: (6)..(14)
<223> OTHER INFORMATION: /note="This region may encompass 8 to 9
      residues"
<220> FEATURE:
<221> NAME/KEY: MOD_RES
<222> LOCATION: (17)..(18)
<223> OTHER INFORMATION: Any amino acid
<220> FEATURE:
<221> NAME/KEY: MOD_RES
<222> LOCATION: (22)..(49)
<223> OTHER INFORMATION: Any amino acid
<220> FEATURE:
<221> NAME/KEY: misc_feature
<222> LOCATION: (22)..(49)
<223> OTHER INFORMATION: /note="This region may encompass 18 to 28
      residues"
<220> FEATURE:
<221> NAME/KEY: MOD_RES
<222> LOCATION: (52)..(58)
<223> OTHER INFORMATION: Any amino acid
<220> FEATURE:
<221> NAME/KEY: MOD_RES
<222> LOCATION: (63)..(65)
<223> OTHER INFORMATION: Any amino acid
<220> FEATURE:
<221> NAME/KEY: MOD_RES
<222> LOCATION: (67)..(69)
<223> OTHER INFORMATION: Any amino acid
<220> FEATURE:
<221> NAME/KEY: MOD_RES
<222> LOCATION: (74)..(74)
<223> OTHER INFORMATION: Any amino acid
<220> FEATURE:
<221> NAME/KEY: MOD_RES
<222> LOCATION: (76)..(84)
<223> OTHER INFORMATION: Any amino acid
<220> FEATURE:
<221> NAME/KEY: misc_feature
<222> LOCATION: (76)..(84)
<223> OTHER INFORMATION: /note="This region may encompass 8 to 9
      residues"
<220> FEATURE:
<221> NAME/KEY: MOD_RES
<222> LOCATION: (86)..(87)
<223> OTHER INFORMATION: Any amino acid
<220> FEATURE:
<221> NAME/KEY: MOD_RES
<222> LOCATION: (91)..(91)
<223> OTHER INFORMATION: Any amino acid
<220> FEATURE:
<221> NAME/KEY: MOD_RES
<222> LOCATION: (93)..(102)
<223> OTHER INFORMATION: Any amino acid
<220> FEATURE:
<221> NAME/KEY: MOD_RES
<222> LOCATION: (107)..(108)
```

```
<223> OTHER INFORMATION: Any amino acid
<220> FEATURE:
<221> NAME/KEY: MOD_RES
<222> LOCATION: (110)..(110)
<223> OTHER INFORMATION: Any amino acid
<220> FEATURE:
<221> NAME/KEY: MOD_RES
<222> LOCATION: (112)..(114)
<223> OTHER INFORMATION: Any amino acid
<220> FEATURE:
<221> NAME/KEY: MOD_RES
<222> LOCATION: (116)..(121)
<223> OTHER INFORMATION: Any amino acid
<220> FEATURE:
<221> NAME/KEY: MOD_RES
<222> LOCATION: (124)..(124)
<223> OTHER INFORMATION: Any amino acid
<220> FEATURE:
<221> NAME/KEY: MOD_RES
<222> LOCATION: (126)..(131)
<223> OTHER INFORMATION: Any amino acid
<220> FEATURE:
<221> NAME/KEY: misc_feature
<222> LOCATION: (126)..(131)
<223> OTHER INFORMATION: /note="This region may encompass 5 to 6
      residues"
<220> FEATURE:
<221> NAME/KEY: MOD_RES
<222> LOCATION: (133)..(135)
<223> OTHER INFORMATION: Any amino acid
<220> FEATURE:
<221> NAME/KEY: MOD_RES
<222> LOCATION: (137)..(137)
<223> OTHER INFORMATION: Any amino acid
<220> FEATURE:
<221> NAME/KEY: MOD_RES
<222> LOCATION: (139)..(140)
<223> OTHER INFORMATION: Any amino acid

<400> SEQUENCE: 57

Asp Xaa Xaa Gln Lys Xaa Xaa Xaa Xaa Xaa Xaa Xaa Xaa Leu Ala
1               5                   10                  15

Xaa Xaa Leu Gln Gly Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Leu Gly Xaa Xaa Xaa Xaa Xaa Xaa Leu Ser Cys Val Xaa Xaa
    50                  55                  60

Xaa Asp Xaa Xaa Xaa Leu Gln Leu Glu Xaa Val Xaa Xaa Xaa Xaa
65                  70                  75                  80

Xaa Xaa Xaa Xaa Lys Xaa Xaa Lys Arg Phe Xaa Phe Xaa Xaa Xaa
                85                  90                  95

Xaa Xaa Xaa Xaa Xaa Xaa Phe Glu Ser Ala Xaa Xaa Pro Xaa Trp Xaa
            100                 105                 110

Xaa Xaa Thr Xaa Xaa Xaa Xaa Xaa Xaa Pro Val Xaa Leu Xaa Xaa Xaa
            115                 120                 125

Xaa Xaa Xaa Gly Xaa Xaa Xaa Thr Xaa Phe Xaa Xaa Gln
            130                 135                 140

<210> SEQ ID NO 58
<211> LENGTH: 5
<212> TYPE: PRT
<213> ORGANISM: Homo sapiens

<400> SEQUENCE: 58

Ala Pro Val Arg Ser
1               5
```